US012168773B2

(12) United States Patent
Larsen

(10) Patent No.: US 12,168,773 B2
(45) Date of Patent: Dec. 17, 2024

(54) ENGINEERED PHOSPHOENOLPYRUVATE CARBOXYLASE ENZYMES

(71) Applicant: The Regents of the University of California, Oakland, CA (US)

(72) Inventor: Paul B. Larsen, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 295 days.

(21) Appl. No.: 17/601,913

(22) PCT Filed: Apr. 10, 2020

(86) PCT No.: PCT/US2020/027746
§ 371 (c)(1),
(2) Date: Oct. 6, 2021

(87) PCT Pub. No.: WO2020/210687
PCT Pub. Date: Oct. 15, 2020

(65) Prior Publication Data
US 2022/0145319 A1   May 12, 2022

Related U.S. Application Data

(60) Provisional application No. 62/832,727, filed on Apr. 11, 2019.

(51) Int. Cl.
C12N 15/82 (2006.01)
C12N 9/88 (2006.01)

(52) U.S. Cl.
CPC ........... *C12N 15/8271* (2013.01); *C12N 9/88* (2013.01); *C12N 15/8243* (2013.01); *C12N 15/8262* (2013.01); *C12Y 401/01031* (2013.01); *C12N 2820/002* (2013.01); *C12N 2820/007* (2013.01)

(58) Field of Classification Search
None
See application file for complete search history.

(56) References Cited

U.S. PATENT DOCUMENTS

| | | |
|---|---|---|
| 5,177,010 A | 1/1993 | Goldman et al. |
| 5,416,011 A | 5/1995 | Hinchee et al. |
| 5,563,055 A | 10/1996 | Townsend et al. |
| 5,569,834 A | 10/1996 | Hinchee et al. |
| 5,824,877 A | 10/1998 | Hinchee et al. |
| 5,968,830 A | 10/1999 | Dan et al. |
| 5,981,840 A | 11/1999 | Zhao et al. |
| 6,100,447 A | 8/2000 | Wu et al. |
| 2011/0023188 A1* | 1/2011 | Kim ............ C12N 9/001 800/290 |
| 2014/0298544 A1* | 10/2014 | Li ................ C12N 9/88 800/278 |
| 2018/0371487 A1 | 12/2018 | Yang et al. |

FOREIGN PATENT DOCUMENTS

CN   1865443 A   11/2006

OTHER PUBLICATIONS

Hu et al. Accession No. D7KKG4, Deposited, Aug. 10, 2010.*
Begum et al. Journal of Plant Nutrition (2009), vol. 32, pp. 84-96.*
Begum et al. Journal of Plant Nutrition (2009), 32:84-96.*
Jeanneau et al (Journal of Experimental Botany (2002) 53(376):1837-1845.*
Rosnow et al. Journal of Experimental Botany (2015) 66(22):7347-7358.*
Liu et al. Acta Pharmaceutica Sinica B (2017) 7(3): 292-302.*
Aarts et al., (1995). "Molecular Characterization of the CER1 Gene of *Arabidopsis* involved in Epicuticular Wax Biosynthesis and Pollen Fertility," Plant Cell, 7:2115-2127.
Alam et al., (1999). "Transgenic insect-resistant maintainer line (IR68899B) for improvement of hybrid rice," Plant Cell Rep., 18:572-575.
Altschul et al., (1997). "Gapped BLAST and PSI-BLAST: a new generation of protein database search programs," Nucleic acids research, 25(17):3389-3402.
Altschul et al., (1990). "Basic local alignment search tool," Journal of Molecular Biology, 215(3):403-410.
An, (1986). "Development of plant promoter expression vectors and their use for analysis of differential activity of nopaline synthase promoter in transformed tobacco cells," Plant Physiol., 81:86-91.
Back et al., (1991). "Isolation of the spinach nitrite reductase gene promoter which confers nitrate inducibility on GUS gene expression in transgenic tobacco," Plant Mol. Biol., 17:9-18.
Benfey et al., (1990). "The Cauliflower Mosaic Virus 35S Promoter: Combinatorial Regulation of Transcription in Plants," Science, 250:959-966.
Bezerra et al., (1995). "A corm-specific gene encodes tarin, a major globulin of taro (*Colocasia esculenta* L. Schott)," Plant Mol. Biol., 28:137-144.
Bi et al., (1997). "Does Salicylic Acid Act as a Signal in Cotton for Induced Resistance to *Helicoverpa zea*," journal of Chemical Ecology, 23(7):1805-1818.
Busk et al., (1997). "Regulatory elements in vivo in the promoter of the abscisic acid responsive gene rab17 from maize," Plant J., 11(6):1285-1295.
Casal et al., (1998). "Different Phototransduction Kinetics of Phytochrome A and Phytochrome B in *Arabidopsis thaliana*," Plant Physiol., 116:1533-1538.
Chen et al., (1996). "The promoter of a $H_2O_2$-inducible, *Arabidopsis glutathione* S-transferase gene contains closely linked OBF- and OBP1-binding sites," Plant J., 10(6):955-966.

(Continued)

*Primary Examiner* — Medina A Ibrahim
(74) *Attorney, Agent, or Firm* — Morrison & Foerster LLP

(57) ABSTRACT

The present disclosure provides plants that express a variant phosphoenolpyruvate carboxylase (PEPC) enzyme. The plants have enhanced resistance to aluminum than comparable plants that lack the variant PEPC enzyme. In addition, the plants more effectively sequester carbon, extract phosphate, and produce oxaloacetate-derived amino acids and glucose than comparable plants that lack the variant PEPC enzyme. The disclosure also provides tools for production of plants that express the variant PEPC enzyme.

6 Claims, 12 Drawing Sheets

Specification includes a Sequence Listing.

(56) References Cited

OTHER PUBLICATIONS

Cheng et al., (2014). "Interactions between light intensity and phosphorus nutrition affect the phosphate-mining capacity of white lupin (*Lupinus albus* L.)," Journal of Experimental Botany, 65(12):2995-3003.
Christopherson et al., (1992). "Ecdysteroid-dependent regulation of genes in mammalian cells by a *Drosophila ecdysone* receptor and chimeric transactivators," PNAS USA, 89:6314-6318.
Chylinski et al., (2013). "The tracrRNA and Cas9 families of type II CRISPR-Cas immunity systems," RNA Biol., 10(5):726-737.
Comai et al., (1990). "Novel and useful properties of a chimeric plant promoter combining CaMV 35S and MAS elements," Plant Mol. Biol., 15:373-381.
Conceição et al., (1994). "A cotyledon regulatory region is responsible for the different spatial expression patterns of *Arabidopsis* 2S albumin genes," The Plant J., 5(4):493-505.
De Castro et al., (1992). "Spatial and Temporal Gene Expression Patterns Occur during Corm Development," Plant Cell, 4:1549-1559.
De Veylder et al., (1997). "Herbicide safener-inducible gene expression in *Arabidopsis thaliana*," Plant Cell Physiol., 38(5):568-577.
Di Laurenzio et al., (1996). "The SCARECROW Gene Regulates an Asymmetric Cell Division That Is Essential for Generating the Radial Organization of the *Arabidopsis* Root," Cell, 86:423-433.
Enjuto et al., (1995). "Expression of the Arabidopsis HMG2 gene, encoding 3-hydroxy-3-methylglutaryl coenzyme A reductase, is restricted to meristematic and floral tissues," Plant Cell, 7:517-527.
Extended European Search Report and Written Opinion received for European Patent Application No. 20788568.2 mailed on Jul. 10, 2023, 7 pages.
Feinbaum et al., (1991). "High intensity and blue light regulated expression of chimeric chalcone synthase genes in transgenic *Arabidopsis thaliana* plants," Mol. Gen. Genet., 226:449-456.
Fraley et al., (1983). "Expression of bacterial genes in plant cells," PNAS USA, 80:4803-4807.
Fromm et al., (1985). "Expression of genes transferred into monocot and dicot plant cells by electroporation," PNAS USA, 82:5824-5828.
Furst et al., (1988). "Copper activates metallothionein gene transcription by altering the conformation of a specific DNA binding protein," Cell, 55:705-717.
Fütterer et al., (1990). "Cauliflower mosaic virus as a gene expression vector for plants," Physiol. Plant, 79(1):154-157.
Gatz et al., (1992). "Stringent repression and homogeneous derepression by tetracycline of a modified CaMV 35S promoter in intact transgenic tobacco plants," Plant J., 2(3):397-404.
Granger et al., (1996). "Isolation of an *Arabidopsis* homologue of the maize homeobox Knotted-1 gene," Plant Mol. Biol., 31:373-378.
Guo et al., (2015). "Chapter 14, Sorghum (Sorghum bicolor)," Methods Mol Biol, 1223:181-188.
Hake et al., (1995). "Homeobox genes in the functioning of plant meristems," Philos. Trans. R. Soc. Lond. B. Biol. Sci., 350:45-51.
Hansen et al., (1997). "Wound-inducible and organ-specific expression of ORF13 from Agrobacterium rhizogenes 8196 T-DNA in transgenic tobacco plants," Mol. Gen. Genet., 254:337-343.
Holtorf et al., (1995). "Comparison of different constitutive and inducible promoters for the overexpression of transgenes in *Arabidopsis thaliana*," Plant Mol. Biol., 29:637-646.
Hooker et al., (2002). "Significance of the expression of the CER6 condensing enzyme for cuticular wax production in *Arabidopsis*," Plant Physiol, 129:1568-1580.
Horsch et al., (1984). "Inheritance of Functional Foreign Genes in Plants," Science, 233:496-498.
Hou et al., (2013). "Efficient genome engineering in human pluripotent stem cells using Cas9 from Neisseria meningitidis," PNAS USA, 110(39):15644-15649.

Howe et al., (2006). "Rapid and reproducible Agrobacterium-mediated transformation of sorghum," Plant Cell Rep, 25(8):784-791.
Hsu et al., (2014). "Development and Applications of CRISPR-Cas9 for Genome Engineering," Cell, 157(6):1262-1278, 34 pages.
Huang et al., (1997). "The *Arabidopsis* ACT11 actin gene is strongly expressed in tissues of the emerging inflorescence, pollen, and developing ovules," Plant Mol. Biol., 33:125-139.
International Search Report and Written Opinion for International Patent Application No. PCT/US2020/027746 mailed on Sep. 11, 2020, 13 pages.
Jinek et al., (2012). "A programmable dual-RNA-guided DNA endonuclease in adaptive bacterial immunity," Science, 337(6096):816-821.
Josefsson et al., (1987). "Structure of a gene encoding the 1.7 S storage protein, napin, from *Brassica napus*," The Journal of Biological Chemistry, 262(25):12196-12201.
Kandoi et al., (2016). "Towards efficient photosynthesis: overexpression of *Zea mays* phosphoenolpyruvate carboxylase in *Arabidopsis thaliana*," Photosynth Res, 130:47-72, 26 pages.
Kasuga et al., (1999). "Improving plant drought, salt, and freezing tolerance by gene transfer of a single stress-inducible transcription factor," Nature Biotechnology, 17:287-291.
Kay et al., (1987). "Duplication of CaMV 35S Promoter Sequences Creates a Strong Enhancer for Plant Genes," Science, 236:1299-1302.
Kerstetter et al., (1994). "Sequence analysis and expression patterns divide the maize knotted1-like homeobox genes into two classes," Plant Cell, 6:1877-1887.
Kim et al., (1994). "Nuclear protein factors binding to a class I patatin promoter region are tuber-specific and sucrose-inducible," Plant Mol. Biol., 26:603-615.
Kirch et al., (1997). "Structural organization, expression and promoter activity of a cold-stress-inducible gene of potato (*Solanum tuberosum* L.)," Plant Mol. Biol., 33:897-909.
Klee et al., (1987). "Agrobacterium-Mediated Plant Transformation and its Further Applications to Plant Biology," Ann. Rev. of Plant Phys., 38:467-486.
Klein et al., (1987). "High-velocity microprojectiles for delivering nucleic acids into living cells," Nature, 327:70-73.
Kreutzweiser et al., (1994). "Toxicity of a new molt-inducing insecticide (RH-5992) to aquatic macroinvertebrates," Ecotoxicol. Environ. Safety, 28:14-24.
Krstic et al., (2012). "Chapter 13: Aluminum in Acid Soils: Chemistry, Toxicity and Impact on Maize Plants," Food Production—Approaches, Challenges and Tasks, pp. 231-242.
Kumagai et al., (1995). "Cytoplasmic inhibition of carotenoid biosynthesis with virus-derived RNA," PNAS USA, 92:1679-1683.
Lam et al., (1990). "GT-1 Binding Site Confers Light Responsive Expression in Transgenic Tobacco," Science, 248:471-474.
Lambers et al., (2006). "Root Structure and Functioning for Efficient Acquisition of Phosphorus: Matching Morphological and Physiological Traits," Annals of Botany, 98:693-713.
Larsen et al., (1996). "*Arabidopsis* Mutants with increased Sensitivity to Aluminum," Plant Physiol., 110:743-751.
Larsen et al., (1997). "Molecular and physiological analysis of *Arabidopsis* mutants exhibiting altered sensitivities to aluminum," Plant and Soil, 192:3-7.
Larsen et al., (1998). "Aluminum-Resistant *Arabidopsis* Mutants That Exhibit Altered Patterns of Aluminum Accumulation and Organic Acid Release from Roots," Plant Physiol., 117:9-18.
Li et al., (1996). "A novel myb-related gene from *Arabidopsis thaliana*," FEBS Lett., 379:117-121.
Li et al., (2013). "Multiplex and homologous recombination-mediated plant genome editing via guide RNA and Cas9," Nat. Biotechnol., 3(8):688-691, 8 pages.
Lincoln et al., (1994). "A knotted1-like homeobox gene in *Arabidopsis* is expressed in the vegetative meristem and dramatically alters leaf morphology when overexpressed in transgenic plants," Plant Cell, 6:1859-1876.

(56) References Cited

OTHER PUBLICATIONS

Liu et al., (1997). "A G-box-binding protein from soybean binds to the E1 auxin-response element in the soybean GH3 promoter and contains a proline-rich repression domain," Plant Physiol., 115:397-407.
Liu et al., (2017). "Application of CRISPR/Cas9 in plant biology," Acta Pharmaceutica Sinica B, 7(3):292-302.
Long et al., (1996). "A member of the Knotted class of homeodomain proteins encoded by the STM gene of *Arabidopsis*," Nature, 379:66-69.
Makarova et al., (2011). "Evolution and classification of the CRISPR-Cas systems," Nat. Rev. Microbial., 9(6):467-477, 23 pages.
Manjunath et al., (1997). "Molecular characterization and promoter analysis of the maize cytosolic glyceraldehyde 3-phosphate dehydrogenase gene family and its expression during anoxia," Plant Mol. Biol., 33:97-112.
Martin et al., (1997). "Identification of mutants in metabolically regulated gene expression," Plant J., 11(1):53-62.
Martinez et al., (1989). "Structure, evolution and anaerobic regulation of a nuclear gene encoding cytosolic glyceraldehyde-3-phosphate dehydrogenase from maize," J. Mol. Biol, 208:551-565.
Masgrau et al., (1997). "Inducible overexpression of oat arginine decarboxylase in transgenic tobacco plants," Plant J., 11(3):465-473.
Matsuoka et al., (1994). "The promoter of two carboxylases in a C4 plant (maize) direct cell-specific, light-regulated expression in a C3 plant (rice)," Plant J., 6(3):311-319.
McElroy et al., (1990). "Isolation of an efficient actin promoter for use in rice transformation," Plant Cell, 2:163-171.
McElroy et al., (1991). "Construction of expression vectors based on the rice actin 1 (Act1) 5' region for use in monocot transformation," Mol. Gen. Genet., 231:150-160.
Meier et al., (1997). "The tomato RBCS3A promoter requires integration into the chromatin for correct organ-specific regulation," FEBS Lett., 415(1):91-95.
Mett et al., (1993). "Copper-controllable gene expression system for whole plants," PNAS USA, 90:4567-4571.
Millar et al., (1996). "The alcohol dehydrogenase genes of cotton," Plant Mol. Biol., 31:897-904.
O'Leary et al., (2011). "The remarkable diversity of plant PEPC (phosphoenolpyruvate carboxylase): recent insights into the physiological functions and post-translational controls of non-photosynthetic PEPCs," Biochem J, 436:15-34.
Odell et al., (1985). "Identification of DNA sequences required for activity of the cauliflower mosaic virus 35S promoter," Nature, 313:810-812.
O'Grady et al., (1995). "Site-directed mutagenesis of the enhancer region of the 780 gene promoter of T-DNA," Plant Mol. Biol., 29:99-108.
Ortiz et al., (1996). "Hygromycin resistance as an efficient selectable marker for wheat stable transformation," Plant Cell Rep., 15:877-881.
Paszkowski et al., (1984). "Direct gene transfer to plants," EMBO J., 3(12):2717-2722.
Paulus et al., (2013). "Greater efficiency of photosynthetic carbon fixation due to single amino-acid substitution," Nature communications, 4:1518, 7 pages.
Röder et al., (1994). "Efficiency of the tetracycline-dependent gene expression system: complete suppression and efficient induction of the rolB phenotype in transgenic plants," Mol. Gen. Genet., 243:32-38.
Ryan et al., (2001). "Function and Mechanism of Organic Anion Exudation From Plant Roots," Annu Rev Plant Physiol Plant Mol Biol., 52:527-560.
Sade et al., (2016). "Toxicity and tolerance of aluminum in plants: tailoring plants to suit to acid soils," Biometals, 29(2):187-210.
Sakai et al., (1996). "Analysis of the promoter of the auxin-inducible gene, parC, of tobacco," Plant Cell Physiol, 37(7):906-913.
Sampson et al., (2013). "A CRISPR-Cas system mediates bacterial innate immune evasion and virulence," Nature, 497(7448):254-257, 13 pages.
Sanger et al., (1990). "Characteristics of a strong promoter from figwort mosaic virus: comparison with the analogous 35S promoter from cauliflower mosaic virus and the regulated mannopine synthase promoter," Plant Mol. Biol., 14:433-443.
Shan et al., (2013). "Targeted genome modification of crop plants using a CRISPR-Cas system," Nat. Biotechnol., 31(8):686-688.
Sheen, (1996). "Ca2+-dependent protein kinases and stress signal transduction in plants," Science, 274(5294):1900-1902, 3 pages.
Sheridan et al., (1996). "The Mac1 Gene: Controlling the Commitment to the Meiotic Pathway in Maize," Genetics, 142:1009-1020.
Shiina et al., (1997). "Identification of promoter elements involved in the cytosolic Ca(2+)-mediated photoregulation of maize cab-m1 expression," Plant Physiol., 115:477-483.
Sjödahl et al., (1995). "Deletion analysis of the *Brassica napus* cruciferin gene cru 1 promoter in transformed tobacco: promoter activity during early and late stages of embryogenesis is influenced by cis-acting elements in partially separate regions," Planta, 197:264-271.
Slocombe et al., (1994). "Temporal and Tissue-Specific Regulation of a *Brassica napus* Stearoyl-Acyl Carrier Protein Desaturase Gene," Plant Physiol., 104:1167-1176.
Stange et al., (1997). "Phosphorylation of nuclear proteins directs binding to salicylic acid-responsive elements," Plant J., 11(6):1315-1324.
Streit, (1997). "A biotin-regulated locus, bioS, in a possible survival operon of Rhizobium meliloti," Mol. Plant Microbe Interact., 10(7):933-937.
Sullivan et al., (2004). "Roots, Cycles and Leaves. Expression of the Phosphoenolpyruvate Carboxylase Kinase Gene Family in Soybean," Plant Physiol., 135:2078-2087.
Tair, (2003). "Germplasm: CS3852," available online at <https://www.arabidopsis.org/servlets/TairObject?id=1005161404&type=germplasm>, 1 page.
Takahashi et al., (1992). "Isolation and Analysis of the Expression of Two Genes for the 81-Kilodalton Heat-Shock Proteins from *Arabidopsis*," Plant Physiol., 99:383-390.
Thoma et al., (1994). "Tissue-Specific Expression of a Gene Encoding a Cell Wall-Localized Lipid Transfer Protein from *Arabidopsis*," Plant Physiol., 105(1):35-45.
Ueda et al., (1996). "Characterization and subcellular localization of a small GTP-binding protein (Ara-4) from *Arabidopsis*: conditional expression under control of the promoter of the gene for heat-shock protein HSP81-1," Mol. Gen. Genet., 250:533-539.
Uknes et al., (1993). "Regulation of pathogenesis-related protein-1a gene expression in tobacco," Plant Cell, 5:159-169.
Urao et al., (1996). "Molecular cloning and characterization of a gene that encodes a MYC-related protein in *Arabidopsis*," Plant Mol. Biol., 32:571-576.
Verdaguer et al., (1996). "Isolation and expression in transgenic tobacco and rice plants, of the cassava vein mosaic virus (CVMV) promoter," Plant Mol. Biol., 31:1129-1139.
Vilardell et al., (1991). "Regulation of the maize rab17 gene promoter in transgenic heterologous systems," Plant Mol. Biol., 17:985-993.
Vilardell et al., (1994). "Regulation of the rab17 gene promoter in transgenic *Arabidopsis* wild-type, ABA-deficient and ABA-insensitive mutants," Plant Mol. Biol., 24:561-569.
Vogg et al., (2004). "Tomato fruit cuticular waxes and their effects on transpiration barrier properties: functional characterization of a mutant deficient in a very-long-chain fatty acid beta-ketoacyl-CoA synthase," J. Exp Bot., 55(401):1401-1410.
Wang et al., (2016). "Genome-wide Analysis of Phosphoenolpyruvate Carboxylase Gene Family and Their Response to Abiotic Stresses in Soybean," Scientific Reports, 6:38448, 14 pages.
Wilde et al., (1992). "Control of gene expression in tobacco cells using a bacterial operator-repressor system," EMBO J., 11(4):1251-1259.
Yabe et al., (1994). "Analysis of tissue-specific expression of *Arabidopsis thaliana* HSP90-family gene HSP81," Plant Cell Physiol., 35(8):1207-1219.

(56) References Cited

OTHER PUBLICATIONS

Yamamoto et al., (1991). "Characterization of cis-acting sequences regulating root-specific gene expression in tobacco," Plant Cell, 3:371-382.

Yang et al., (2012). "Differential expression of genes involved in alternative glycolytic pathways, phosphorus scavenging and recycling in response to aluminum and phosphorus interactions in Citrus roots," Mol Biol Rep, 39:6353-6366.

Zhong et al., (1996). "The circadian clock gates expression of two *Arabidopsis catalase* genes to distinct and opposite circadian phases," Mol. Gen. Genet., 251:196-203.

Last et al., (1991). "pEmu: an improved promoter for gene expression in cereal cells," Theor Appl Genet, 81:581-588.

Abler et al., (1993). "Isolation and characterization of a genomic sequence encoding the maize Cat3 catalase gene," Plant Mol. Biol., 22:1031-1038.

Weising et al., (1988). "Foreign genes in plants: transfer, structure, expression, and applications," Annual review of genetics, 22(1):421-477.

\* cited by examiner

```
Maize        ---------------MPERHQSIDAQLRLLAPGKVSEDDKLVEYDALLVDRFLDILQDLHGPHL        49
Arabidopsis  ---------------MANRKLEKMASIDVHLRQLVFGKVSEDDKLVEYDALLLDRFLDILQDLHGEDL        53
Soybean      ---------------MGTRNFEKMASIDAQLRLLAPSKVSDDDKLVEYDALLLDRFLDILQDLHGDDI        53
Wheat        MALSAPGGGSGKIERLSSIDAQIRLLVPAKVSEDDKLIEYDALLLDRFLDVLQGLHGDDL              60
Barley       MALSAPGGGSGKIERLSSIDAQIRLLVPAKVSEDDKLIEYDALLLDRFLDVLQGLHGDDL              60
Rice         ---------MAGKVEKMASIDAQIRMLAPAKLSEDDKLVEYDALLLDRFLDILQDLHGDDL             52
Sorghum      ---------MAGKLEKMASIDAQIRMLAPAKLSEDDKLVEYDALLLDRFLDILQDLHGEDL             52
                            *:    *** .:.** *..:.:***:.**** **:******* ****  .:
Consensus    [XXXXX]XXEXXXSIDXXLRXLXPXKXSXDDKLXEYDALLXDRFLDXLHGXXX                    53

Maize        REEVQECYELSAEYENDRDEARLGELGSKLTSLPPGDSIVVASSFSHMLNLANLAEEVQI             109
Arabidopsis  RETVQELYEHSAEYEGKHEPKKIEELGSVLTSLDPGDSIVIAKAFSHMLNLANLAEEVQI             113
Soybean      RETVQDCYELSAEYEGQNNPQKIEELGNMLTGIDAGDSIVISKSFAHMLNLANLAEEVQI             113
Wheat        REMVQECYEVAAEYETKHDLEKIDELGEMITSLDPGDSIVIAKAFSHMLNLANLAEEVQI             120
Barley       REMVQECYEVAAEYETKHDLEKIDELGEMITSLDPGDSIVIAKAFSHMLNLANLAEEVQI             120
Rice         RELVQECYEIAAEYEGKHDSQKIDELGNMLTSLDPGDSIVMAKAFSHMLNLANLAEEVQI             112
Sorghum      RELVQECYEIAAEYERKHDSEKIDELGNMLTSLDPGDSIVTAKAFSHMLNLANLAEEVQI             112
             ** *** :** :***   . : :*.**. :* :*..***: :.*:::************
Consensus    REXVQXXYEXXAEYEXXXXXXXIXELTXXXTXLXXGDSIVXXXXFXHMLNLANLAEEVQI             113

Maize        AHRRRIKL-KRGDFADEASAPTESDIEETLKRIVSQLGKSREEVFDALKNQTVDLVFTAH             168
Arabidopsis  AYRRRIKKLKKGDFADFVDESSATTESDLEETFKKLVGDLNKSPEEIFDALKNQTVDLVLTAH           173
Soybean      AYRRRIKLLKKGDFADENSAITESDIEETFKRIVNQLKKTPQEIFDALKSQTVDLVLTAH             173
Wheat        AYRRRVKL-KKGDFADENSAITESDIEETLKRLVFDMKKSPAEVFDALKNQTVDLVLTAH             179
Barley       AYRRRVKL-KKGDFADENSAITESDIEETLKRLVFDMKKSPAEVFDALKNQTVDLVLTAH             179
Rice         AYRRRIKL-KKGDFADENSALTESDIEETFKRLVVDLKKSPAEVFDALKSQTVDLVLTAH             171
Sorghum      AYRRRIKL-KKGDFADENSALTESDIEETFKRLVVDLKKSPAEVFDALKSQTVDLVLTAH             171
             *:*** *: *  *.**  ..* ****:***:*::*  :*..* :********:******
Consensus    AXRRRIKLXKXGDFXDEXSAXTESDXEEEXXLVXXXXKXXXEXFDALKXQTVDLVLTAH             173
```

FIG. 5A

| | | |
|---|---|---|
| Maize | PTQSVRRSLLQKHGRIRNCLRQLYAKDITADDKQELDEALQREIQAAFRTDEIRRTPPTP | 228 |
| Arabidopsis | PTQSVRRSLLQKHGRIRDCLAQILYAKDITPDDKQELDEALQREIQAAFRTDEIKRTPPTP | 233 |
| Soybean | PTQSVRRSLLQKHGRIRNCLTQLYAKDITPDDKQELDEALQREIQAAFRTDEIRRTPPTP | 233 |
| Wheat | PTQSVRRSLLQKHSRIRNCLVQLYSKDITPDDKQELDEALQREIQAAFRTDEIRRLSPTP | 239 |
| Barley | PTQSVRRSLLQKHSRIRNCLVQLYSKDITPDDKQELDEALQREIQAAFRTDEIRRTQPTP | 239 |
| Rice | PTQSVRRSLLQKHSRIRNCLVQLYSKDITPDDKQELDEALQREIQAAFRTDEIRRTQPTP | 231 |
| Sorghum | PTQSVRRSLLQKHSRIRNCLVQLCSKDITPDDKQELDEALQREIQAAFRTDEIRRTQPTP | 231 |
| Consensus | PTQSVRRSLLQKHXRIRXCLXQLXXKDITXDDKQELDEALQREIQAAFRTDEIXRXXPTP | 233 |

| | | |
|---|---|---|
| Maize | QDEMRAGMSYFHETIWKGVPKFLRRIDTALKNIGTNERLPYNAPLIQFSSWMGGDRDGNP | 288 |
| Arabidopsis | QDEMRAGMSYFHETIWKGVPKFLRRVDTALKNIGIEERVPYNAPLIQFSSWMGGDRDGNP | 293 |
| Soybean | QDEMRAGMSYFHETIWKGTPKFLRRVDTALKNIGTNERVPYNAPVIQFSSWMGGDRDGNP | 293 |
| Wheat | QDHMRAGMSDFHETIWKGVPKFLRRVDTALKNIGINERVPYNAPLIQFSSWMGGDRDGNP | 299 |
| Barley | QDEMRAGMSYFHETIWKGVPKFLRRVDTALKNIGINERVPYNAPLIQFSSWMGGDRDGNP | 299 |
| Rice | QDEMRAGMSYFHETIWKGVPKFLRRLDTALKNIGIDERVPYNAPLIQFSSWMGGDRDGNP | 291 |
| Sorghum | QDEMRAGMSYFHETIWKGVPKFLRRVDTALKNIGIDERVPYNAPLIQFSSWMGGDRDGNP | 291 |
| Consensus | QDXMRAGMSXFHETIWKGXPKFLRRXDTALKNIGIXERXPYNAPXIQFSSWMGGDRDGNP | 293 |

| | | |
|---|---|---|
| Maize | RVTPEVTRDVCLLARMMAANLYFSQIEDLMFELSMWRCSDELRIRADELHRSSRKA-AKH | 347 |
| Arabidopsis | RVTPEVTRDVCLLARMMAATMYFNQIEDLMFEMSMWRCNDELRARADEVHANSRKDAAKH | 353 |
| Soybean | RVTPEVTRDVCLLARMMAANLYFSQIEDLMFELSMWRCNDELRVRSDELLSSSKRD-AKH | 352 |
| Wheat | RVTPEVTRDVCLLARMMAANLYCAQIEDLMFELSMWRCNDELRSRADELHRSSKKD-AKH | 358 |
| Barley | RVTPEVTRDVCLLARMMAANLYCAQIEDLMFELSMWRCNDELRARADELHRSSKKD-AKH | 358 |
| Rice | RVTPEVTRDVCLLARMMASNLYCSQIEDLMFELSMWRCNDELRARADELHLSSKKD-AKH | 350 |
| Sorghum | RVTPEVTRDVCLLARMMAANLYCSQIENLMFELSMWRCNDELRAQADELHRSSKKD-AKH | 350 |
| Consensus | RVTPEVTRDVCLLARMMAXXXXYXXQIEXLMFEXSMWRCXDELRXXXDEXXXXSXXXAKH | 353 |

FIG. 5B

```
Maize       YIEFWKQVPPNEPYRVILGDVRDKLYYTRERSRHLLTSGISEILEEATFTNVEQFLEPLE  407
Arabidopsis YIEFWKSIPTTEPYRVILGDVRDKLYHTRERAHQLLSNGHSDVPVEATFTNLEQFLEPLE  413
Soybean     YIEFWKQIPPNEPYRVILGDVRDKLYNTRERARQLLANGSSEIPEETTFTNVEQFLEPLE  412
Wheat       YIEFWKKVPPNEPYRVILGDVRDNLYNTRERSREILSSGHSDIPEEATLTNLEQLLEPLE  418
Barley      YIEFWKKVPPNEPYRVILGDVRDNLYNTRERSRELLSSGHSDIPEEATITNLEQLLEPLE  418
Rice        YIEFWKKVPPSEPYRVILGDVRDKLYNTRERARQLLSSGYSDIPEETTLISVEQFLEPLE  410
Sorghum     YIEFWKKVPPSEPYRVILGDLRDKLYNTRERARQLLSSGYSDIPEESTVTNVEQFLEPLE  410
            *****  .: . ********:****.:** ****:   . :   *.* .:*.*:****
Consensus   YIEFWKXXVXXEPYRVXLGDXRDXLYXTRERXXXLLXXGXSXXXEXTXXXXEQXLEPLE  413

Maize       LCYRSLCACGDKPIADGSLLDFLRQVSTFGLALVKLDIRQESDRHTDVLDSITTHLGIGS  467
Arabidopsis LCYRSLCSCGDRPIADGSLLDFLRQVSTFGLSLVRLDIRQESDRHTDVLDAITTHLDIGS  473
Soybean     LCYRSLCACGDQPIADGSLLDFLLDFLRQVSTFGLSLVRLDIRQESDRHTDVMDAITNHLEIGS  472
Wheat       LCYRSLCACGDRVIADGTLLDFTLLDFLRQVSTFGLSLVKLDIRQESDRHTDALDAITSYLGIGS  478
Barley      LCYRSLCACGDRVIADGTLLDFLLDFLRQVSTFGLSIVKLDIRQESDRHTDALDAITTYLGIGS  478
Rice        LCYRSLCDCGDRVIADGTLLDFLLDFLRQVSTFGICLVRLDIRQESDRHTDVLDAITTYLGIGS  470
Sorghum     LCYRSLCACGDRVIADGSLLDFLLDFLRQVSTFGICLVRLDIRQESDRHTDVLDAITTYLGIGS  470
            ******* ***  ****:****  *********. :*:************.:* :*  **
Consensus   LCYRSLCXCGDXXIADGXLLDFLRQVSTFGLXLVXLDIRQESDRHTDXXDXITXXLXIGS  473

Maize       YAEWSEEKRQDWLLSEIRGKRPLFGSDLPQTEETADVLGTFHVLAELPADCFGAYIISMA  527
Arabidopsis YREWSEERRQEWLLSELSGKRPLFGSDLPKTEEIADVLDTFHVIAELPADSFGAYIISMA  533
Soybean     YREWSEERRQEWLLSELSGKRPLFGPDLPKTEEIADVLETFHVIAELPSDSFGAYIISMA  532
Wheat       YREWSEEHRQEWLLSEINGKRPLFGADLPMTEEVADVMGAFQVIAELPGDNFGAYVISMA  538
Barley      YREWSEERRQEWLLSEINGKRPLFGADLPMTEEVADVMGAFQVIAELPGDNFGAYVISMA  538
Rice        YREWSEERRQDWLLSEINGKRPLFGPDLPKTDEIADVLDTFRVIAELPADNFGAYIISMA  530
Sorghum     YREWSEERRQEWLLSEINGKRPLFGPDLPTTDEIADVLDTFRVIAELPADNFGAYIISMA  530
            * ****::**:*****  ****** ***  :*:***: :*:*:****.*.****:****
Consensus   YXEWSEEXRQXWLLSELXGKRPLFGXDLPXTXEXADVXXXFXVXAELPXDXFGAYXISMA  533
```

FIG. 5C

```
Maize        TAPSDVLAVELLQRECHVKHPLRVVPLFEEKLADLEAAPAAVARLFSIDWYMDRINGKQEV  587
Arabidopsis  TAPSDVLAVELLQRECRVKQPLRVVPLFEEKLADLEAAPAAVARLFSVDWYKNRINGKQEV  593
Soybean      TAPSDVLSVELLQRECHVKQPLRVVPLFEEKLADLEAAPAAVARLFSIDWYRDRINGKQEV  592
Wheat        TSPSDVLAVELLQRECHIKTPLRVVPLFEEKLADLEAAPAALARLFSIDWYRERINGKQEV  598
Barley       TSPSDVLAVELLQRECHIKTPLRVVPLFEEKLADLEAAPAALARLFSIDWYRERINGKQEV  598
Rice         TAPSDVLAVELLQRECHVKTPLRVVPLFEEKLADLESAPAAVARLFSIDWYRERINGKQEV  590
Sorghum      TAPSDVLAVELLQRECHVKTPLRVVPLFEEKLADLEGAPAALARLFSVDWYRERINGKQEV  590
             *:****:*****:****  :*  ******* ****** :***::*:**:.***  ******
Consensus    TXPSDVLXVELLQRECXXKXPLRVVPLFEEKLADLEXAPAAXARLFSXDWYXXRINGKQEV  593

Maize        MIGYSDSGKDAGRLSAAWQMYKAQEELIKVAKHYGVKLTMFHGRGGTVGRGGGPTHLAIL  647
Arabidopsis  MIGYSDSGKDAGRLSAAWQLYKAQEELIVKAKEYGVKLTMFHGRGGTVGRGGGPTHLAIL  653
Soybean      MIGYSDSGKDAGRFSAAWALYKAQEELIKVAKEFGVKLTMFHGRGGTVGRGGGPTHLAIL  652
Wheat        MIGYSDSGKDAGRLSAAWQMYKAQEDLVKVAKQFGVKLTMFHGRGGTVGRGGGPTHLAIL  658
Barley       MIGYSDSGKDAGRLSAAWQMYKAQEDLVKVAKQFGVKLTMFHGRGGTVGRGGGPTHLAIL  658
Rice         MIGYSDSGKDAGRLSAAWQLYKSQEELINVAKEFGVKLTMFHGRGGTVGRGGGPTHLAIL  650
Sorghum      MIGYSDSGKDAGRLSAAWQLYKAQEELIKVAKKFGVKLTMFHGRGGTVGRGGGPTHLAIL  650
             *************.*****  **:**:**  :*:  *.**************************
Consensus    MIGYSDSGKDAGRXSAAWXXYKXQEXLXXVAKXXGVKLTMFHG&GGTVGRGGGPTHLAIL  653

Maize        SQPPDTIHGSLRVTVQGEVIEHSFGEELLCFRTLQRYTAATLEHGMHPPISPKPEWRALM  707
Arabidopsis  SQPPDTINGSLRVTVQGEVIEQSFGEEHLCFRTLQRFTAATLEHGMRPPISPKPEWRALL  713
Soybean      SQPPDTIHGSLRVTVQGEVIEQSFGEEHLCFRTLQRFTAATLEHGMRPPISPKPEWRALL  712
Wheat        SQPPDTINGSLRVTVQGEVIEQSFGEEHLCFRTLQRFTAATLEHGMHPPVAPKPEWRALM  718
Barley       SQPPDTINGSLRVTVQGEVIEQSFGEEHLCFRTLQRFTAATLEHGMRPPISPKPEWRALL  718
Rice         SQPPDTIHGSLRVTVQGEVIEQSFGEEHLCFRTLQRFTAATLEHGMRPPIAPKPEWRALL  710
Sorghum      SQPPDTIHGSLRVTVQGEVIEQSFGEEHLCFRTLQRFTAATLEHGMHPPISPKPEWRALL  710
             ********:*************:******:********:************:.*******:
Consensus    SQPPDTIXGSLRVTVQGEVIEXSF@EEXLCFRTLQRXTAATLEHGMXPPSSPKPEWRALX  713
```

FIG. 5D

```
Maize        DEMAVVATKEYRSIVFQEPRFVEYFRSATPETEYGRMNIGSRPSKRKPSGGIESLRAIPW  767
Arabidopsis  DEMAVVATEEYRSVVFQEPRFVEYFRLATPELEYGRMNIGSRPSKRKPSGGIESLRAIPW  773
Soybean      DEMAVIATEEYRSIVFQEPRFVEYFRCATPELEYGRMNIGSRPSKRKPSGGIESLRAIPW  772
Wheat        DEMAVVATEEYRSIVFQEPRFVEYFRLATPETEYGRMNIGSRPSKRKPSGGIESLRAIPW  778
Barley       DEMAVVATKEYRSIVFQEPRFVEYFRLATPETEYGRMNIGSRPSKRKPSGGIESLRAIPW  778
Rice         DEMAVVATKEYRSIVFQEPRFVEYFRLATPEMEYGRMNIGSRPSKRKPSGGIESLRAIPW  770
Sorghum      DEMAVVATKEYRSIVFQEPRFVEYFRLATPEMEYGRMNIGSRPSKRKPSGGIESLRAIPW  770
             ****:****:***.*********** ****:*********************** *****
Consensus    DEMAVXATXEYRSXVFQEPRFVEYFRXATPEXEYGRMNIGSRPSKRKPSGGIESLRAIPW  773

Maize        IFAWTQTRFFHLPVWLGFGAAIKHIMQKDIRNIHILREMYNEWPFFRVTLDLLEMVFAKGD  827
Arabidopsis  IFAWTQTRFHLPVWLGFGSAIRHVIEKDVRNLHMLQDMYQHWPFFRVTIDLIEMVFAKGD  833
Soybean      IFAWTQTRFHLPVWLGFGAAFSHVIKKDPKNLQMLQDMYNQWPFFRVSLDLVEMVFAKGD  832
Wheat        IFAWTQTRFHLPVWLGFGGAFKHILKKDIRNFHMLQEMYNEWPFFRVTIDLVEMVFAKGD  838
Barley       IFAWTQTRFHLPVWLGFGGAFKHILKKDIRNFHMLQEMYNEWPFFRVTIDLVEMVFAKGN  838
Rice         IFAWTQTRFHLPVWLGFGSAFKHTLEKDIRNLHMLQEMYNEWPFFRVTIDLVEMVFAKGD  830
Sorghum      IFAWTQTRFHLPVWLGFGAAFKHILEKDIRNLHMLQEMYNEWPFFRVTIDLVEMVFAKGD  830
             ********* ********.:: :*   *:::**  :******:*..:: ********:
Consensus    IFAWTQTRFHLPVWLGFGXAXXHXXXKDXXNXXXLXXMYXXWPFFRVXXDLXEMVFAXGX  833

Maize        PGIAAVYDKLIVADDLQSFGEQLRKNYEETKELLLQVAGHKDVLEGDPYLKQRLRLRESY  887
Arabidopsis  PGIAALYDKLIVSEELWPFGEKLRANFEETKKLILQTAGHKDLLEGDPYLKQRLRLRDSY  893
Soybean      PGIAALYDKLIVSEELWPFGERLRSMFEETKSLLLQVAGHKDLLEGDPYLKQRLRLRDSY  892
Wheat        PGIAALYDRLLVSEGLQPLGEKLRANYEETQKLLLQVAGHKDLLEGDPYLKQRLRLRDAY  898
Barley       PGIAALYDRLLVSEGLQPLGEKLRANYEETQKLLLQVAGHKDLLEGDPYLKQRLRLRDAY  898
Rice         PGIAALYDKLLVSEELWPLGEKLRANCEETKQLLLQVAGHKDLLEGDLYLKQRLRLRNAY  890
Sorghum      PGIAALYDKLLVSEELWPLGEKLRANYEETKRLLLQVAGHKDLLEGDLYLKQRLRLRDAY  890
             *****:**:*:*  .: :* ::* :. ****  *:*:*****::***:**********  :*
Consensus    PGIAAXYDXLLVXXXLXXXGEXLRXXXEETXXLLLQXAGHKDXLEGDXYLKQXLRLXXXY  893
```

FIG. 5E

| | | |
|---|---|---|
| Maize | ITTLNVCQAYTLKRIRDPSFQVSPQPPLSKEFTDESQPA-ELVQLNQQSEYAPGLEDTLI | 946 |
| Arabidopsis | ITTLNVCQAYTLKRIRDPSYHVTLRPHISKEIAESSKPAKELIELNPTSEYAPGLEDTLI | 953 |
| Soybean | ITTLNVLQAYTLKRIRDPDYHVKLRPHLSKDYMESNKPAAELVKLNPTSDYAPGLEDTLI | 952 |
| Wheat | ITTMNVCQAYTLKRIRDPDYHVALRPHLSKPAAELVTLNPASEYAPGLEDTLI | 958 |
| Barley | ITTMNVCQAYTLKRIRDPDYHVALRPHLSKEVMDTSKPAAELVTLNPASEYAPGLEDTLI | 958 |
| Rice | ITTLNVCQAYTMKRIRDPDYHVTLRPHMSKEIMDWSKPAAELVKLNPTSEYAPGLEDTLI | 950 |
| Sorghum | ITTLNVCQAYTMKRIRDPDYHVTLRPHLSKEIMDWNKPAAELVKLNPTSEYAPGLEDTLI | 950 |
| | \*\*\*:\*\* \*\*\*;\*\*\*\*\*\*.:;\* \* .:\*\*; \*\* \*:\*\*\*\*\*\*\*\*\* | |
| Consensus | ITTXNVXQAYTXKRIRDPXXXVXXSKXXXXXPAXELXXLNXXSXYAPGLEDTLI | 953 |

| | | |
|---|---|---|
| Maize | LTMKGIAAGMQNTG | 960 |
| Arabidopsis | LTMKGIAAGLQNTG | 967 |
| Soybean | LTMKGIAAGMQNTG | 966 |
| Wheat | LTMKGIAAGLQNTG | 972 |
| Barley | LTMKGIAAGLQNTG | 972 |
| Rice | LTMKGIAAGMQNTG | 964 |
| Sorghum | LTMKGIAAGMQNTG | 964 |
| | \*\*\*\*\*\*\*\*\*:\*\*\*\* | |
| Consensus | LTMKGIAAGXQ%TG | 967 |

FIG. 5E

ENGINEERED PHOSPHOENOLPYRUVATE CARBOXYLASE ENZYMES

CROSS-REFERENCE TO RELATED APPLICATIONS

This application is a national stage application under 35 U.S.C. § 371 of International Application No. PCT/US2020/27746, filed internationally on Apr. 10, 2020, which claims benefit of U.S. Provisional Application No. 62/832,727, filed Apr. 11, 2019, the disclosure of each of which is hereby incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 677032002700SEQLIST.TXT, date recorded: Oct. 4, 2021, size: 131,256 bytes).

TECHNICAL FIELD

The present disclosure provides plants that express a variant phosphoenolpyruvate carboxylase (PEPC) enzyme. The plants have enhanced resistance to aluminum than comparable plants that lack the variant PEPC enzyme. In addition, the plants more effectively sequester carbon, extract phosphate, and produce oxaloacetate-derived amino acids and glucose than comparable plants that lack the variant PEPC enzyme. The disclosure also provides tools for production of plants that express the variant PEPC enzyme.

BACKGROUND

Aluminum is considered to be a major limiting factor to crop growth in upwards of 50% of the world's arable land. A key approach for plants to adapt to aluminum toxic soils is to release aluminum chelating organic acids such as malate and citrate into the soil environment to chelate the aluminum to prevent it from being taken up into the root tissue. Prior work has found that increased release of malate and/or citrate into the rhizosphere increased the capability of plants to grow in aluminum toxic soils. This has been linked to increased capacity of plants to export these organic acids. However, attempts to engineer plants that have increased organic acid production have not been successful.

Accordingly, what is still needed in the art is another tool to increase aluminum resistance in plants. Also needed in the art are tools to increase organic acid release by plants into the soil so as to increase extraction of phosphate from the soil and to increase carbon sequestration in the soil. Further, tools for increasing production of oxaloacetate-derived amino acids and glucose by plants are desirable.

SUMMARY

The present disclosure provides plants that express a variant phosphoenolpyruvate carboxylase (PEPC) enzyme. The plants have enhanced resistance to aluminum than comparable plants that lack the variant PEPC enzyme. In addition, the plants more effectively sequester carbon, extract phosphate, and produce oxaloacetate-derived amino acids and glucose than comparable plants that lack the variant PEPC enzyme. The disclosure also provides tools for production of plants that express the variant PEPC enzyme.

BRIEF DESCRIPTION OF THE DRAWINGS

FIG. 5A-F shows an alignment of amino acid sequences of various C3 phosphoenolpyruvate carboxylase (PEPC) enzymes. PEPC amino acid sequences are also set forth as: maize (SEQ ID NO:2), *Arabidopsis* (SEQ ID NO:1), soybean (SEQ ID NO:3), wheat (SEQ ID NO:4), barley (SEQ ID NO:5), rice (SEQ ID NO:6), sorghum (SEQ ID NO:7), and a consensus (SEQ ID NO:8). Variant PEPC enzymes of the present disclosure comprise an amino acid substitution in at least one position indicated by "^" below the consensus sequence. A refined C3 PEPC consensus sequence is provided separately as SEQ ID NO:9.

DEFINITIONS

Figure 1:
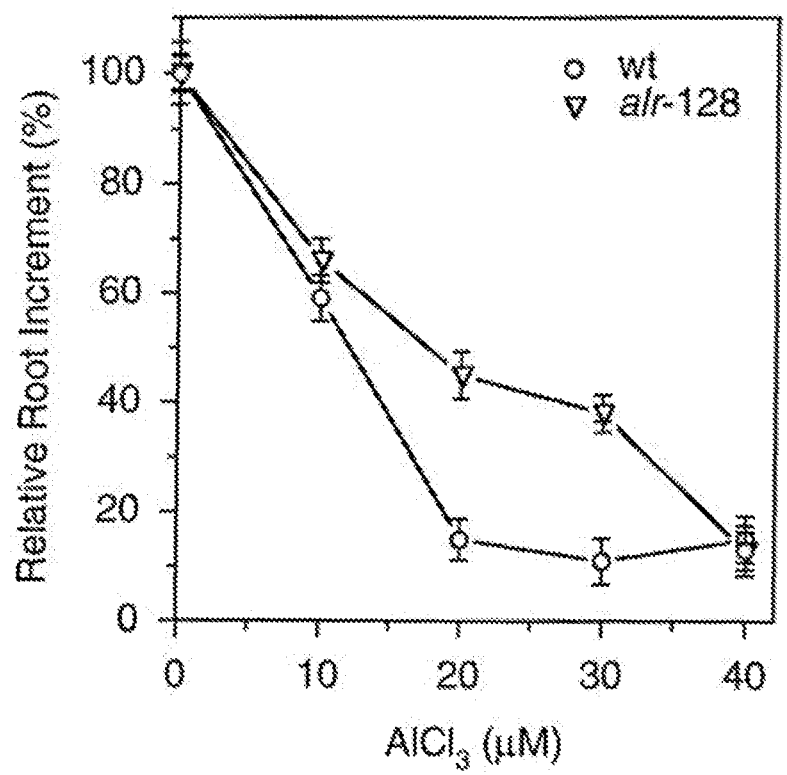
FIG. 1 shows the growth of *Arabidopsis thaliana* roots in hydroponic solution culture containing aluminum. Aluminum-dependent root growth inhibition was compared for wild type (wt) and mutant (alr-128) plants.

To facilitate an understanding of the embodiments disclosed herein, a number of terms and phrases are defined below. Terms and abbreviations not defined should be accorded their ordinary meaning as used in the art.

As used herein and in the appended claims, the singular forms "a," "an," and "the" include plural references unless indicated otherwise. For example, "a" cell includes one or more cells. Likewise, "an" amino acid substitution refers to "at least one" amino acid substitution.

The term "about" as used herein in reference to a value, encompasses from 90% to 110% of that value (e.g., a pH of about 5 refers to a pH of 4.5 to 5.5 and includes a pH of 5.0).

Numeric ranges are inclusive of the numbers defining the range (e.g., a pH of from 2 to 5 encompasses a pH of 2, 3, 4 and 5).

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting of" and "consisting essentially of" embodiments.

The term "isolated" means an object species (e.g., a nucleic acid) has been separated and/or recovered from components of its environment such that the object species is the predominant species present (i.e., on a molar basis it is more abundant than any other individual species in the composition). An "isolated" compound is at least 50% free, preferably at least 75% free, more preferably at least 90% free, and most preferably at least 95% free (e.g., 95%, 96%, 97%, 98%, or 99%) free from other compounds with which the compound of interest is typically associated.

As used herein, the term "phytotoxic substrate" refers to a growth substrate having a nanomolar or higher concentration of $Al^{3+}$ ions and an acidic pH of from about 2 to about 5. In some embodiments, the phytotoxic substrate is soil.

As used herein, the term "aluminum resistance" refers to the ability of a plant to withstand contact with a phytotoxic substrate. Plants with aluminum resistance may be able to continuously grow and survive despite toxic levels of aluminum in the soil. In some embodiments, a plant with aluminum resistance may show minor symptoms caused by aluminum toxicity, such as root stunting and reduced water and nutrient uptake, but is still able to grow or produce fruit despite the aluminum toxicity.

The term "enhanced aluminum resistance" refers to an increased ability of a subject plant to tolerate contact with a phytotoxic substrate as compared to a control plant (e.g., another plant of the same genus and/or species) subject to the same conditions. In some embodiments, the increased aluminum resistance can be observed as an at least 10%, 15%, 20%, or 35% increase in root growth of a subject plant as compared to a control plant when both are grown in a salt solution comprising 25 µM $AlCl_3$.

As used herein, the terms "enhancing" and "increasing" relative to a parameter of interest (e.g., phosphate extraction, carbon sequestration, production of oxaloacetate-derived amino acids and glucose, etc.) refer to enlarging the magnitude of the parameter. One of skill in the art readily understands that this is generally as compared to conditions (e.g., control) that are otherwise the same except for a property of interest (e.g., expression of a variant PEPC enzyme). Depending upon the parameter measured, increasing may be from 2-fold to 2000-fold or over, or from any of 2, 5, 10, 20, 40 or 80-fold to any of 100, 200, 400, 800, 1600 or 3,200-fold over the control condition.

As used herein, the terms "phosphoenolpyruvate carboxylase" and "PEPC" refer to an enzyme found in plants and some bacteria. PEPC catalyzes the addition of bicarbonate to phosphoenolpyruvate (PEP) to form oxaloacetate and inorganic phosphate. PEPC is classified as EC 4.1.1.31 and CAS Registry Number: 9067-77-0.

The term "variant" when used in connection with PEPC refers to a PEPC with an amino acid sequence that differs from a wild type PEPC sequence of the same genus or species (e.g., not 100% identical). Preferably the variant PEPC is classifiable as EC 4.1.1.31 and CAS Registry Number: 9067-77-0. More preferably, the variant PEPC is less susceptible to feedback inhibition and/or has faster reaction kinetics.

In the context of two or more sequences (e.g., nucleic acid sequences or amino acid sequences) the terms "identical" and "identify" refer to the percentage of residues in a subject sequence that are identical to residues in a reference sequence, after aligning the sequences and introducing gaps, if necessary, to achieve the maximum percent sequence identity. Conservative substitutions are not considered as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

DETAILED DESCRIPTION

I. Introduction

A previous mutagenesis approach using *Arabidopsis* as a model system resulted in several mutant plants that could grow robustly in an aluminum toxic environment (Larsen et al., Plant Physiol, 117:9-18, 1998). Although the phenotype of the mutants was assessed, the genotype of the mutants was not heretofore determined.

A key approach for plants to adapt to aluminum toxic soils and/or acidic soils (e.g., soils with a pH of 5 or lower; a pH of 5, 4.5, 4, 3.5, 3, 2.5, or 2) is to release aluminum-chelating organic acids, such as malate and citrate, into the soil environment to chelate the aluminum and prevent it from being taken up into the root tissue. An effort was made to identify the mutations that are responsible for the aluminum-resistance phenotype of *Arabidopsis thaliana* mutants alr-108, alr-128 and alr-139. A whole genome sequencing project was undertaken for alr-128 in which a genomic library from the mutant was generated and analyzed. This approach revealed a homozygous mutation in Atlg53310, in an amino acid that is strictly conserved amongst all phosphoenolpyruvate carboxylases (PEPCs) identified, but has no known role in PEPC function. Following this, Atlg53310 was sequenced for both alr-108 and alr-139, with each of these also having mutations that lead to amino acid substitutions in invariant or highly conserved positions in PEPCs in general.

Phosphoenolpyruvate carboxylase (PEPC) is an enzyme that is key to production of oxaloacetate as a means to replenish the tricarboxylic acid (TCA) cycle in plants. PEPC has a similar role to pyruvate carboxylase in animals, both of which are responsible for generating oxaloacetate for replenishing TCA cycle intermediates that are removed for processes such as amino acid production or fatty acid biosynthesis. Work has been performed to try to link PEPC overexpression to increases in aluminum resistance, but wild-type PEPC overexpression alone has resulted in only marginal increases in aluminum resistance.

Two isoforms of PEPC are C3 PEPC and C4 PEPC. The C3 PEPC is the key enzyme in the classical C3 non-photosynthetic pathway, which is the main form of PEPC in plants. The C3 PEPC has a malate binding site that serves to allosterically control C3 PEPC activity by malate feedback inhibition. In general, the PEPC present in the roots of plants is the C3 PEPC. In contrast, the C4 PEPC, which is strictly linked to C4 photosynthesis in shoots of a limited number of plant species, has reduced malate-dependent feedback and thus, is less affected allosterically by malate. In SEQ ID NO:2 (maize C3 PEPC): i) A at position 770 is a hallmark for C3 and would be S if C4; and ii) R at position 880 is a hallmark for C3 and would be G if C4. In SEQ ID NO:15 (maize C4 PEPC): i) S at position 780 is a hallmark for C4 and would be A if C3; and ii) G at position 890 is a hallmark for C4 and would be R if C3. Positions 770 and 880 of maize C3 PEPC and positions 780 and 890 of maize C4 PEPC correspond to positions 776 and 886 respectively in the consensus sequence of SEQ ID NO:8.

The present disclosure provides compositions and methods that modify the function and behavior of PEPC in roots to enhance aluminum resistance in plants. As described further herein, increasing PEPC activity in roots confers increased malate production in plants and consequently, provides aluminum resistance. The present disclosure further provides compositions and methods that modify the function and behavior of PEPC in other plant parts to enhance photosynthesis in plants. As described further herein, increasing PEPC activity in above-ground plant parts confers increased glucose production in plants.

Additionally, a number of genes have been found to be differentially expressed in citrus plants grown in the presence of a high level of aluminum and a low level of phosphorus (Yang et al., Mol Biol Rep, 39:6353-6366, 2012). More recently, phosphoenolpyruvate carboxylase (PEPC) expression was found to be induced in soybeans subjected to various abiotic stresses (Wang et al., Scientific Reports, 6:38448, 2016). However, prior to development of the present disclosure, variant root PEPC enzymes conferring aluminum-resistance had not been identified.

II. Variant Phosphoenolpyruvate Carboxylase (PEPC)

Increasing the production of aluminum-chelating organic acids, such as malate, in a plant may enhance the plant's aluminum resistance. Since phosphoenolpyruvate carboxylase (PEPC) in plants catalyzes the addition of bicarbonate to phosphoenolpyruvate (PEP) to form oxaloacetate, which is a precursor of malate, improved PEPC activity is likely to increase oxaloacetate production resulting in increased malate levels. Improving the activity of PEPC, which is present in the roots of plants, may be particularly beneficial to enhancing aluminum resistance in plants, especially in plants grown in soil with a high aluminum concentration and/or an acidic pH (e.g., soils with a micromolar or higher levels of $Al^{3+}$ and/or pH from 2-5).

Accordingly, in one aspect, the present disclosure provides a variant phosphoenolpyruvate carboxylase (PEPC) having improved activity such that its expression in a plant leads to increased production of oxaloacetate and malate, which in turn results in enhanced aluminum resistance in the plant. The improved activity of the variant PEPC may be achieved by reducing the enzyme's sensitivity to allosteric feedback inhibition by malate and/or by increasing the enzyme's active site activity.

Accordingly, the variant PEPC of the present disclosure may contain one or more amino acid substitutions that are conducive to improved PEPC activity. Some preferred and alternative substitutions are listed in Table I. Throughout the present disclosure and unless indicated to the contrary, amino acid positions are numbered relative to SEQ ID NO:8 as determined when the amino acid sequence of a PEPC enzyme of interest is aligned to SEQ ID NO:8 using a pairwise alignment algorithm. For instance, the amino acid sequence of wild type Zea mays PPC1 has serine (S) at position 780 and glycine (G) at position 890 (SEQ ID NO:15), which corresponds to positions 776 and 886, respectively in the consensus sequence (SEQ ID NO:8). The numbering of the refined consensus sequence of SEQ ID NO:9 is equivalent to the consensus sequence of SEQ ID NO:8. Thus, amino acid positions numbered relative to SEQ ID NO:8 are also numbered relative to SEQ ID NO:9.

Table I

| Favored Substitutions | | |
|---|---|---|
| Original Residue | Preferred Substitutions | Other Substitutions |
| Arg637 (R637) | Gly (G) or Ala (A) or Val (V) | Ile (I) or Leu (L) or Met (M) |
| Ala651 (A651) | Val (V) or Ile (I) or Leu (L) | Met (M) or Ser (S) or Thr (T) |
| Gln675 (Q675) | Gly (G) or Ala (A) or Val (V) | Ile (I) or Leu (L) or Met (M) |
| Gly678 (G678) | Ser (S) or Thr (T) | Val (V) or Ile (I) or Leu (L) |
| Ala776 (A776) | Ser (S) or Thr (T) | Val (V) or Ile (I) or Leu (L) |
| Thr778 (T778) | Ile (I) or Leu (L) or Met (M) | Gly (G) or Ala (A) or Val (V) |
| Lys831 (K831) | Gly (G) or Ala (A) or Val (V) | Ile (I) or Leu (L) or Met (M) |
| Arg886 (R886) | Gly (G) or Ala (A) or Val (V) | Ile (I) or Leu (L) or Met (M) |
| Arg890 (R890) | Gly (G) or Ala (A) or Val (V) | Ile (I) or Leu (L) or Met (M) |
| Asn965 (N965) | Gly (G) or Ala (A) or Val (V) | Ile (I) or Leu (L) or Met (M) |

C3 PEPC activity is strictly controlled by the allosteric regulator malate, which when accumulated to high levels, results in strong inhibition of PEPC activity in roots. There are several amino acids that are directly involved in malate binding at the allosteric pocket of PEPC. In some embodiments, the present disclosure provides compositions and methods for increasing PEPC activity by reducing the enzyme's sensitivity to feedback inhibition by malate. Arabidopsis thaliana mutants alr-108 and alr-128, which contain amino acid substitutions A651V and G678S, respectively, relative to the sequence of SEQ ID NO:1, are both thought to alter how the malate binding site communicates with the active site of PEPC. The malate binding site of PEPC also includes several positively charged amino acids (e.g., Arg and Lys) that function to bind the negatively charged malate. These positively charge amino acids may be changed to alter the association of malate in the malate binding site and consequently, relieve the feedback inhibition of PEPC activity by malate.

In some embodiments, one or more positively charged amino acids in the malate binding site of PEPC may be substituted with an uncharged or negatively charged amino acid (e.g., Ala, Gly, Val, Leu, Ile, Met, Asp, or Glu), to reduce malate binding and consequently to reduce the sensitivity of the PEPC to feedback inhibition by malate. In some embodiments, amino acids in the malate binding site of PEPC that may be mutated to reduce the sensitivity of PEPC to feedback inhibition by malate include, but are not limited to, R637, A651, Q675, G678, K831, R886, R890, and N965, relative to the sequence of SEQ ID NO:1. In some embodiments, uncharged or negatively charged amino acids (e.g., Ala, Gly, Val, Leu, Ile, Met, Asp, or Glu) may be present in one or more positions selected from 637, 651, 675, 678, 831, 886, 890 or 965. In certain embodiments, amino acid substitutions in PEPC that may reduce the sensitivity of PEPC to feedback inhibition by malate include, but are not limited to, A651V, G678S, and R886G.

PEPC may also be engineered to increase oxaloacetate production by increasing the enzyme's active site activity. The active site of the PEPC may be modified to improve the kinetics of the enzyme (e.g., increasing the binding affinity of the enzyme to its substrate phosphoenolpyruvate, and/or increasing other aspects of the catalytic efficacy of the enzyme such as its reaction rate). As described in Example 1, *A. thaliana* mutant alr-139 contains amino acid substitution T778I, relative to the sequence of SEQ ID NO:1, the position of which maps to the active site of PEPC.

In some embodiments, one or more amino acids in the active site of PEPC may be altered to increase PEPC activity. In some embodiments, one or more polar amino acids (e.g., Thr, Ser, Cys, Asn, and Gln) in the active site of PEPC may be substituted with a nonpolar amino acid (e.g., Gly, Ala, Val, Leu, Met, and Ile). In certain embodiments, amino acid substitutions that may increase enzymatic activity of PEPC include but are not limited to T778I and/or A776S, relative to the sequence of SEQ ID NO:1.

In some embodiments, the variant phosphoenolpyruvate carboxylase (PEPC) comprises at least one amino acid substitution at a position corresponding to one or more of residues A651, G678, A776, T778, and R886, in the consensus sequence of SEQ ID NO:8, where the amino acid sequence of the variant is at least 90%, 91%, 92%, 93%, 94% 95%, 96%, 97%, 98%, or 99% identical to the consensus sequence of SEQ ID NO:8, and where the amino acid sequence of the variant does not consist of SEQ ID NO:10, SEQ ID NO:11, or SEQ ID NO:12. In some embodiments, the variant PEPC comprises at least one further amino acid substitution at a position corresponding to one or more of residues R637, X675, K831, R890 and N965 in the consensus sequence of SEQ ID NO:8, where X675 is Q675 or H675. In some embodiments, the variant PEPC comprises at least one amino acid substitution at a position corresponding to one or more of residues A651, G678, and T778 in the consensus sequence of SEQ ID NO:8. In some embodiments, the variant PEPC further comprises an amino acid substitution at a position corresponding to one or both of A776 and R886 in the consensus sequence of SEQ ID NO:8. In some embodiments, the variant PEPC comprises one or more amino acid substitutions selected from the group consisting of A651V, G678S, A776S, T778I, and R886G. In some embodiments, the variant PEPC comprises one or more amino acid substitutions selected from the group consisting of A651V, G678S, and T778I. In some embodiments, the variant PEPC further comprises an amino acid substitution selected from the group consisting of one or both of A776S and R886G. In some embodiments, the amino acid sequence of the variant is at least 99% identical to SEQ ID NO:9.

Two PEPC sequences are substantially identical if their amino acid sequences have at least 50% identity (e.g., at least 50%, 55%, 60%, 65%, 70%, 75%, 80%, 85%, 90%, 95%, 99% or 100% identity over a specified region, or, when not specified, over their entire sequences), when compared and aligned for maximum correspondence over a comparison window or designated region. As pertains to the present disclosure and claims, the BLASTP sequence comparison algorithm using default parameters is used align amino acid sequences for determination of sequence identity.

Algorithms that are suitable for determining percent sequence identity and sequence similarity are the BLAST and BLAST 2.0 algorithms, described in Altschul et al., *J Mol Biol*, 215: 403-410, 1990; and Altschul et al., *Nucleic Acids Res*. 25: 3389-3402, 1977, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

III. Nucleic Acids and Expression Cassettes

Nucleic Acids

In some embodiments, the present disclosure is related to a nucleic acid encoding a variant phosphoenolpyruvate carboxylase (PEPC) of any one of the preceding embodiments. In some embodiments, the present disclosure is related to an isolated nucleic acid encoding a variant phosphoenolpyruvate carboxylase (PEPC) comprising at least one amino acid substitution at a position corresponding to one or more of residues A651, G678, A776, T778, and R886, in the consensus sequence of SEQ ID NO:8, where the amino acid sequence of the variant is at least 95% identical to the consensus sequence of SEQ ID NO:8, and where the amino acid sequence of the variant does not consist of SEQ ID NO:10, SEQ ID NO:11, or SEQ ID NO:12. The nucleic acid encoding a variant PEPC of the present disclosure may be of any nucleic acid type, including RNA, such as messenger RNA (mRNA), and DNA, such as complementary DNA (cDNA), genomic DNA (gDNA), and synthetic DNA.

In another aspect, the present disclosure provides an expression cassette comprising a promoter operably linked to a nucleic acid encoding a variant PEPC of any of the preceding embodiments. As used herein, an "expression cassette" refers to a nucleic acid construct that, when introduced into a host cell, results in transcription and/or translation of an RNA or polypeptide, respectively.

In some embodiments, the expression cassette of the present disclosure comprises a promoter operably linked to the nucleic acid encoding the variant PEPC. The promoter may be heterologous to the nucleic acid. In some embodiments, the promoter may be inducible. In some embodiments, the promoter may plant tissue-specific (e.g., phloem-specific, tuber-specific, root-specific, stem-specific, trunk-specific, or leaf-specific).

Any promoters well known in the art may be used to drive the expression of a variant PEPC in plants. Any organ may be targeted, such as shoot vegetative organs/structures (e.g. leaves, stems, and tubers), roots, flowers and floral organs/structures (e.g. bracts, sepals, petals, stamens, carpels, anthers and ovules), seed (including embryo, endosperm, and seed coat) and fruit. Alternatively, the nucleic acid encoding a variant PEPC described herein may be expressed specifically in certain cell and/or tissue types within one or more organs (e.g., guard cells in leaves using a guard cell-specific promoter). Alternatively, the nucleic acid encoding a variant PEPC described herein may be expressed constitutively (e.g., using the CaMV 35S promoter).

To use a nucleic acid encoding a variant PEPC described herein in the above techniques, recombinant DNA vectors suitable for transformation of plant cells may be prepared. Techniques for transforming a wide variety of higher plant species are well described in the technical and scientific literature (see, e.g., Weising et al., Ann. Rev. Genet. 22:421-477, 1988). A DNA sequence coding for the variant PEPC preferably may be combined with transcriptional and translational initiation regulatory sequences that direct the transcription of the sequence from the gene in the intended tissues of the transformed plant.

For example, a plant promoter fragment may be employed to direct expression of the variant PEPC in all tissues of a transgenic plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the variant PEPC in a specific tissue (tissue-specific promoters) or may be otherwise under more precise environmental control (inducible promoters). Examples of tissue-specific promoters under developmental control include promoters that initiate transcription only in certain tissues, such as roots, phloem, tubers, stems, trunks, leaves, or guard cells. In particular embodiments, a plant promoter may be employed to direct expression of the variant PEPC in root tissues of a plant. Examples of environmental conditions that may affect transcription by inducible promoters include, but are not limited to, anaerobic conditions, elevated temperature, elevated toxic metal concentration in soil such as aluminum, and presence of light.

In some embodiments, the promoter is heterologous to the nucleic acid encoding the variant PEPC of the present disclosure. As used herein, a "heterologous" promoter refers to a promoter is from a different origin than the nucleic acid encoding the variant PEPC. Thus, a promoter that has been isolated from an organism different from that of the nucleic acid encoding the variant PEPC is considered heterologous with respect to the nucleic acid encoding the variant PEPC; a promoter that has been isolated from a gene that is different from that of the nucleic acid encoding the variant PEPC is also considered heterologous with respect to the nucleic acid encoding the variant PEPC.

Constitutive Promoters

In some embodiments, the expression cassette of the present disclosure comprises a constitutive promoter directing expression of the nucleic acid encoding the variant PEPC in all transformed cells or tissues, e.g., as those of a transgenic plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., Nature 313:810-812 (1985)). The CaMV 35S promoter can be particularly useful due to its activity in numerous diverse plant species (Benfey and Chua, Science 250:959-966 (1990); Futterer et al., Physiol. Plant 79:154 (1990); Odell et al., supra, 1985). A tandem 35S promoter, in which the intrinsic promoter element has been duplicated, confers higher expression levels in comparison to the unmodified 35S promoter (Kay et al., Science 236:1299 (1987)). Other useful constitutive regulatory elements include, for example, the cauliflower mosaic virus 19S promoter; the Figwort mosaic virus promoter; and the nopaline synthase (nos) gene promoter (Singer et al., Plant Mol. Biol. 14:433 (1990); An, Plant Physiol. 81:86 (1986)).

Additional constitutive regulatory elements including those for efficient expression in monocots also are known in the art, for example, the pEmu promoter and promoters based on the rice Actin-1 5' region (Last et al., Theor. Appl. Genet. 81:581 (1991); Mcelroy et al., Mol. Gen. Genet. 231:150 (1991); Mcelroy et al., Plant Cell 2:163 (1990)). Chimeric regulatory elements, which combine elements from different genes, also can be useful for ectopically expressing a nucleic acid molecule encoding a variant PEPC described herein (Comai et al., Plant Mol. Biol. 15:373 (1990)).

Other examples of constitutive promoters include the 1'- or 2'-promoter derived from T-DNA of *Agrobacterium tumafaciens* (see, e.g., Mengiste (1997) supra; O'Grady (1995) Plant Mol. Biol. 29:99-108); actin promoters, such as the *Arabidopsis* actin gene promoter (see, e.g., Huang (1997) Plant Mol. Biol. 1997 33:125-139); alcohol dehydrogenase (Adh) gene promoters (see, e.g., Millar (1996) Plant Mol. Biol. 31:897-904); ACT11 from *Arabidopsis* (Huang et al.

Plant Mol. Biol. 33:125-139 (1996)), Cat3 from *Arabidopsis* (GenBank No. U43147, Zhong et al., Mol. Gen. Genet. 251:196-203 (1996)), the gene encoding stearoyl-acyl carrier protein desaturase from *Brassica napus* (Genbank No. X74782, Solocombe et al. Plant Physiol. 104:1167-1176 (1994)), GPc1 from maize (GenBank No. X15596, Martinez et al. J. Mol. Biol 208:551-565 (1989)), Gpc2 from maize (GenBank No. U45855, Manjunath et al., Plant Mol. Biol. 33:97-112 (1997)), other transcription initiation regions from various plant genes known to those of skill. See also Holtorf Plant Mol. Biol. 29:637-646 (1995).

Inducible Promoters

In some embodiments, the expression cassette of the present disclosure comprises an inducible promoter directing expression of the nucleic acid encoding the variant PEPC under the influence of changing environmental conditions or developmental conditions. Examples of environmental conditions that may affect transcription by inducible promoters include anaerobic conditions, elevated temperature, drought, toxic metals and/or the presence of light. Such promoters are referred to herein as "inducible" promoters. In some embodiments, an inducible promoter is one that is induced by one or more environmental stressors, including but not limited to, drought, freezing cold, toxic metals, and high salt. For example, the disclosure can incorporate a drought-specific promoter such as a drought-inducible promoter of maize (e.g., the maize rab17 drought-inducible promoter (Vilardell et al. (1991) Plant Mol. Biol. 17:985-993; Vilardell et al. (1994) Plant Mol. Biol. 24:561-569)); or alternatively a cold, drought, and high salt inducible promoter from potato (Kirch (1997) Plant Mol. Biol. 33:897-909) or from *Arabidopsis* (e.g., the rd29A promoter (Kasuga et al. (1999) Nature Biotechnology 17:287-291). Other environmental stress-inducible promoters include promoters from the following genes: Rab21, Wsi18, Lea3, Uge1, Dip1, and R1G1B in rice (Yi et al. (2010) Planta 232:743-754).

In some embodiments, the inducible promoter is a stress-inducible promoter (e.g., a drought-, cold-, or salt-inducible promoter) that comprises a dehydration-responsive element (DRE) and/or an ABA-responsive element (ABRE), including but not limited to the rd29A promoter.

Alternatively, plant promoters that are inducible upon exposure to plant hormones, such as auxins, are used to express the nucleic acid encoding the variant PEPC. For example, the disclosure can use the auxin-response elements E1 promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (Sheen (1996) Science 274:1900-1902).

Plant promoters inducible upon exposure to chemical reagents that may be applied to the plant, such as herbicides or antibiotics, are also useful for expressing the nucleic acid encoding the variant PEPC. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. A variant PEPC coding sequence can also be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324; Uknes et al., Plant Cell 5:159-169 (1993); Bi et al., Plant J. 8:235-245 (1995)).

Examples of useful inducible regulatory elements include copper-inducible regulatory elements (Mett et al., Proc. Natl. Acad. Sci. USA 90:4567-4571 (1993); Furst et al., Cell 55:705-717 (1988)); tetracycline and chlor-tetracycline-inducible regulatory elements (Gatz et al., Plant J. 2:397-404 (1992); Roder et al., Mol. Gen. Genet. 243:32-38 (1994); Gatz, Meth. Cell Biol. 50:411-424 (1995)); ecdysone inducible regulatory elements (Christopherson et al., Proc. Natl. Acad. Sci. USA 89:6314-6318 (1992); Kreutzweiser et al., Ecotoxicol. Environ. Safety 28:14-24 (1994)); heat shock inducible regulatory elements (Takahashi et al., Plant Physiol. 99:383-390 (1992); Yabe et al., Plant Cell Physiol. 35:1207-1219 (1994); Ueda et al., Mol. Gen. Genet. 250: 533-539 (1996)); and lac operon elements, which are used in combination with a constitutively expressed lac repressor to confer, for example, IPTG-inducible expression (Wilde et al., EMBO J. 11:1251-1259 (1992)). An inducible regulatory element useful in the transgenic plants of the present disclosure also can be, for example, a nitrate-inducible promoter derived from the spinach nitrite reductase gene (Back et al., Plant Mol. Biol. 17:9 (1991)) or a light-inducible promoter, such as that associated with the small subunit of RuBP carboxylase or the LHCP gene families (Feinbaum et al., Mol. Gen. Genet. 226:449 (1991); Lam and Chua, Science 248:471 (1990)).

Tissue-Specific Promoters

In some embodiments, the expression cassette of the present disclosure comprises a tissue-specific promoter directing expression of the nucleic acid encoding the variant PEPC in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistols, flowers, or any embryonic tissue, or epidermis or mesophyll. Reproductive tissue-specific promoters may be, e.g., ovule-specific, embryo-specific, endosperm-specific, integument-specific, seed and seed coat-specific, pollen-specific, petal-specific, sepal-specific, or some combination thereof. In some embodiments, the promoter is cell-type specific (e.g., guard cell-specific, bundle sheath cell-specific, etc.). In particular embodiments, the promoter may direct expression of the nucleic acid encoding the variant PEPC in a root tissue of the plant.

Epidermal-specific promoters include, for example, the *Arabidopsis* LTP1 promoter (Thoma et al. (1994) Plant Physiol. 105(1):35-45), the CER1 promoter (Aarts et al. (1995) Plant Cell 7:2115-27), and the CER6 promoter (Hooker et al. (2002) Plant Physiol 129:1568-80), and the orthologous tomato LeCER6 (Vogg et al. (2004) J. Exp Bot. 55:1401-10).

Guard cell-specific promoters include, for example, the DGP1 promoter (Li et al. (2005) Science China C Life Sci. 48:181-186).

Other tissue-specific promoters include seed promoters. Suitable seed-specific promoters are derived from the following genes: MAC1 from maize (Sheridan (1996) Genetics 142:1009-1020); Cat3 from maize (GenBank No. L05934, Abler (1993) Plant Mol. Biol. 22:10131-1038); vivparous-1 from *Arabidopsis* (Genbank No. U93215); atmyc1 from *Arabidopsis* (Urao (1996) Plant Mol. Biol. 32:571-57; Conceicao (1994) Plant 5:493-505); napA from *Brassica napus* (GenBank No. J02798, Josefsson (1987) JBL 26:12196-1301); and the napin gene family from *Brassica napus* (Sjodahl (1995) Planta 197:264-271).

A variety of promoters specifically active in vegetative tissues, such as leaves, stems, roots and tubers, can also be used to express nucleic acid encoding a variant PEPC described herein. For example, promoters controlling patatin, the major storage protein of the potato tuber, can be used, see, e.g., Kim (1994) Plant Mol. Biol. 26:603-615; Martin (1997) Plant J. 11:53-62. The ORF13 promoter from *Agrobacterium rhizogenes* that exhibits high activity in roots can also be used (Hansen (1997) Mol. Gen. Genet. 254:337-343. Other useful vegetative tissue-specific promoters include: the tarin promoter of the gene encoding a globulin from a major taro (*Colocasia esculenta* L. Schott) corm protein family, tarin (Bezerra (1995) Plant Mol. Biol. 28:137-144); the curculin promoter active during taro corm development (de Castro (1992) Plant Cell 4:1549-1559) and the promoter for the tobacco root-specific gene TobRB7, whose expression is localized to root meristem and immature central cylinder regions (Yamamoto (1991) Plant Cell 3:371-382).

Leaf-specific promoters, such as the ribulose biphosphate carboxylase (RBCS) promoters, can also be used. For example, the tomato RBCS1, RBCS2 and RBCS3A genes are expressed in leaves and light-grown seedlings, only RBCS1 and RBCS2 are expressed in developing tomato fruits (Meier (1997) FEBS Lett. 415:91-95). A ribulose bisphosphate carboxylase promoters expressed almost exclusively in mesophyll cells in leaf blades and leaf sheaths at high levels, described by Matsuoka (1994) Plant J. 6:311-319, can be used. Another leaf-specific promoter is the light harvesting chlorophyll a/b binding protein gene promoter, see, e.g., Shiina (1997) Plant Physiol. 115:477-483; Casal (1998) Plant Physiol. 116:1533-1538. The *Arabidopsis thaliana* myb-related gene promoter (Atmyb5) described by Li (1996) FEBS Lett. 379:117-121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) Plant J. 11:1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) Cell 86:423-433; and, Long (1996) Nature 379:66-69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) Plant Cell. 7:517-527). Also useful are kn1-related genes from maize and other species which show meristem-specific expression, see, e.g., Granger (1996) Plant Mol. Biol. 31:373-378; Kerstetter (1994) Plant Cell 6:1877-1887; Hake (1995) Philos. Trans. R. Soc. Lond. B. Biol. Sci. 350:45-51. For example, the *Arabidopsis thaliana* KNAT1 promoter (see, e.g., Lincoln (1994) Plant Cell 6:1859-1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, the nucleic acid encoding the variant PEPC is expressed through a transposable element. This allows for constitutive, yet periodic and infrequent expression of the constitutively active polypeptide. The disclosure also provides for use of tissue-specific promoters derived from viruses including, e.g., the tobamovirus subgenomic promoter (Kumagai (1995) Proc. Natl. Acad. Sci. USA 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) Plant Mol. Biol. 31:1129-1139).

Expression Vectors

In some embodiments, the present disclosure provides for expression vectors comprising an expression cassette of any one of the preceding embodiments. As used herein, an "expression vector" refers to a vector comprising a recombinant nucleic acid comprising expression control sequences operatively linked to a nucleic acid to be expressed. An expression vector comprises sufficient cis-acting elements for expression; other elements for expression may be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. In some embodiments, the expression vector is a plasmid.

Host Cells

In some embodiments, the present disclosure provides host cells comprising an expression cassette of any one of the preceding embodiments. The host cell may be of any type of cell. In some embodiments, the host cell is prokaryotic or eukaryotic. In some embodiments, the host cell is a bacterial cell, a yeast cell, a mammalian cell, or a plant cell. In some particular embodiments, the host cell is a plant cell.

Transgenic Plants

In other aspects, transgenic plants containing a host cell of the present disclosure are provided. As used herein, a "transgenic plant" refers to a plant that has incorporated a heterologous or exogenous nucleic acid, i.e., a nucleotide sequence that is not present in the native (non-transgenic or "untransformed") plant or plant cell. "Transgenic" is used herein to include any cell, cell line, callus, tissue, plant part or plant, the genotype of which has been altered by the presence of heterologous nucleotide sequence including those transgenics initially so altered as well as those created by sexual crosses or asexual propagation from the initial transgenic plant. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation. In some embodiments, a transgenic plant is generated that contains a complete or partial sequence of a nucleic acid that is derived from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome. In some embodiments, the transgenic plant expresses the variant PEPC. In some embodiments, the transgenic plant has enhanced aluminum resistance as compared to a control plant of the same species that does not express the variant PEPC.

IV. Methods of Producing Plants

In other aspects, the present disclosure relates generally to methods of producing a plant having enhanced aluminum resistance by expressing a variant phosphoenolpyruvate carboxylase (PEPC) in the plant. In some embodiments, the expression of a variant PEPC in the plant is achieved by means of plant transformation. In some embodiments, the expression of a variant PEPC in the plant is achieved by means of genome editing, such as the CRISPR/Cas method.

Plant Transformation

In one aspect, the expression of a variant PEPC of the present disclosure in the plant is achieved by means of plant transformation. For example, in some embodiments, the present disclosure provides a method for producing a plant expressing a variant phosphoenolpyruvate carboxylase (PEPC), comprising: (a) introducing an expression cassette of any of the preceding embodiments into a plant cell to form a transformed plant cell; and (b) regenerating a plant from the transformed plant cell, where the plant expresses the variant PEPC and has enhanced aluminum resistance as compared to a control plant of the same species that does not express the variant PEPC.

As used herein, the term "plant transformation" encompasses all techniques by which a heterologous nucleic acid may be introduced into a plant cell. As used herein, a "heterologous nucleic acid" refers to a nucleic acid or a portion thereof that is not native to the host cell in nature, such as an artificially assembled expression cassette. A host cell or organism containing the heterologous nucleic acid stably integrated into the genome is referred to as a "transformed" cell or organism.

An expression cassette of the present disclosure may be introduced into the genome of the desired plant host by a variety of conventional techniques. For example, the expression cassette may be introduced directly into the genomic DNA of the plant cell using techniques such as electroporation and microinjection of plant cell protoplasts, or the expression cassette can be introduced directly to plant tissue using ballistic methods, such as DNA particle bombardment. Alternatively, the expression cassette may be combined with suitable T-DNA flanking regions and introduced into a conventional *Agrobacterium* host vector. The virulence functions of the *Agrobacterium* host will direct the insertion of the construct and adjacent marker into the plant cell DNA when the cell is infected by the bacteria. While transient expression of the constitutively active PEPC is encompassed by the disclosure, generally, expression of a construct of the present disclosure will be from insertion of expression cassettes into the plant genome, e.g., such that at least some plant offspring also contain the integrated expression cassette. Microinjection techniques are also useful for this purpose. These techniques are well known in the art and thoroughly described in the literature. The introduction of expression cassettes using polyethylene glycol precipitation is described in Paszkowski et al. EMBO J. 3:2717-2722 (1984). Electroporation techniques are described in Fromm et al. Proc. Natl. Acad. Sci. USA 82:5824 (1985). Ballistic transformation techniques are described in Klein et al. Nature 327:70-73 (1987). *Agrobacterium*-mediated transformation techniques, including disarming and use of binary vectors, are well described in the scientific literature. See, for example, Horsch et al. Science 233:496-498 (1984), and Fraley et al. Proc. Natl. Acad. Sci. USA 80:4803 (1983).

The following are representative publications disclosing plant transformation protocols that can be used to genetically transform the following plant species: maize (U.S. Pat. Nos. 5,177,010 and 5,981,840); soybean (U.S. Pat. Nos. 5,416,011; 5,569,834; 5,824, 877; 5,563,04455 and 5,968, 830); wheat (Ortiz et al., 1996, Plant Cell Rep. 15, 877); barley (U.S. Pat. No. 6,100,447); rice (Alam et al., 1999, Plant Cell Rep. 18, 572); sorghum (Guo et al., 2015, Methods Mol Biol 1223, 181-188; Howe et al., Plant Cell Rep 25(8): 784-791, 2006). Transformation of other species is also contemplated by the disclosure. Suitable methods and protocols for transformation of other species are available in the scientific literature and known to those of skill in the art.

Transformed plant cells derived by any of the above transformation techniques may be cultured to regenerate a whole plant that possesses the transformed genotype and thus the desired phenotype, e.g., aluminum resistance. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof (see, e.g., Klee et al., Ann. Rev. of Plant Phys. 38:467-486, 1987).

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed. The expression cassettes and other constructs of the present disclosure can be used to confer aluminum resistance on essentially any plant. In some embodiment, the plant is a grain-, vegetable-, or fruit-producing plant.

Those of skill will recognize that a number of plant species can be used as models to predict the phenotypic effects of transgene expression in other plants. For example, it is well recognized that *Arabidopsis* plants are useful models of transgene expression. In some embodiments, the plants of the present disclosure have enhanced PEPC-mediated phenotypes, for example enhanced aluminum resistance, as compared to a control plant of the same species that does not express the variant PEPC.

CRISPR/Cas

In another aspect, the expression of a variant PEPC of the present disclosure in the plant is achieved by means of genome editing, such as the CRISPR/Cas method.

Plant gene manipulations can now be precisely tailored in non-transgenic organisms using the CRISPR/Cas9 genome editing method. In this bacterial antiviral and transcriptional regulatory system, a complex of two small RNAs—the CRISPR-RNA (crRNA) and the trans-activating crRNA (tracrRNA)—directs the nuclease (Cas9) to a specific DNA sequence complementary to the crRNA (Jinek, M., et al. Science 337, 816-821 (2012)). Binding of these RNAs to Cas9 involves specific sequences and secondary structures in the RNA. The two RNA components can be simplified into a single element, the single guide-RNA (sgRNA), which is transcribed from a cassette containing a target sequence defined by the user (Jinek, M., et al. Science 337, 816-821 (2012)). This system has been used for genome editing in humans, zebrafish, *Drosophila*, mice, nematodes, bacteria, yeast, and plants (Hsu, P. D., et al., Cell 157, 1262-1278 (2014)). In this system the nuclease creates double stranded breaks at the target region programmed by the sgRNA. These can be repaired by non-homologous recombination, which often yields inactivating mutations. The breaks can also be repaired by homologous recombination, which enables the system to be used for gene targeted gene replacement (Li, J.-F., et al. Nat. Biotechnol. 31, 688-691, 2013; Shan, Q., et al. Nat. Biotechnol. 31, 686-688, 2013). In some embodiments of the methods in the present disclosure, a gene encoding a wild-type or endogenous PEPC in a plant may be modified using the CAS9/CRISPR system to match the nucleic acid sequence encoding a variant PEPC described herein.

Thus, in some embodiments, instead of generating a transgenic plant, a wild-type PEPC coding sequence in a plant or plant cell can be altered in situ to generate a plant or plant cell carrying a nucleic acid encoding a variant PEPC described herein of the present disclosure. The CRISPR/Cas system has been modified for use in prokaryotic and eukaryotic systems for genome editing and transcriptional regulation. The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize the RNA-mediated nuclease, Cas9 in complex with guide and activating RNA to recognize and cleave foreign nucleic acid. Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chloroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21.

Accordingly, in some embodiments, the present disclosure provides a method for producing a plant expressing a variant phosphoenolpyruvate carboxylase (PEPC), comprising: (a) introducing a clustered regularly interspaced short palindromic repeats (CRISPR) associated protein (Cas9) genome-editing system into a plant cell to form a transformed plant cell comprising a nucleic acid of any one of the preceding embodiments; and (b) regenerating a plant from the transformed plant cell, where the plant expresses the variant PEPC and has enhanced aluminum resistance as compared to a control plant of the same species that does not express the variant PEPC.

V. Plants and Cultivation Thereof

Further aspects of the disclosure relate generally to plants comprising a variant PEPC described above, as well as methods of cultivating them.

Accordingly, in one aspect, the present disclosure provides a plant expressing a variant phosphoenolpyruvate carboxylase (PEPC), where the variant PEPC comprises at least one amino acid substitution at a position corresponding to one or more of residues A651, G678, A776, T778, and R886, in the consensus sequence of SEQ ID NO:8, where the plant was not grown from seeds subjected to ethyl methanesulfonate mutagenesis (EMS) mutagenesis, or the plant was not a progeny of an ancestral plant grown from seeds subjected to EMS mutagenesis, and where the amino acid sequence of the variant is at least 95% identical to the consensus sequence of SEQ ID NO:8. In some embodiments, the plant of the present disclosure comprises a variant PEPC that is expressed in roots of the plant. In some embodiments, the plant of the present disclosure has enhanced aluminum resistance as compared to a control plant of the same species that does not express the variant PEPC.

Any plant may be subjected to methods disclosed herein to express a variant PEPC of the present disclosure. In some embodiments, the plant is a species of plant of the genus *Abelmoschus, Allium, Apium, Amaranthus, Arachis, Arabidopsis, Asparagus, Atropa, Avena, Benincaca, Beta, Brassica, Cannabis, Capsella, Cica, Cichorium, Citrus, Citrullus, Capsicum, Carthamus, Cocos, Coffea, Cucumis, Cucurbita, Cynasa, Daucus, Diplotaxis, Dioscorea, Elais, Eruca, Foeniculum, Fragaria, Glycine, Gossypium, Helianthus, Heterocallis, Hordeum, Hyoscyamus, Ipomea, Lactuca, Lagenaria, Lepidium, Linum, Lolium, Luffa, Luzula, Lycopersicon, Malus, Manihot, Majorana, Medicago, Momodica, Musa, Nicotiana, Olea, Oryza, Panicum, Pastinaca, Pennisetum, Persea, Petroselinium, Phaseolus, Physalis, Pinus, Pisum, Populus, Pyrus, Prunus, Raphanus, Saccharum, Secale, Senecio, Sesamum, Sinapis, Solanum, Sorghum, Spinacia, Theobroma, Trichosantes, Trigonella, Triticum, Turritis, Valerianelle, Vitis, Vigna,* or *Zea*. In particular embodiments, the plant is maize (*Zea mays*). In some embodiments, the plant is soybean (*Glycine max*), wheat (*Triticum aestivum*), barley (*Hordeum vulgare*), rice (*Oryza sativa*), or sorghum (*Sorghum bicolor*).

In another aspect, the present disclosure provides a method of enhancing aluminum resistance in a plant, comprising: (a) crossing the plant of any one of the preceding embodiments with a second plant of the same genus or same species to generate F1 seeds; (b) growing F1 plants from the F1 seeds in a phytotoxic substrate, and (c) selecting a plant with enhanced aluminum resistance as compared to the second plant, where the phytotoxic substrate is an acidic substrate having a pH from 2-5 and micromolar or higher levels of $Al^{3+}$.

In some embodiments, plants having a variant PEPC and enhanced aluminum resistance may be identified using available techniques in the art, e.g., visual stains for polysaccharide callose (an indication of aluminum-dependent damage) and visual stains for internalized aluminum (e.g., morin), as described in Example 2.

In some embodiments, the present disclosure relates to a part of the plant having enhanced aluminum resistance, where the plant part contains a variant PEPC of any of the preceding embodiments. In some embodiments, the plant part is a stem, a branch, a root, a leaf, a flower, a fruit, a seed, a cutting, a bud, a cell, or a portion thereof. In some embodiments, the present disclosure provides seed from which the plant can be grown.

A. Carbon Sequestration in Soil

Release of organic acids into the root growth environment is a major contributor to deposition of carbon-based compounds into soils. Increased PEPC activity in roots increases production of organic acids including malate and pyruvate. In this way, increased release of organic acids by plants engineered to express the variant PEPC enzymes of the present disclosure increases sequestration of carbon into soil. In particular, plants engineered to express the variant PEPC enzymes of the present disclosure are contemplated to more effectively remove carbon dioxide from the atmosphere by more effectively depositing carbon-containing compounds into the soil, relative to a control plant of the same species (e.g., wild type or parental plant) that does not express the variant PEPC.

B. Extraction of Phosphate from Soil

Release of organic acids including malate and citrate into the root growth environment is important for extracting anionic nutrients such as phosphate from the soil. The organic acids compete with phosphate and other anions for binding to cations such as aluminum and iron, thus releasing anions such as phosphate for uptake by plants. In this way, increased release of organic acids by plants engineered to express the variant PEPC enzymes of the present disclosure increases the capability of plants to extract nutrients from the soil, relative to a control plant of the same species (e.g., wild type or parental plant) that does not express the variant PEPC.

C. Production of Essential Amino Acids

Oxaloacetate, the immediate product of PEPC, is the precursor to the amino acid aspartic acid. The amino acids asparagine, lysine, threonine, methionine, and isoleucine are all derived from aspartic acid. Lysine, threonine, methionine, and isoleucine are all considered to be essential nutrients for animals including humans. Hence, plants engineered to express the variant PEPC enzymes of the present disclosure are contemplated to produce higher levels of oxaloacetate and higher levels of aspartate-derived essential amino acids, relative to a control plant of the same species (e.g., wild type or parental plant) that does not express the variant PEPC.

D. Production of Glucose

Oxaloacetate produced by PEPC is converted by malate dehydrogenase to malate, which through C4 photosynthesis supplies $CO_2$ for synthesis of glucose via the Calvin Cycle. C4 PEPC represents a unique variant of PEPC strictly related to photosynthesis in planta. Introduction of A651V, G678S, and T778I in the consensus sequence of SEQ ID NO:8 to maize C4 PEPC (ZmPPC1) each results in increased activity of C4 PEPC consistent with what was observed in the context of *Arabidopsis* C3 PEPC (AtPPC1). Hence, plants engineered to express the variant C4 PEPC enzymes of this disclosure are contemplated to produce higher levels of oxaloacetate, malate, and consequently glucose relative to a control plant of the same species (e.g. wild type or parental plant) that does not express the variant PEPC.

Exemplary Embodiments

1. A plant expressing a variant phosphoenolpyruvate carboxylase (PEPC), wherein the variant PEPC comprises:
   (i) an amino acid substitution at a position corresponding to one or more of residues A651, G678, and T778, in the consensus sequence of SEQ ID NO:8, and/or
   (ii) an amino acid substitution at a position corresponding to one or both of residue A776 and R886, in the consensus sequence of SEQ ID NO:8, optionally wherein the plant was not grown from seeds subjected to ethyl methane sulfonate mutagenesis (EMS) mutagenesis, or the plant was not a progeny of an ancestral plant grown from seeds subjected to EMS mutagenesis, and/or optionally wherein the amino acid sequence of the variant is:
   (a) at least 90% identical to any one of SEQ ID NOs:1-9 and 15; or
   (b) at least 95% identical to the consensus sequence of SEQ ID NO:8; or
   (c) at least 95% identical to the consensus sequence of SEQ ID NO:9.

2. The plant of embodiment 1, wherein the variant PEPC comprises a further amino acid substitution at a position corresponding to one or more of residues R637, X675, K831, R890 and N965 in the consensus sequence of SEQ ID NO:8, wherein X675 is Q675 or H675.

3. The plant of embodiment 1, wherein the variant PEPC comprises an amino acid substitution at a position corresponding to one or more of residues A651, G678, and T778 in the consensus sequence of SEQ ID NO:8.

4. The plant of embodiment 3, wherein the variant PEPC further comprises an amino acid substitution at a position corresponding to one or both of A776 and R886 in the consensus sequence of SEQ ID NO:8.

5. The plant of embodiment 1, wherein the variant PEPC comprises one or more amino acid substitutions selected from the group consisting of A651V, G678S, A776S, T778I, and R886G.

6. The plant of embodiment 1, wherein the variant PEPC comprises one or more amino acid substitutions selected from the group consisting of A651V, G678S, and T778I.

7. The plant of embodiment 6, wherein the variant PEPC further comprises an amino acid substitution selected from the group consisting of one or both of A776S and R886G.

8. The plant of embodiment 1, wherein the amino acid sequence of the variant is at least 99% identical to SEQ ID NO:9, and the amino acid sequence of the variant does not consist of SEQ ID NO:10, SEQ ID NO:11, or SEQ ID NO:12.

9. The plant of embodiment 1, wherein the variant PEPC is expressed in roots of the plant.

10. The plant of any one of embodiments 1-9, wherein the plant has enhanced aluminum resistance as compared to a control plant of the same species that does not express the variant PEPC.

11. The plant of embodiment 10, wherein:
   (a) growth of the plant is greater in a phytotoxic substrate as compared to the control plant when grown under the same conditions; and/or
   (b) aluminum accumulation in roots of the plant is reduced after growth in the phytotoxic substrate as compared to the control plant when grown under the same conditions; and/or
   (c) carbon-containing organic acid accumulation in the phytotoxic substrate is increased after growth of the plant in the phytotoxic substrate as compared to the control plant when grown under the same conditions,
   wherein the phytotoxic substrate is a growth substrate having a pH from 2-5 and nanomolar or higher levels of $Al^{3+}$.

12. The plant of any one of embodiments 1-11, wherein the plant is not *Arabidopsis*, optionally wherein the plant is selected from the group consisting of maize, soybean, wheat, barley, rice and sorghum, optionally wherein the plant is maize.

13. An isolated nucleic acid encoding a variant phosphoenolpyruvate carboxylase (PEPC) comprising:
   (i) an amino acid substitution at a position corresponding to one or more of residues A651, G678, and T778, in the consensus sequence of SEQ ID NO:8, and/or (ii) an amino acid substitution at a position corresponding to one or both of residue A776 and R886, in the consensus sequence of SEQ ID NO:8, optionally wherein the amino acid sequence of the variant is:

(a) at least 90% identical to any one of SEQ ID NOs:1-9 and 15; or (b) at least 95% identical to the consensus sequence of SEQ ID NO:8; or (c) at least 95% identical to the consensus sequence of SEQ ID NO:9; and the amino acid sequence of the variant does not consist of SEQ ID NO:10, SEQ ID NO:11, or SEQ ID NO:12.

14. The nucleic acid of embodiment 13, wherein the variant PEPC comprises a further amino acid substitution at a position corresponding to one or more of residues R637, X675, K831, R890 and N965 in the consensus sequence of SEQ ID NO:8, wherein X675 is Q675 or H675.

15. The nucleic acid of embodiment 13, wherein the variant PEPC comprises an amino acid substitution at a position corresponding to one or more of residues A651, G678, and T778 in the consensus sequence of SEQ ID NO:8.

16. The nucleic acid of embodiment 15, wherein the variant PEPC further comprises an amino acid substitution at a position corresponding to one or both of A776 and R886 in the consensus sequence of SEQ ID NO:8.

17. The nucleic acid of embodiment 13, wherein the variant PEPC comprises one or more amino acid substitutions selected from the group consisting of A651V, G678S, A776S, T778I, and R886G.

18. The nucleic acid of embodiment 13, wherein the variant PEPC comprises one or more amino acid substitutions selected from the group consisting of A651V, G678S, and T778I.

19. The nucleic acid of embodiment 18, wherein the variant PEPC further comprises an amino acid substitution selected from the group consisting of one or both of A776S and R886G.

20. The nucleic acid of embodiment 13, wherein the amino acid sequence of the variant is at least 99% identical to SEQ ID NO:9.

21. An expression cassette comprising a promoter operably linked to the nucleic acid of any one of embodiments 13-20.

22. The expression cassette of embodiment 21, wherein the promoter is heterologous to the nucleic acid.

23. The expression cassette of 22, wherein the promoter is a root-specific promoter.

24. The expression cassette of embodiment 22, wherein the promoter is a constitutive promoter.

25. The expression cassette of embodiment 22, wherein the promoter is an inducible promoter.

26. An expression vector comprising the expression cassette of any one of embodiments 22 to 25.

27. A host cell comprising the expression cassette of any one of embodiments 22 to 25.

28. The cell of embodiment 27, wherein the host cell is a plant cell.

29. A transgenic plant comprising or regenerated from the cell of embodiment 28.

30. The transgenic plant of embodiment 29, wherein the plant expresses the variant PEPC.

31. The transgenic plant of embodiment 30, wherein the plant has enhanced aluminum resistance as compared to a control plant of the same species that does not express the variant PEPC.

32. A method for producing a plant expressing a variant phosphoenolpyruvate carboxylase (PEPC), comprising:

(a) introducing the expression cassette of any one of embodiments 21 to 25 into a plant cell to form a transformed plant cell; and (b) regenerating a plant from the transformed plant cell, wherein the plant expresses the variant PEPC and has enhanced aluminum resistance as compared to a control plant of the same species that does not express the variant PEPC.

33. A method for producing a plant expressing a variant phosphoenolpyruvate carboxylase (PEPC), comprising:

(a) introducing a clustered regularly interspaced short palindromic repeats (CRISPR) associated protein (Cas9) genome-editing system into a plant cell to form a transformed plant cell comprising the nucleic acid of any one of embodiments 13-20; and (b) regenerating a plant from the transformed plant cell, wherein the plant expresses the variant PEPC and has enhanced aluminum resistance as compared to a control plant of the same species that does not express the variant PEPC.

34. A plant produced by the method of embodiment 32 or embodiment 33.

35. A method of enhancing aluminum resistance in a plant, comprising:

(a) crossing the plant of any one of embodiments 1-12 with a second plant of the same genus or same species to generate F1 seeds;

(b) growing F1 plants from the F1 seeds in a phytotoxic substrate, and (c) selecting a plant with enhanced aluminum resistance as compared to the second plant, wherein the phytotoxic substrate is a growth substrate having a pH from 2-5 and nanomolar or higher levels of $Al^{3+}$.

36. Seed from which the plant of any one of the preceding embodiments can be grown.

37. A method for sequestering carbon in soil, comprising:

growing the plant of any one of embodiments 1-12, 29-31 and 34 in soil under conditions effective for production of a carbon-containing organic acid by the plant and release of the organic acid from roots of the plant into the soil.

38. A method for extracting phosphate from soil, comprising:

growing the plant of any one of embodiments 1-12, 29-31 and 34 in soil under conditions effective for production of a carbon-containing organic acid by the plant and release of the organic acid from roots of the plant into the soil resulting in extraction of inorganic phosphate from the soil by the roots of the plant.

39. The method of embodiment 37 or embodiment 38, wherein the organic acid comprises one or more of pyruvate, malate and citrate.

40. A method for producing an oxaloacetate-derived amino acid, comprising:

growing the plant of any one of embodiments 1-12, 29-31 and 34 in soil under conditions effective for production of an oxaloacetate-derived amino acid by the plant.

41. The method of embodiment 40, wherein the oxaloacetate-derived amino acid comprises one or more of asparagine, lysine, threonine, methionine, and isoleucine.

42. A method for producing glucose, comprising:
   growing the plant of any one of embodiments 1-12, 29-31 and 34 in soil in the presence of light and under conditions effective for production of glucose by the plant.
43. The method of any one of embodiments 37-42, wherein the soil has nanomolar or higher levels of $Al^{3+}$.

EXAMPLES

Abbreviations: AtPPC1 (*Arabidopsis thaliana* PPC1); EMS (ethyl methanesulfonate); PEP (phosphoenolpyruvate); PEPC (phosphoenolpyruvate carboxylase); wt (wild type); ZmPEP7 (*Zea mays* PEP7); and ZmPPC1 (*Zea mays* PPC1).

Although, the present disclosure has been described in some detail by way of illustration and example for purposes of clarity and understanding, it will be apparent to those skilled in the art that certain changes and modifications may be practiced. Therefore, the following synthetic and biological examples should not be construed as limiting the scope of the present disclosure, which is delineated by the appended claims.

Example 1—Identification of *Arabidopsis thaliana* Mutants

Three *Arabidopsis thaliana* mutants with increased aluminum resistance were isolated from a pool of ethyl methanesulfonate (EMS) mutagenized seeds (see, Larsen et al., Plant Physiol, 117:9-18, 1998, herein incorporated by reference in its entirety). These mutants were identified by screening for those with greater than wild-type root growth in the presence of highly inhibitory levels of aluminum (FIG. 1). Through this screen, mutants with upwards of 4-fold higher growth in the presence of the highly inhibitory levels of aluminum were isolated. The isolated mutants were designated as alr-108, alr-128, and alr-139. All three mutants were found to possess amino acid substitutions in a phosphoenolpyruvate carboxylase (PEPC) sequence, relative to the amino acid sequence of wild type *Arabidopsis thaliana* PEPC set forth as SEQ ID NO:1 (UniProt ID NO. Q9MAH0). Mutant alr-108 contains the amino acid substitution A651V. Mutant alr-128 contains the amino acid substitution G678S. Mutant alr-139 contains the amino acid substitution T778I. Positions of substitutions are relative to the wild type *Arabidopsis thaliana* C3 PEPC sequence of SEQ ID NO:1 and the consensus sequence of SEQ ID NO:8.

Example 2—Aluminum-Dependent Damage and Aluminum Accumulation

Figure 2A:
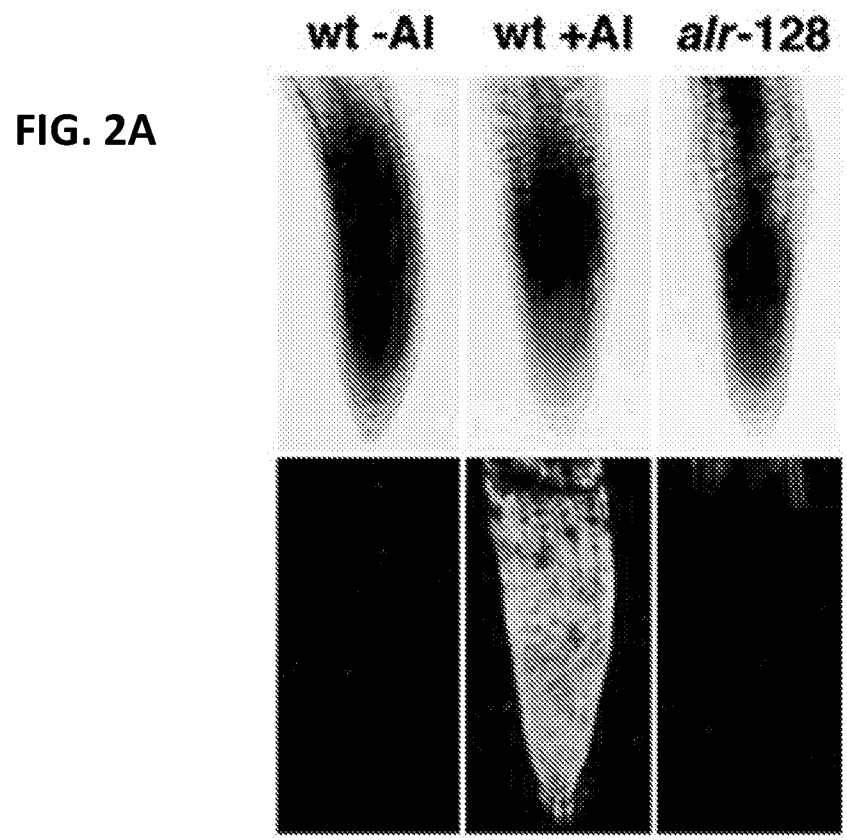
FIG. 2A shows aluminum-dependent callose accumulation in roots of wild type (wt) and mutant (alr-128) *Arabidopsis thaliana* plants. Roots of seedlings were exposed to a nutrient solution containing 75 µM $AlCl_3$ (pH 4.2) for 24 hours, except for the first panel in which no aluminum was added. The top row shows bright-field images, while the bottom row shows fluorescence images showing callose accumulation.
Figure 2B:
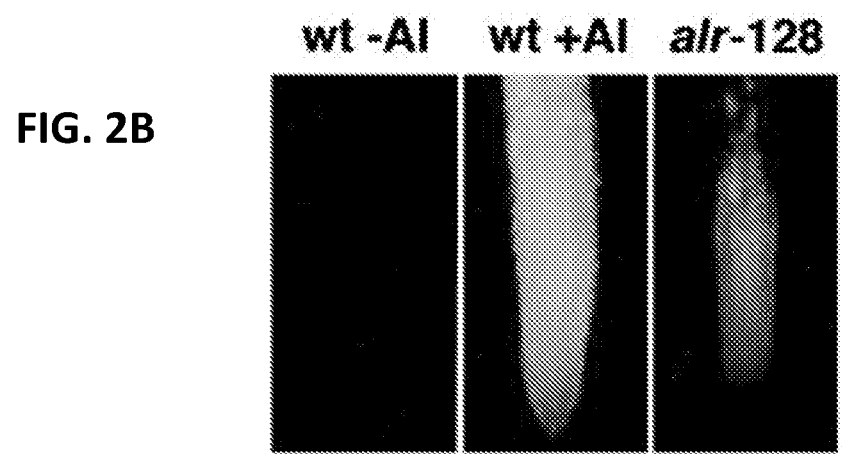
FIG. 2B shows patterns of aluminum accumulation by roots of wild type (wt) and mutant (alr-128) *Arabidopsis thaliana* plants. Seedlings grown in nutrient solution without aluminum were exposed to solution containing 25 µM $AlCl_3$ (pH 4.2) for 1 hour, except for the first panel in which no aluminum was added. Roots were stained with morin, which fluoresces when complexed with aluminum.

Subsequent to identification of the *Arabidopsis* mutants having enhanced aluminum-resistance, the physiological nature of the resistance was assessed. Mutant alr-128 was found to have reduced accumulation of the stress polysaccharide callose. In addition, this mutant was found to have reduced internalization of aluminum. Exemplary results are shown for mutant alr-128 (FIG. 2A and FIG. 2B). Thus, the aluminum-resistance phenotype was determined to be associated with enhanced aluminum exclusion in mutant alr-128.

Example 3—Aluminum-Dependent Organic Acid Exudation

Figure 3:
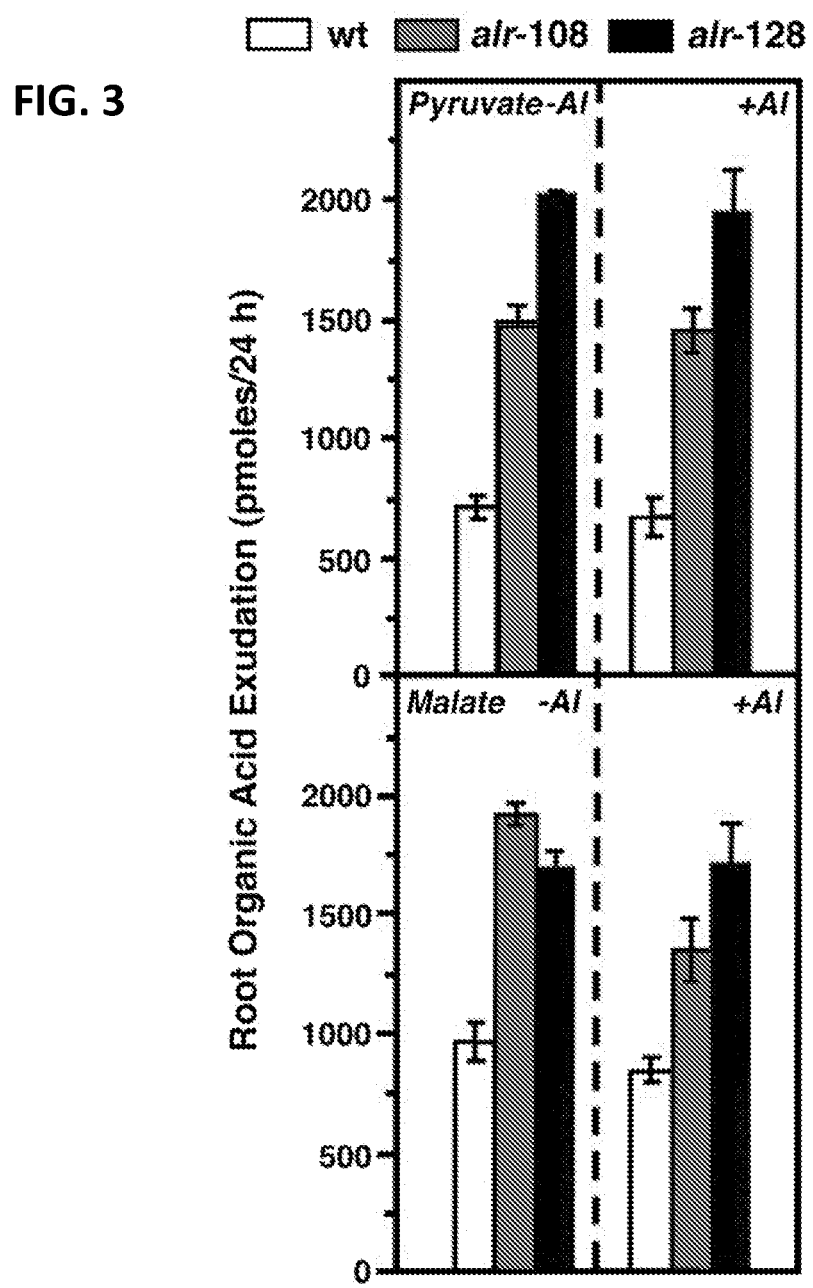
FIG. 3 shows pyruvate and malate exudation by roots of wild type (wt) and mutant (alr-108 and alr-128) *Arabidopsis thaliana* plants that were grown in a simple salt solution (pH 4.2) in the presence or absence of 2.7 µM $AlCl_3$.
Figure 4:
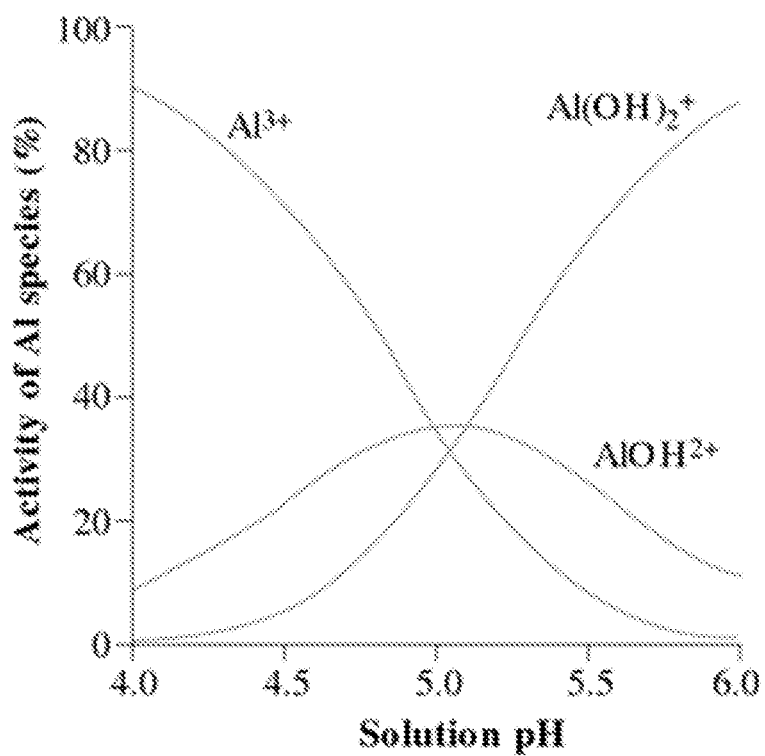
FIG. 4 shows the relationship between pH and presence of aluminum ions.

Further analysis of the mutants involved assessment of organic acid exudation. Mutants alr-108 and alr-128 were found to have increased levels of pyruvate and malate exudation, which was independent of the presence of aluminum (FIG. 3). Thus, the aluminum-resistance phenotype was determined to be associated with enhanced exudation of aluminum-chelating organic acids.

Example 4—Analysis of Activity of *Arabidopsis thaliana* and *Zea mays* PEPC Enzymes For both *Arabidopsis* C3 PPC1 (AtPPC1) and maize C4 PPC1 (ZmPPC1), the entire coding sequence for each was cloned into pET22b, which contains an amino-terminal 6×-HIS tag for protein purification, and expression was driven by the T7 promoter and lac operon. Relevant mutations were introduced by the Stratagene QuikChange mutagenesis kit using PCR amplification. Both wild type and mutant cDNA constructs were sequenced entirely following cloning into pet22b. Proteins were produced by growing transformed *E. coli* (BL21 CodonPlus) in autoinduction medium at 18° C. for 16 hours. Proteins were isolated by sonication of bacterial cells followed by passage over a nickel sepharose affinity column, elution with imidazole and separation on a GE SUPERDEX HILOAD 200 PG 16/60 all using an AKTA FPLC.

Enzyme analysis was conducted in vitro using protein that was generated by expression in *E. coli* using the pET22b vector. For expression, pET22b constructs were transformed into *E. coli* BL21-DE3 codon plus RIL cells and grown at 37° C. in autoinduction media until reaching an OD=1 after which these were transferred to 18° C. for 18 hours. Samples were collected and lysed by sonication. Protein was purified by passage through a His-trap nickel affinity column on an Akta FPLC and then eluted with 400 mM imidazole. Partially purified protein was then separated on an FPLC equipped with a HiPrep S200 size exclusion column (16/60) after which collected sample was concentrated by centrifugation to a final concentration of 4 mg/ml in 50% glycerol. Samples were stored at −20° C.

For enzymatic assays, a malate dehydrogenase coupled reaction was conducted with a range of substrate concentrations (0-7.5 mM phosphoenolpyruvate pyruvate) and a range of concentrations of allosteric inhibitor (0-50 mM malate). Assays were monitored using a Victor2 microplate reader at 25° C. Reactions consisted of 15 mM PPC enzyme variants, 50 mM HEPES pH7.5, 10 mM $MgCl_2$, 10 mM $KHCO_3$ (carbonate substrate), 0.2 mM NADH, and 10 units/ml of malate dehydrogenase. Reaction time was 15 minutes and samples were measured on an ~40 second interval. For measurement, which monitors loss of NADH, excitation wavelength was 340 nM and emission wavelength was 460 nM. From these assays, the enzyme kinetics of Tables 4-1 and 4-2 were determined for each enzyme variant.

TABLE 4-1

*Arabidopsis thaliana* and Engineered C3 PEPC Enzyme Kinetics

| A. thaliana PPC1 | $K_m$ PEP (mM) | $V_{max}$ (units/mg) | $K_{cat}/K_m$ | $K_i$ malate (mM) | M* |
|---|---|---|---|---|---|
| AtPPC1 wild type | 2.738 ± 0.166 | 24.992 ± 0.69 | 16.687 | 0.21 ± 0.02 | MX |
| AtPPC1 R886G | 1.111 ± 0.036 | 12.586 ± 0.14 | 20.769 | 17.43 ± 2.49 | CO |
| AtPPC1 A651V | 0.956 ± 0.040 | 15.776 ± 0.25 | 30.253 | 36.12 ± 8.71 | CO |
| AtPPC1 G678S | 0.433 ± 0.040 | 17.784 ± 0.44 | 75.300 | ND | MX |
| AtPPC1 T778I | 1.087 ± 0.027 | 14.738 ± 0.15 | 24.933 | 2.19 ± 0.21 | CO |

*M = model of inhibition (MX—mixed, CO—competitive, NC—non-competitive)

TABLE 4-2

Zea mays and Engineered C4 PEPC Enzyme Kinetics

| Z. mays PPC1 | $K_m$ PEP (mM) | $V_{max}$ (units/mg) | $K_{cat}/K_m$ | $K_i$ malate (mM) | M* |
|---|---|---|---|---|---|
| ZmPPC1 wild type | 4.621 ± 0.406 | 17.56 ± 2.35 | 4.623 | 1.90 ± 0.08 | CO |
| ZmPPC1 A651V | 0.477 ± 0.042 | 12.84 ± 0.89 | 32.740 | 26.26 ± 3.80 | CO |
| ZmPPC1 G678S | 2.664 ± 0.333 | 17.74 ± 1.04 | 8.101 | 7.10 ± 0.43 | CO |
| ZmPPC1 T778I | 1.191 ± 0.104 | 14.05 ± 0.44 | 14.351 | 18.25 ± 1.24 | CO |

*M = model of inhibition (MX—mixed, CO—competitive, NC—non-competitive)

Figure 6:
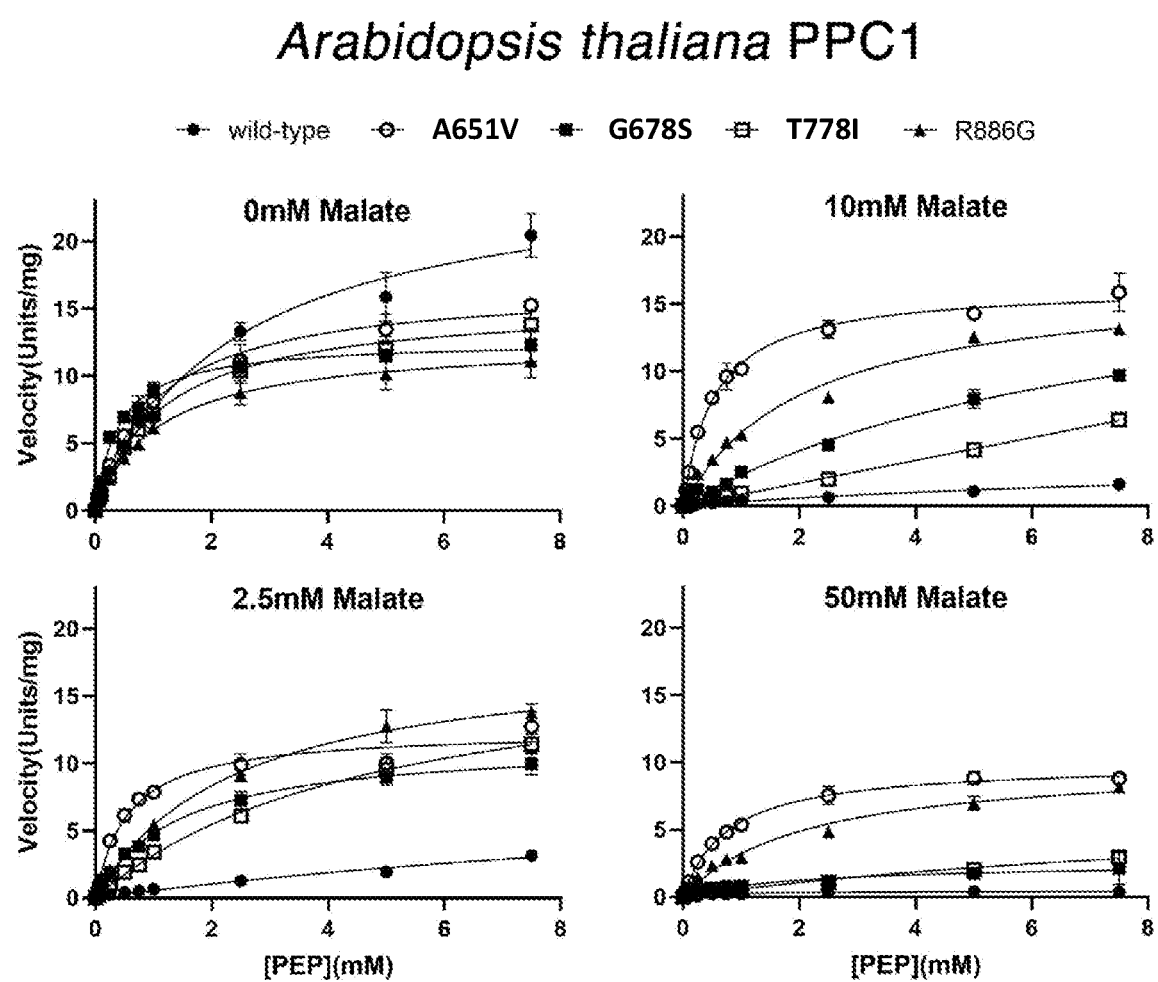
FIG. 6 shows the enzymatic activity of wild type *Arabidopsis thaliana* PPC1 (SEQ ID NO:1) as compared to engineered PEPC enzymes. AtPPC1 is C3 PEPC. The graphs show increasing concentrations of the substrate phosphoenolpyruvate (x-axis) plotted against velocity (y-axis) at different concentrations of malate. The engineered *Arabidopsis thaliana* PPC1 enzymes have a A651V substitution (alr-108), a G678S substitution (alr-128), a T778I substitution (alr-139), or a R886G substitution. Amino acid positions of engineered PEPC enzymes are relative to the amino acid sequences of both wild type *Arabidopsis thaliana* PPC1 (SEQ ID NO:1) and the consensus (SEQ ID NO:8).

FIG. 6 and Table 4-1 show the enzymatic activity of wild type (wt) *Arabidopsis thaliana* C3 PPC1 (SEQ ID NO:1) as compared to engineered PEPC enzymes. An increase in $K_{cat}/K_m$, which represents catalytic efficiency, was observed for all AtPPC1 mutants relative to wt AtPPC1. The G678S (alr-128) mutant had the highest increase in catalytic efficiency, with a nearly 5-fold increase over wt AtPPC1. Additionally, the $K_m$, which is a measure of how tightly the enzyme binds to its PEP substrate (phosphoenolpyruvate), was found to be substantially decreased for all AtPPC1 mutants tested. Lower $K_m$ represents a greater substrate-binding ability, even at low substrate concentrations. Comparison of wt and G678S AtPPC1 with regard to $K_m$ showed that the G678S mutant has an 85% reduction in $K_m$ and therefore binds substantially more tightly to the PEP substrate resulting in the large increase in catalytic efficiency.

Figure 7:
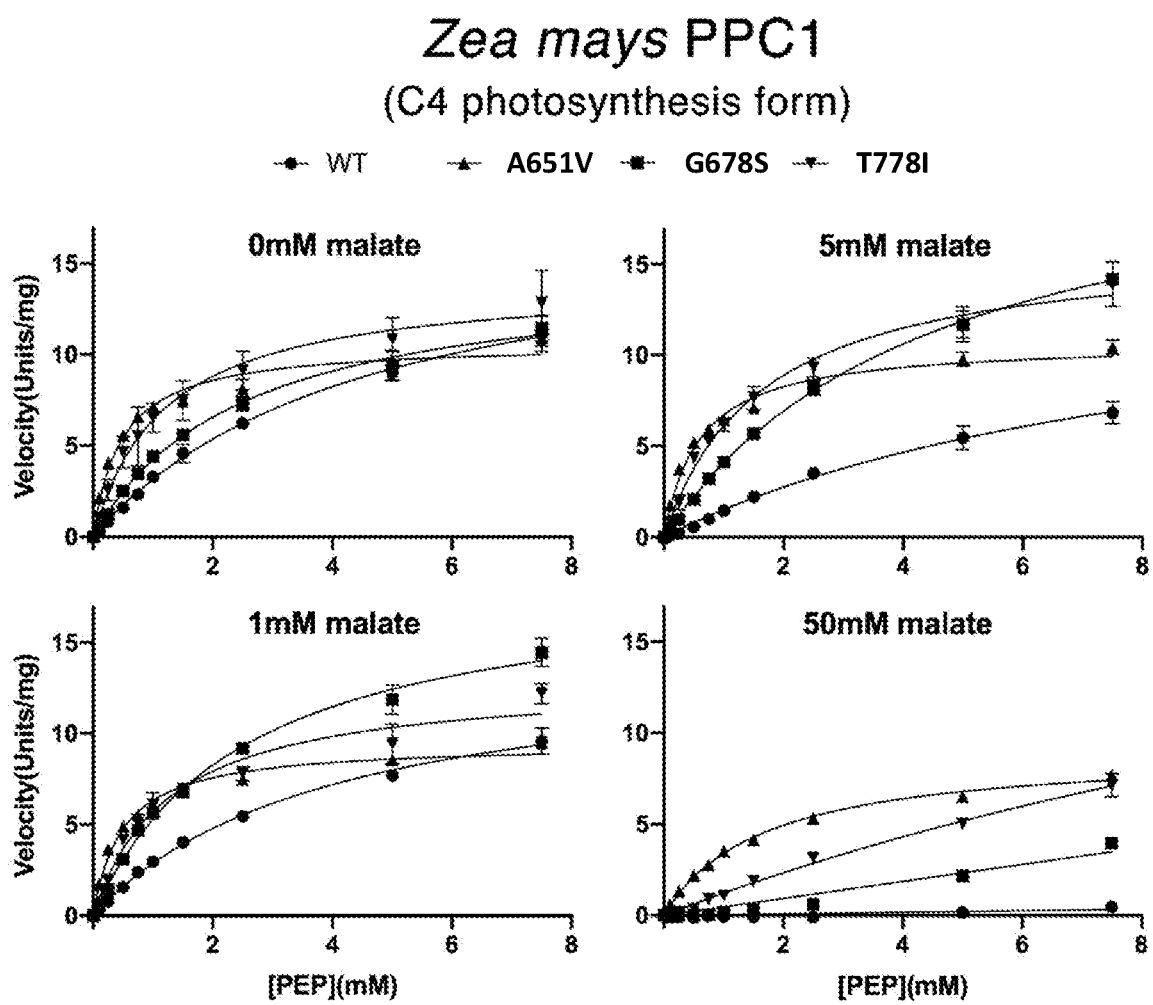
FIG. 7 shows the enzymatic activity of wild type *Zea mays* PPC1 (SEQ ID NO:15) as compared to engineered PEPC enzymes. ZmPPC1 is a C4 PEPC. The graphs show increasing concentrations of the substrate phosphoenolpyruvate (x-axis) plotted against velocity (y-axis) at different concentrations of malate. The amino acid sequence of wild type *Zea mays* PPC1 has serine (S) at position 780 and glycine (G) at position 890 (SEQ ID NO:15), which corresponds to positions 776 and 886, respectively in the consensus (SEQ ID NO:8). The engineered *Zea mays* PPC1 enzymes have a A651V substitution (alr-108), a G678S substitution (alr-128), or a T778I substitution (alr-139), in addition to serine (S) at position 776 and glycine (G) at position 886. Amino acid positions of engineered PEPC enzymes are relative to the amino acid sequences of the consensus (SEQ ID NO:8).

FIG. 7 and Table 4-2 show the enzymatic activity of wild type (wt) *Zea mays* C$ PPC1 (SEQ ID NO:15) as compared to engineered PEPC enzymes. In maize, ZmPPC1 is the enzyme responsible for C4 photosynthesis. ZmPP1 has serine (S) at position 776 and glycine (G) at position 886 relative to the consensus sequence of SEQ ID NO:8 (or said another way has S at position 780 and G at position 890 in SEQ ID NO:15). Throughout the present disclosure and unless indicated to the contrary, amino acid positions are numbered relative to SEQ ID NO:8 as determined when the amino acid sequence of an enzyme of interest is aligned to SEQ ID NO:8 using a pairwise alignment algorithm. In maize, all three of the mutations tested had universally positive effects on enzyme activity including reduced $K_m$ (i.e. tighter binding to the substrate), greater catalytic efficiency, and substantially reduced effects of the allosteric inhibitor malate (Ks). In particular, the A651V (alr-108) mutant had an increase in catalytic efficiency by upwards of 7-fold relative to wt ZmPPC1, and the G678S (alr-128) and T778I (alr-139) mutants had increases in catalytic efficiency by nearly 200% and 300% respectively, relative to wt ZmPPC1.

Malate is an allosteric inhibitor of both AtPPC1 and ZmPPC1, albeit in different manners. In the case of AtPPC1, malate inhibits in both a competitive and non-competitive way. Three of the amino acid changes (R886G, A651V and T778I) in AtPPC shift the model of inhibition to competitive. This indicates that these mutations unlink the malate binding pocket from the enzyme's active site, resulting in malate binding only directly affecting substrate affinity. In the case of ZmPPC1, the malate binding pocket for noncompetitive inhibition is already compromised and is partially unlinked from the active site, thus the higher $K_i$ for wt ZmPPC1 compared to AtPPC1. All three aluminum-resistance mutations (A651V, G678S and T778I) in ZmPPC1 greatly reduce the effects of malate on enzyme function. In particular, wt ZmPPC1 is completely inhibited at 50 mM malate while the ZmPPC1 mutants are only partially affected or in the case of A651V ZmPPC1 wholly unaffected by malate.

Example 5—Production of Transgenic *Zea mays*

This example describes the production of transgenic maize engineered to express wild type and mutant PEPC enzymes.

For ZmPEP7 (C3 PEPC), a transgenic construct comprising the ZmPEP7 promoter along with the entirety of the ZmPEP7 genomic construct including 5' and 3'-UTRs, all exons and introns from strain B104, was cloned into pDW3894. Alternatively, a root-specific promoter is used to drive expression of ZmPEP7 or variants thereof. pDW3894 is a T-DNA binary vector obtained from Iowa State University (Ames, IA). The nucleotide sequence of ZmPEP7 mRNA is set forth in NCBI No. NM_001112033, L00542479, which corresponds to GeneID 542479. For maize transformation, wild type (ZmPEP7 amino acid sequence set forth in SEQ ID NO:2) and variant G672S in SEQ ID NO:2 (=G678S in SEQ ID NO:8) transgene constructs were generated. Constructs are transformed into *Zea mays* B104 germplasm via *Agrobacterium*-mediated transformation.

For ZmPPC1 (C4 PEPC), a transgenic construct comprising the ZmPPC1 promoter along with the entirety of the ZmPPC1 genomic construct including 5' and 3'-UTRs, all exons and introns from strain B104, was cloned into pZY101. Alternatively, the ZmPEP7 promoter is used to drive expression of ZmPPC1 or variants thereof. pZY101 is a T-DNA binary vector purchased from Addgene (Watertown, MA). The nucleotide sequence ZmPPC1 mRNA is set forth in NCBI No. NM_001161348, L00542372, which corresponds to GeneID 542372. For maize transformation, wild type (ZmPPC1 amino acid sequence set forth in SEQ ID NO:15) and variant A655V in SEQ ID NO:15 (=A651V in SEQ ID NO:8), G682S in SEQ ID NO:15 (=G678S in SEQ ID NO:8), and T782I in SEQ ID NO:15 (=T778I in SEQ ID NO:8) transgene constructs were generated. Constructs are transformed into *Zea mays* B104 germplasm via *Agrobacterium*-mediated transformation.

Example 6—Root Growth Analysis of Transgenic *Arabidopsis thaliana*

Root growth was examined in transgenic *Arabidopsis* engineered to express wt AtPPC1, or a variant PEPC (G678S AtPPC1 or R886G AtPPC1) in a genotypic background devoid of expression of native AtPPC1. Seedlings from the transgenic *Arabidopsis* strains were grown at 20° C. in a soaked gel environment with aluminum toxicity equivalent to about 50-100 μM in the absence of agar. Root growth was assessed at day 7. A large increase in root growth was observed in the presence of aluminum in transgenic plants expressing G678S AtPPC1 or R886G AtPPC1. The increase in root growth in the presence of a phytotoxic substrate (high levels of aluminum) indicates that both the G678S AtPPC1 and the R886G AtPPC1 transgenic *Arabidopsis* have enhanced levels of aluminum resistance in comparison to plants expressing wt AtPPC1. This is consistent with the improved enzyme kinetics of the G678S AtPPC1 or R886G AtPPC1 enzymes described in Example 5.

SEQUENCES
>SEQ ID NO: 1_Arabidopsis_thaliana (thale cress)
MANRKLEKMASIDVHLRQLVPGKVSEDDKLVEYDALLLDRFLDILQDLHGEDLRETVQELYEHS

AEYEGKHEPKKLEELGSVLTSLDPGDSIVIAKAFSHMLNLANLAEEVQIAYRRRIKKLKKGDFV

DESSATTESDLEETFKKLVGDLNKSPEEIFDALKNQTVDLVLTAHPTQSVRRSLLQKHGRIRDC

LAQLYAKDITPDDKQELDEALQREIQAAFRTDEIKRTPPTPQDEMRAGMSYFHETIWKGVPKFL

RRVDTALKNIGIEERVPYNAPLIQFSSWMGGDRDGNPRVTPEVTRDVCLLARMMAATMYFNQIE

DLMFEMSMWRCNDELRARADEVHANSRKDAAKHYIEFWKSIPTTEPYRVILGDVRDKLYHTRER

AHQLLSNGHSDVPVEATFINLEQFLEPLELCYRSLCSCGDRPIADGSLLDFLRQVSTFGLSLVR

LDIRQESDRHTDVLDAITTHLDIGSYREWSEERRQEWLLSELSGKRPLFGSDLPKTEEIADVLD

TFHVIAELPADSFGAYIISMATAPSDVLAVELLQRECRVKQPLRVVPLFEKLADLEAAPAAVAR

LFSVDWYKNRINGKQEVMIGYSDSGKDAGRLSAAWQLYKAQEELVKVAKEYGVKLTMFHGRGGT

VGRGGGPTHLAILSQPPDTINGSLRVTVQGEVIEQSFGEEHLCFRTLQRFTAATLEHGMRPPIS

PKPEWRALLDEMAVVATEEYRSVVFQEPRFVEYFRLATPELEYGRMNIGSRPSKRKPSGGIESL

RAIPWIFAWTQTRFHLPVWLGFGSAIRHVIEKDVRNLHMLQDMYQHWPFFRVTIDLIEMVFAKG

DPGIAALYDKLLVSEELWPFGEKLRANFEETKKLILQTAGHKDLLEGDPYLKQRLRLRDSYITT

LNVCQAYTLKRIRDPSYHVTLRPHISKEIAESSKPAKELIELNPTSEYAPGLEDTLILTMKGIA

AGLQNTG

>SEQ ID NO: 2_Zea_mays (maize PEP7, 03, root, anaplerosis)
MPERHQSIDAQLRLLAPGKVSEDDKLVEYDALLVDRFLDILQDLHGPHLREFVQECYELSAEYE

NDRDEARLGELGSKLTSLPPGDSIVVASSFSHMLNLANLAEEVQIAHRRRIKLKRGDFADEASA

PTESDIEETLKRLVSQLGKSREEVFDALKNQTVDLVFTAHPTQSVRRSLLQKHGRIRNCLRQLY

AKDITADDKQELDEALQREIQAAFRTDEIRRTPPTPQDEMRAGMSYFHETIWKGVPKFLRRIDT

ALKNIGINERLPYNAPLIQFSSWMGGDRDGNPRVTPEVTRDVCLLARMMAANLYFSQIEDLMFE

LSMWRCSDELRIRADELHRSSRKAAKHYIEFWKQVPPNEPYRVILGDVRDKLYYTRERSRHLLT

SGISEILEEATFTNVEQFLEPLELCYRSLCACGDKPIADGSLLDFLRQVSTFGLALVKLDIRQE

SDRHTDVLDSITTHLGIGSYAEWSEEKRQDWLLSELRGKRPLFGSDLPQTEETADVLGTFHVLA

ELPADCFGAYIISMATAPSDVLAVELLQRECHVKHPLRVVPLFEKLADLEAAPAAVARLFSIDW

YMDRINGKQEVMIGYSDSGKDAGRLSAAWQMYKAQEELIKVAKHYGVKLTMFHGRGGTVGRGGG

PTHLAILSQPPDTIHGSLRVTVQGEVIEHSFGEELLCFRTLQRYTAATLEHGMHPPISPKPEWR

ALMDEMAVVATKEYRSIVFQEPRFVEYFRSATPETEYGRMNIGSRPSKRKPSGGIESLRAIPWI

FAWTQTRFHLPVWLGFGAAIKHIMQKDIRNIHILREMYNEWPFFRVTLDLLEMVFAKGDPGIAA

VYDKLLVADDLQSFGEQLRKNYEETKELLLQVAGHKDVLEGDPYLKQRLRLRESYITTLNVCQA

YTLKRIRDPSFQVSPQPPLSKEFTDESQPAELVQLNQQSEYAPGLEDTLILTMKGIAAGMQNTG

In SEQ ID NO: 2: i) A at position 770 is a hallmark for 03 and
would be S if C4; and ii) R at position 880 is a hallmark for 03
and would be G if C4.

>SEQ ID NO: 3_Glycine_max (soybean)
MGTRNFEKMASIDAQLRLLAPSKVSDDDKLVEYDALLLDRFLDILQDLHGDDIRETVQDCYELS

AEYEGQNNPQKLEELGNMLTGLDAGDSIVISKSFAHMLNLANLAEEVQIAYRRRIKLLKKGDFA

DENSAITESDIEETFKRLVNQLKKTPQEIFDALKSQTVDLVLTAHPTQSVRRSLLQKHGRIRNC

LTQLYAKDITPDDKQELDEALQREIQAAFRTDEIRRTPPTPQDEMRAGMSYFHETIWKGIPKFL

RRVDTALKNIGINERVPYNAPVIQFSSWMGGDRDGNPRVTPEVTRDVCLLARMMAANLYFSQIE

DLMFELSMWRCNDELRVRSDELLSSSKRDAKHYIEFWKQIPPNEPYRVILGDVRDKLYNTRERA

-continued

```
RQLLANGSSEIPEETTFTNVEQFLEPLELCYRSLCACGDQPIADGSLLDFLRQVSTFGLSLVRL

DIRQESDRHTDVMDAITNHLEIGSYREWSEERRQEWLLSELSGKRPLFGPDLPKTEEIADVLET

FHVIAELPSDSFGAYIISMATAPSDVLSVELLQRECHVKQPLRVVPLFEKLADLEAAPAAVARL

FSIDWYRDRINGKQEVMIGYSDSGKDAGRFSAAWALYKAQEELIKVAKEFGVKLTMFHGRGGTV

GRGGGPTHLAILSQPPDTIHGSLRVTVQGEVIEQSFGEEHLCFRTLQRFTAATLEHGMHPPVAP

KPEWRALMDEMAVIATEEYRSIVFQEPRFVEYFRCATPELEYGRMNIGSRPSKRKPSGGIESLR

AIPWIFAWTQTRFHLPVWLGFGAAFSHVIKKDPKNLQMLQDMYNQWPFFRVSLDLVEMVFAKGD

PGIAALYDKLLVSEELWPFGERLRSMFEETKSLLLQVAGHKDLLEGDPYLKQRLRLRDSYITTL

NVLQAYTLKRIRDPDYHVKLRPHLSKDYMESNKPAAELVKLNPTSDYAPGLEDTLILTMKGIAA

GMQNTG

>SEQ ID NO: 4_Triticum_aestivum (wheat)
MALSAPGGGSGKIERLSSIDAQLRLLVPAKVSEDDKLIEYDALLLDRFLDVLQGLHGDDLREMV

QECYEVAAEYETKHDLEKLDELGEMITSLDPGDSIVIAKAFSHMLNLANLAEEVQIAYRRRVKL

KKGDFADENSAITESDIEETLKRLVFDMKKSPAEVFDALKNQTVDLVLTAHPTQSVRRSLLQKH

SRIRNCLVQLYSKDITPDDKQELDEALQREIQAAFRTDEIRRLSPTPQDHMRAGMSDFHETIWK

GVPKFLRRVDTALKNIGINERVPYNAPLIQFSSWMGGDRDGNPRVTPEVTRDVCLLARMMAANL

YCAQIEDLMFELSMWRCNDELRSRADELHRSSKKDAKHYIEFWKKVPPNEPYRVILGDVRDNLY

NTRERSRELLSSGHSDIPEEATLTNLEQLLEPLELCYRSLCACGDRVIADGTLLDFLRQVSTFG

LSLVKLDIRQESDRHTDALDAITSYLGIGSYREWSEEHRQEWLLSELNGKRPLFGADLPMTEEV

ADVMGAFQVIAELPGDNFGAYVISMATSPSDVLAVELLQRECHIKTPLRVVPLFEKLADLEAAP

AALARLFSIDWYRERINGKQEVMIGYSDSGKDAGRLSAAWQMYKAQEDLVKVAKQFGVKLTMFH

GRGGTVGRGGGPTHLAILSQPPDTINGSLRVTVQGEVIEQSFGEEHLCFRTLQRFTAATLEHGM

RPPISPKPEWRALLDEMAVVATEEYRSIVFQEPRFVEYFRLATPETEYGRMNIGSRPSKRKPSG

GIESLRAIPWIFAWTQTRFHLPVWLGFGGAFKHILKKDIRNFHMLQEMYNEWPFFRVTIDLVEM

VFAKGNPGIAALYDRLLVSEGLQPLGEKLRANYEETQKLLLQVAGHKDLLEGDPYLKQRLRLRD

AYITTMNVCQAYTLKRIRDPDYHVALRPHLSKEVMDTSKPAAELVTLNPASEYAPGLEDTLILT

MKGIAAGLQNTG

>SEQ ID NO: 5_Hordeum vulgare (barley)
MALSAPGGGSGKIERLSSIDAQLRLLVPAKVSEDDKLIEYDALLLDRFLDVLQGLHGDDLREMV

QECYEVAAEYETKHDLEKLDELGEMITSLDPGDSIVIAKAFSHMLNLANLAEEVQIAYRRRVKL

KKGDFADENSAITESDIEETLKRLVFDMKKSPAEVFDALKNQTVDLVLTAHPTQSVRRSLLQKH

SRIRNCLVQLYSKDITPDDKQELDEALQREIQAAFRTDEIRRTQPTPQDEMRAGMSYFHETIWK

GVPKFLRRVDTALKNIGINERVPYNAPLIQFSSWMGGDRDGNPRVTPEVTRDVCLLARMMAANL

YCAQIEDLMFELSMWRCNDELRARADELHRSSKKDAKHYIEFWKKVPPNEPYRVILGDVRDNLY

NTRERSRELLSSGHSDIPEEATLTNLEQLLEPLELCYRSLCACGDRVIADGTLLDFLRQVSTFG

LSLVKLDIRQESDRHTDALDAITSYLGIGSYREWSEERRQEWLLSELNGKRPLFGADLPMTEEV

ADVMGAFQVIAELPGDNFGAYVISMATSPSDVLAVELLQRECHIKTPLRVVPLFEKLADLEAAP

AALARLFSIDWYRERINGKQEVMIGYSDSGKDAGRLSAAWQMYKAQEDLVKVAKQFGVKLTMFH

GRGGTVGRGGGPTHLAILSQPPDTINGSLRVTVQGEVIEQSFGEEHLCFRTLQRFTAATLEHGM

RPPISPKPEWRALLDEMAVVATEEYRSIVFQEPRFVEYFRLATPETEYGRMNIGSRPSKRKPSG

GIESLRAIPWIFAWTQTRFHLPVWLGFGGAFKHILKKDIRNFHMLQEMYNEWPFFRVTIDLVEM
```

-continued

```
VFAKGNPGIAALYDRLLVSEGLQPLGEKLRANYEETQKLLLQVAGHKDLLEGDPYLKQRLRLRD

AYITTMNVCQAYTLKRIRDPDYHVALRPHLSKEVMDTSKPAAELVTLNPASEYAPGLEDTLILT

MKGIAAGLQNTG

>SEQ ID NO: 6_Oryza_sativa (rice)
MAGKVEKMASIDAQLRMLAPAKLSEDDKLVEYDALLLDRFLDILQDLHGDDLRELVQECYEIAA

EYEGKHDSQKLDELGNMLTSLDPGDSIVMAKAFSHMLNLANLAEEVQIAYRRRIKLKKGDFADE

NSALTESDIEETFKRLVVDLKKSPAEVFDALKSQTVDLVLTAHPTQSVRRSLLQKHSRIRNCLV

QLYSKDITPDDKQELDEALQREIQAAFRTDEIRRTQPTPQDEMRAGMSYFHETIWKGVPKFLRR

LDTALKNIGIDERVPYNAPLIQFSSWMGGDRDGNPRVTPEVTRDVCLLARMMASNLYCSQIEDL

MFELSMWRCNDELRARADELHLSSKKDAKHYIEFWKKVPPSEPYRVVLGDVRDKLYNTRERARQ

LLSSGYSDIPEETTLTSVEQFLEPLELCYRSLCDCGDRVIADGTLLDFLRQVSTFGLCLVRLDI

RQESDRHTDVLDAITTYLGIGSYREWSEERRQDWLLSELNGKRPLFGPDLPKTDEIADVLDTFR

VIAELPADNFGAYIISMATAPSDVLAVELLQRECHVKTPLRVVPLFEKLADLESAPAAVARLFS

IDWYRERINGKQEVMIGYSDSGKDAGRLSAAWQLYKSQEELINVAKEFGVKLTMFHGRGGTVGR

GGGPTHLAILSQPPDTIHGSLRVTVQGEVIEQSFGEEHLCFRTLQRFTAATLEHGMHPPIAPKP

EWRALLDEMAVVATKEYRSIVFQEPRFVEYFRLATPEMEYGRMNIGSRPSKRKPSGGIESLRAI

PWIFAWTQTRFHLPVWLGFGSAFKHILEKDIRNLHMLQEMYNEWPFFRVTIDLVEMVFAKGDPG

IAALYDKLLVSEELWPLGEKLRANCEETKQLLLQVAGHKDLLEGDLYLKQRLRLRNAYITTLNV

CQAYTMKRIRDPDYHVTLRPHMSKEIMDWSKPAAELVKLNPTSEYAPGLEDTLILTMKGIAAGM

QNTG

>SEQ ID NO: 7_Sorghum_bicolor (broomcorn)
MAGKLEKMASIDAQLRMLAPAKLSEDDKLVEYDALLLDRFLDILQDLHGEDLRELVQECYEIAA

EYERKHDSEKLDELGNMLTSLDPGDSIVTAKAFSHMLNLANLAEEVQIAYRRRIKLKKGDFADE

NSALTESDIEETFKRLVVDLKKSPAEVFDALKSQTVDLVLTAHPTQSVRRSLLQKHSRIRNCLV

QLCSKDITPDDKQELDEALQREIQAAFRTDEIRRTQPTPQDEMRAGMSYFHETIWKGVPKFLRR

VDTALKNIGIDERVPYNAPLIQFSSWMGGDRDGNPRVTPEVTRDVCLLARMMAANLYCSQIENL

MFELSMWRCNDELRAQADELHRSSKKDAKHYIEFWKKVPPSEPYRVILGDLRDKLYNTRERARQ

LLSSGYSDIPEESTVTNVEQFLEPLELCYRSLCACGDRVIADGSLLDFLRQVSTFGLCLVRLDI

RQESDRHTDVLDAITTYLGIGSYREWSEERRQEWLLSELNGKRPLFGPDLPTTDEIADVLDTFR

VIAELPADNFGAYIISMATAPSDVLAVELLQRECHVKTPLRVVPLFEKLADLEGAPAALARLFS

VDWYRERINGKQEVMIGYSDSGKDAGRLSAAWQLYKAQEELIKVAKKFGVKLTMFHGRGGTVGR

GGGPTHLAILSQPPDTIHGSLRVTVQGEVIEQSFGEEHLCFRTLQRFTAATLEHGMHPPISPKP

EWRALLDEMAVVATKEYRSIVFQEPRFVEYFRLATPEMEYGRMNIGSRPSKRKPSGGIESLRAI

PWIFAWTQTRFHLPVWLGFGAAFKHILEKDIRNLHMLQEMYNEWPFFRVTIDLVEMVFAKGDPG

IAALYDKLLVSSELWPLGEKLRANYEETKRLLLQVAGHKDLLEGDLYLKQRLRLRDAYITTLNV

CQAYTMKRIRDPDYHVTLRPHLSKEIMDWNKPAAELVKLNPTSEYAPGLEDTLILTMKGIAAGM

QNTG

>SEQ ID NO: 8_Consensus
[XXXX]XXEXXXSIDXXLRXLXPXKXSXDDKLXEYDALLXDRFLDXLQXLHGXXX

REXVQXXYEXXAEYEXXXXXXXXLXELTXXXTLXXGDSIVXXXXFXHMLNLANLAEEVQI

AXRRRIKLXKXGDFXDEXSAXTESDXEEEXKXLVXXXXKXXXEXFDALKXQTVDLVLTAH

PTQSVRRSLLQKHXRIRXCLXQLXXKDITXDDKQELDEALQREIQAAFRTDEIXRXXPTP
```

-continued

QDXMRAGMSXFHETIWKGXPKFLRRXDTALKNIGIXERXPYNAPXIQFSSWMGGDRDGNP

RVTPEVTRDVCLLARMMAXXXYXXQIEXLMFEXSMWRCXDELRXXXDEXXXXSXXXXAKH

YIEFWKXXVXXEPYRVXLGDXRDXLYXTRERXXXLLXXGXSXXXXEXTXXXXEQXLEPLE

LCYRSLCXCGDXXIADGXLLDFLRQVSTFGLXLVXLDIRQESDRHTDXXDXITXXLXIGS

YXEWSEEXRQXWLLSELXGKRPLFGXDLPXTXEXADVXXXFXVXAELPXDXFGAYXISMA

TXPSDVLXVELLQRECXXKXPLRVVPLFEKLADLEXAPAAXARLFSXDWYXXRINGKQEV

MIGYSDSGKDAGRXSAAWXXYKXQEXLXXVAKXXGVKLTMFHGRGGTVGXGGGPTHLAIL

SQPPDTIXGSLRVTVQGEVIEXSFGEEXLCFRTLQRXTAATLEHGMXPPSSPKPEWRALX

DEMAVXATXEYRSXVFQEPRFVEYFRXATPEXEYGRMNIGSRPSKRKPSGGIESLRAIPW

IFAWTQTRFHLPVWLGFGXAXXHXXXKDXXNXXXLXXMYXXWPFFRVXXDLXEMVFAKGX

PGIAAXYDXLLVXXXLXXXGEXLRXXXEETXXLXLQXAGHKDXLEGDXYLKQRLRLRXXY

ITTXNVXQAYTXKRIRDPXXXVXXXPXXSKXXXXXXXPAXELXXLNXXSXYAPGLEDTLI

LTMKGIAAGXQNTG, wherein X at position 1, 2, 3 or 4 can be any amino acid or absent.

>SEQ ID NO: 9_Refined_Consensus
[XXXX]XXE[K/R]XXSID[A/V][Q/H]LRXL[V/A]PXK[V/L]S[E/D]DDKL[V/I]EYD

ALL[L/V]DRFLD[I/V]LQ[D/G]LHGX[D/H][L/I]REXVQ[E/D][C/L]YEX[A/S]AE

YEXXXXXX[K/R]LXELGXX[L/I]T[S/G]L[D/P][P/A]GDSIVX[A/S][K/S][A/S]F

[S/A]HMLNLANLAEEVQIA[Y/H]RRRIKLXK[K/R]GDF[A/V]DEXSAXTESD[I/L]EET

[F/L]K[R/K]LVX[D/Q][L/M]XK[S/T][P/R]XE[V/I]FDALK[N/S]QTVDLV[L/F]

TAHPTQSVRRSLLQKH[S/G]RIRXCLXQL[Y/C][S/A]KDIT[P/A]DDKQELDEALQREIQ

AAFRTDEI[R/K]R[T/L]XPTPQD[E/H]MRAGMS[Y/D]FHETIWKG[V/I]PKFLRR[V/I]

DTALKNIGI[N/D]ERXPYNAP[L/V]IQFSSWMGGDRDGNPRVTPEVTRDVCLLARMMA[A/

S][N/T][L/M]Y[C/F]XQIE[D/N]LMFE[L/M]SMWRC[N/S]DELRX[R/Q][A/S]DE[

L/V][H/L]X[S/N]S[K/R][K/R][D/A]XAKHYIEFWKX[V/I]P[P/T]XEPYRV[I/V]

LGD[V/L]RD[K/N]LYXTRER[A/S][R/H]XLLX[S/N]GXS[D/E][I/V][P/L][E/V]

EXTX[T/I][N/S][V/L]EQ[F/L]LEPLELCYRSLCXCGDX[P/V]IADG[S/T]LLDFLRQ

VSTFGLXLV[R/K]LDIRQESDRHTD[V/A][L/M]D[S/A]ITX[Y/H]LXIGSY[R/A]EWS

EEXRQ[D/E]WLLSELXGKRPLFGXDLPXT[E/D]EXADV[L/M]X[T/A]FXV[I/L]AELPX

DXFGAY[I/V]ISMAT[A/S]PSDVL[A/S]VELLQREC[H/R][V/I]KXPLRVVPLFEKLAD

LE[A/G]APAA[L/V]ARLFS[I/V]DWYXXRINGKQEVMIGYSDSGKDAGR[L/F]SAAW[Q/

A][L/M]YK[S/A]QE[E/D]L[I/V][K/N]VAKX[F/Y]GVKLTMFHGR*GGTVGRGGGPTHL*

AILSQPPDTI[H/N]GSLRVTVQGEVIE[Q/H]SFGEE[H/L]LCFRTLQR[F/Y]TAATLEHG

MXPP[I/V][S/A]PKPEWRAL[L/M]DEMAV[V/I]AT[E/K]EYRS[I/V]VFQEPRFVEYF

RXATPEXEYGRMNIGSRPSKRKPSGGIESLRAIPWIFAWTQTRFHLPVWLGFGXA[F/I]XH[I/

V]XXKDX[R/K]NX[H/Q][I/M]L[Q/R][E/D]MY[N/Q]XWPFFRV[T/S][I/L]DLXE

MVFAKG[D/N]PGIAA[L/V]YD[K/R]LLV[S/A]XXL[W/Q][P/S][L/F]GEXLRX[N/M]

XEET[K/Q]XL[L/I]LQ[V/T]AGHKD[L/D]LEGD[P/L]YLKQRLRLR[D/E][A/S]YI

TT[L/M]NV[C/L]QAYT[L/M]KRIRDP[D/S][Y/F][H/Q]]VX[L/P][R/Q]P[H/P]X

-continued

SK[E/D]XX[D/E]X[S/N][K/Q]]PAXEL[V/I]XLN[P/Q]XS[E/D]YAPGLEDTLILTM
KGIAAG[M/L]QNTG, wherein X at position 1, 2, 3 or 4 can be any
amino acid or absent.

SEQ ID NO: 10_(At WITH A651V SUBSTITUTION)
MANRKLEKMASIDVHLRQLVPGKVSEDDKLVEYDALLLDRFLDILQDLHGEDLRETVQELYEHS
AEYEGKHEPKKLEELGSVLTSLDPGDSIVIAKAFSHMLNLANLAEEVQIAYRRRIKKLKKGDFV
DESSATTESDLEETFKKLVGDLNKSPEEIFDALKNQTVDLVLTAHPTQSVRRSLLQKHGRIRDC
LAQLYAKDITPDDKQELDEALQREIQAAFRTDEIKRTPPTPQDEMRAGMSYFHETIWKGVPKFL
RRVDTALKNIGIEERVPYNAPLIQFSSWMGGDRDGNPRVTPEVTRDVCLLARMMAATMYFNQIE
DLMFEMSMWRCNDELRARADEVHANSRKDAAKHYIEFWKSIPTTEPYRVILGDVRDKLYHTRER
AHQLLSNGHSDVPVEATFINLEQFLEPLELCYRSLCSCGDRPIADGSLLDFLRQVSTFGLSLVR
LDIRQESDRHTDVLDAITTHLDIGSYREWSEERRQEWLLSELSGKRPLFGSDLPKTEEIADVLD
TFHVIAELPADSFGAYIISMATAPSDVLAVELLQRECRVKQPLRVVPLFEKLADLEAAPAAVAR
LFSVDWYKNRINGKQEVMIGYSDSGKDAGRLSAAWQLYKAQEELVKVAKEYGVKLTMFHGRGGT
VGRGGGPTHLVILSQPPDTINGSLRVTVQGEVIEQSFGEEHLCFRTLQRFTAATLEHGMRPPIS
PKPEWRALLDEMAVVATEEYRSVVFQEPRFVEYFRLATPELEYGRMNIGSRPSKRKPSGGIESL
RAIPWIFAWTQTRFHLPVWLGFGSAIRHVIEKDVRNLHMLQDMYQHWPFFRVTIDLIEMVFAKG
DPGIAALYDKLLVSEELWPFGEKLRANFEETKKLILQTAGHKDLLEGDPYLKQRLRLRDSYITT
LNVCQAYTLKRIRDPSYHVTLRPHISKEIAESSKPAKELIELNPTSEYAPGLEDTLILTMKGIA
AGLQNTG

SEQ ID NO: 11_(At WITH G678S SUBSTITUTIONS)
MANRKLEKMASIDVHLRQLVPGKVSEDDKLVEYDALLLDRFLDILQDLHGEDLRETVQELYEHS
AEYEGKHEPKKLEELGSVLTSLDPGDSIVIAKAFSHMLNLANLAEEVQIAYRRRIKKLKKGDFV
DESSATTESDLEETFKKLVGDLNKSPEEIFDALKNQTVDLVLTAHPTQSVRRSLLQKHGRIRDC
LAQLYAKDITPDDKQELDEALQREIQAAFRTDEIKRTPPTPQDEMRAGMSYFHETIWKGVPKFL
RRVDTALKNIGIEERVPYNAPLIQFSSWMGGDRDGNPRVTPEVTRDVCLLARMMAATMYFNQIE
DLMFEMSMWRCNDELRARADEVHANSRKDAAKHYIEFWKSIPTTEPYRVILGDVRDKLYHTRER
AHQLLSNGHSDVPVEATFINLEQFLEPLELCYRSLCSCGDRPIADGSLLDFLRQVSTFGLSLVR
LDIRQESDRHTDVLDAITTHLDIGSYREWSEERRQEWLLSELSGKRPLFGSDLPKTEEIADVLD
TFHVIAELPADSFGAYIISMATAPSDVLAVELLQRECRVKQPLRVVPLFEKLADLEAAPAAVAR
LFSVDWYKNRINGKQEVMIGYSDSGKDAGRLSAAWQLYKAQEELVKVAKEYGVKLTMFHGRGGT
VGRGGGPTHLAILSQPPDTINGSLRVTVQGEVIEQSFSEEHLCFRTLQRFTAATLEHGMRPPIS
PKPEWRALLDEMAVVATEEYRSVVFQEPRFVEYFRLATPELEYGRMNIGSRPSKRKPSGGIESL
RAIPWIFAWTQTRFHLPVWLGFGSAIRHVIEKDVRNLHMLQDMYQHWPFFRVTIDLIEMVFAKG
DPGIAALYDKLLVSEELWPFGEKLRANFEETKKLILQTAGHKDLLEGDPYLKQRLRLRDSYITT
LNVCQAYTLKRIRDPSYHVTLRPHISKEIAESSKPAKELIELNPTSEYAPGLEDTLILTMKGIA
AGLQNTG

SEQ ID NO: 12_(At WITH T778I SUBSTITUTION)
MANRKLEKMASIDVHLRQLVPGKVSEDDKLVEYDALLLDRFLDILQDLHGEDLRETVQELYEHS
AEYEGKHEPKKLEELGSVLTSLDPGDSIVIAKAFSHMLNLANLAEEVQIAYRRRIKKLKKGDFV
DESSATTESDLEETFKKLVGDLNKSPEEIFDALKNQTVDLVLTAHPTQSVRRSLLQKHGRIRDC
LAQLYAKDITPDDKQELDEALQREIQAAFRTDEIKRTPPTPQDEMRAGMSYFHETIWKGVPKFL

-continued

RRVDTALKNIGIEERVPYNAPLIQFSSWMGGDRDGNPRVTPEVTRDVCLLARMMAATMYFNQIE

DLMFEMSMWRCNDELRARADEVHANSRKDAAKHYIEFWKSIPTTEPYRVILGDVRDKLYHTRER

AHQLLSNGHSDVPVEATFINLEQFLEPLELCYRSLCSCGDRPIADGSLLDFLRQVSTFGLSLVR

LDIRQESDRHTDVLDAITTHLDIGSYREWSEERRQEWLLSELSGKRPLFGSDLPKTEEIADVLD

TFHVIAELPADSFGAYIISMATAPSDVLAVELLQRECRVKQPLRVVPLFEKLADLEAAPAAVAR

LFSVDWYKNRINGKQEVMIGYSDSGKDAGRLSAAWQLYKAQEELVKVAKEYGVKLTMFHGRGGT

VGRGGGPTHLAILSQPPDTINGSLRVTVQGEVIEQSFGEEHLCFRTLQRFTAATLEHGMRPPIS

PKPEWRALLDEMAVVATEEYRSVVFQEPRFVEYFRLATPELEYGRMNIGSRPSKRKPSGGIESL

RAIPWIFAWIQTRFHLPVWLGFGSAIRHVIEKDVRNLHMLQDMYQHWPFFRVTIDLIEMVFAKG

DPGIAALYDKLLVSEELWPFGEKLRANFEETKKLILQTAGHKDLLEGDPYLKQRLRLRDSYITT

LNVCQAYTLKRIRDPSYHVTLRPHISKEIAESSKPAKELIELNPTSEYAPGLEDTLILTMKGIA

AGLQNTG

SEQ ID NO: 13_(At WITH A651V, G678S, & R886G SUBSTITUTIONS)
MANRKLEKMASIDVHLRQLVPGKVSEDDKLVEYDALLLDRFLDILQDLHGEDLRETVQELYEHS

AEYEGKHEPKKLEELGSVLTSLDPGDSIVIAKAFSHMLNLANLAEEVQIAYRRRIKKLKKGDFV

DESSSATTESDLEETFKKLVGDLNKSPEEIFDALKNQTVDLVLTAHPTQSVRRSLLQKHGRIRDC

LAQLYAKDITPDDKQELDEALQREIQAAFRTDEIKRTPPTPQDEMRAGMSYFHETIWKGVPKFL

RRVDTALKNIGIEERVPYNAPLIQFSSWMGGDRDGNPRVTPEVTRDVCLLARMMAATMYFNQIE

DLMFEMSMWRCNDELRARADEVHANSRKDAAKHYIEFWKSIPTTEPYRVILGDVRDKLYHTRER

AHQLLSNGHSDVPVEATFINLEQFLEPLELCYRSLCSCGDRPIADGSLLDFLRQVSTFGLSLVR

LDIRQESDRHTDVLDAITTHLDIGSYREWSEERRQEWLLSELSGKRPLFGSDLPKTEEIADVLD

TFHVIAELPADSFGAYIISMATAPSDVLAVELLQRECRVKQPLRVVPLFEKLADLEAAPAAVAR

LFSVDWYKNRINGKQEVMIGYSDSGKDAGRLSAAWQLYKAQEELVKVAKEYGVKLTMFHGRGGT

VGRGGGPTHLVILSQPPDTINGSLRVTVQGEVIEQSFSEEHLCFRTLQRFTAATLEHGMRPPIS

PKPEWRALLDEMAVVATEEYRSVVFQEPRFVEYFRLATPELEYGRMNIGSRPSKRKPSGGIESL

RAIPWIFAWTQTRFHLPVWLGFGSAIRHVIEKDVRNLHMLQDMYQHWPFFRVTIDLIEMVFAKG

DPGIAALYDKLLVSEELWPFGEKLRANFEETKKLILQTAGHKDLLEGDPYLKQGLRLRDSYITT

LNVCQAYTLKRIRDPSYHVTLRPHISKEIAESSKPAKELIELNPTSEYAPGLEDTLILTMKGIA

AGLQNTG

SEQ ID NO: 14_(At WITH A651V, G678S, T778I & R886G SUBSTITUTIONS)
MANRKLEKMASIDVHLRQLVPGKVSEDDKLVEYDALLLDRFLDILQDLHGEDLRETVQELYEHS

AEYEGKHEPKKLEELGSVLTSLDPGDSIVIAKAFSHMLNLANLAEEVQIAYRRRIKKLKKGDFV

DESSSATTESDLEETFKKLVGDLNKSPEEIFDALKNQTVDLVLTAHPTQSVRRSLLQKHGRIRDC

LAQLYAKDITPDDKQELDEALQREIQAAFRTDEIKRTPPTPQDEMRAGMSYFHETIWKGVPKFL

RRVDTALKNIGIEERVPYNAPLIQFSSWMGGDRDGNPRVTPEVTRDVCLLARMMAATMYFNQIE

DLMFEMSMWRCNDELRARADEVHANSRKDAAKHYIEFWKSIPTTEPYRVILGDVRDKLYHTRER

AHQLLSNGHSDVPVEATFINLEQFLEPLELCYRSLCSCGDRPIADGSLLDFLRQVSTFGLSLVR

LDIRQESDRHTDVLDAITTHLDIGSYREWSEERRQEWLLSELSGKRPLFGSDLPKTEEIADVLD

TFHVIAELPADSFGAYIISMATAPSDVLAVELLQRECRVKQPLRVVPLFEKLADLEAAPAAVAR

LFSVDWYKNRINGKQEVMIGYSDSGKDAGRLSAAWQLYKAQEELVKVAKEYGVKLTMFHGRGGT

VGRGGGPTHLVILSQPPDTINGSLRVTVQGEVIEQSFSEEHLCFRTLQRFTAATLEHGMRPPIS

PKPEWRALLDEMAVVATEEYRSVVFQEPRFVEYFRLATPELEYGRMNIGSRPSKRKPSGGIESL

```
RAIPWIFAWIQTRFHLPVWLGFGSAIRHVIEKDVRNLHMLQDMYQHWPFFRVTIDLIEMVFAKG

DPGIAALYDKLLVSEELWPFGEKLRANFEETKKLILQTAGHKDLLEGDPYLKQGLRLRDSYITT

LNVCQAYTLKRIRDPSYHVTLRPHISKEIAESSKPAKELIELNPTSEYAPGLEDTLILTMKGIA

AGLQNTG

SEQ ID NO: 15_(Zm_PPC1, C4, shoot, photosynthesis)
MASTKAPGPGEKHHSIDAQLRQLVPGKVSEDDKLIEYDALLVDRFLNILQDLHGPSLREF

VQECYEVSADYEGKGDTTKLGELGAKLTGLAPADAILVASSILHMLNLANLAEEVQIAHR

RRNSKLKKGGFADEGSATTESDIEETLKRLVSEVGKSPEEVFEALKNQTVDLVFTAHPTQ

SARRSLLQKNARIRNCLTQLNAKDITDDDKQELDEALQREIQAAFRTDEIRRAQPTPQDE

MRYGMSYIHETVWKGVPKFLRRVDTALKNIGINERLPYNVSLIRFSSWMGGDRDGNPRVT

PEVTRDVCLLARMMAANLYIDQIEELMFELSMWRCNDELRVRAEELHSSSGSKVTKYYIE

FWKQIPPNEPYRVILGHVRDKLYNTRERARHLLASGVSEISAESSFTSIEEFLEPLELCY

KSLCDCGDKAIADGSLLDLLRQVFTFGLSLVKLDIRQESERHTDVIDAITTHLGIGSYRE

WPEDKRQEWLLSELRGKRPLLPPDLPQTDEIADVIGAFHVLAELPPDSFGPYIISMATAP

SDVLAVELLQRECGVRQPLPVVPLFERLADLQSAPASVERLFSVDWYMDRIKGKQQVMVG

YSDSGKDAGRLSAAWQLYRAQEEMAQVAKRYGVKLTLFHGRGGTVGRGGGPTHLAILSQP

PDTINGSIRVTVQGEVIEFCFGEEHLCFQTLQRFTAATLEHGMHPPVSPKPEWRKLMDEM

AVVATEEYRSVVVKEARFVEYFRSATPETEYGRMNIGSRPAKRRPGGGITTLRAIPWIFS

WTQTRFHLPVWLGVGAAFKFAIDKDVRNFQVLKEMYNEWPFFRVTLDLLEMVFAKGDPGI

AGLYDELLVAEELKPFGKQLRDKYVETQQLLLQIAGHKDILEGDPFLKQGLVLRNPYITT

LNVFQAYTLKRIRDPNFKVTPQPPLSKEFADENKPAGLVKLNPASEYPPGLEDTLILTMK

GIAAGMQNTG
```

In SEQ ID NO: 15: i) S at position 780 is a hallmark for C4 and would be A if C3; and ii) G at position 890 is a hallmark for C4 and would be R if C3.

---

The invention claimed is:

1. A method for producing a maize plant expressing a variant phosphoenolpyruvate carboxylase (PEPC), comprising:
   (a) introducing a clustered regularly interspaced short palindromic repeats (CRISPR) associated protein (Cas9) genome-editing system into a maize plant cell to form a transformed maize plant cell comprising a nucleic acid encoding the variant PEPC comprising (i) an amino acid substitution selected from the group consisting of A651V, G678S, and T778I in the consensus sequence of SEQ ID NO:8, and/or (ii) an amino acid substitution selected from the group consisting of A776S and R886G in the consensus sequence of SEQ ID NO:8; and
   (b) regenerating a maize plant from the transformed plant cell,
   wherein the maize plant expresses the variant PEPC and has enhanced aluminum resistance as compared to a control maize plant that does not express the variant PEPC.

2. A method of enhancing aluminum resistance in a maize plant, comprising:
   (a) crossing a maize plant expressing a variant phosphoenolpyruvate carboxylase (PEPC), wherein the variant PEPC comprises one or more amino acid substitutions selected from the group consisting of A651V, G678S, A776S, T778I, and R886G in the consensus sequence of SEQ ID NO: 8, and wherein the maize plant has enhanced aluminum resistance as compared to a control maize plant that does not express the variant PEPC, with a second maize plant to generate F1 seeds;
   (b) growing F1 plants from the F1 seeds in a phytotoxic substrate, and (c) selecting a maize plant with enhanced aluminum resistance as compared to the second maize plant,
wherein the phytotoxic substrate is a growth substrate having a pH from 2-5 and nanomolar or higher levels of $Al^{3+}$.

3. A method for sequestering carbon in soil, comprising:
growing a maize plant expressing a variant phosphoenolpyruvate carboxylase (PEPC), wherein the variant PEPC comprises one or more amino acid substitutions selected from the group consisting of A651V, G678S, A776S, T778I, and R886G in the consensus sequence of SEQ ID NO: 8, and wherein the maize plant has enhanced aluminum resistance as compared to a control maize plant that does not express the variant PEPC, in soil under conditions effective for production of a carbon-containing organic acid by the maize plant and release of the organic acid from roots of the maize plant into the soil.

4. A method for extracting phosphate from soil, comprising:
growing a maize plant expressing a variant phosphoenolpyruvate carboxylase (PEPC), wherein the variant PEPC comprises one or more amino acid substitutions selected from the group consisting of A651V, G678S, A776S, T778I, and R886G in the consensus sequence of SEQ ID NO: 8, and wherein the maize plant has enhanced aluminum resistance as compared to a control maize plant that does not express the variant PEPC, in soil under conditions effective for production of a carbon-containing organic acid by the maize plant and release of the organic acid from roots of the maize plant into the soil resulting in extraction of inorganic phosphate from the soil by the roots of the maize plant.

5. The method of claim 1, wherein the maize plant has increased carbon-containing organic acid accumulation as compared to the control maize plant that does not express the variant PEPC.

6. The method of claim 1, wherein the maize plant has increased glucose production derived from C4 photosynthesis as compared to the control maize plant that does not express the variant PEPC.

* * * * *

SEQUENCE LISTING

```
<160> NUMBER OF SEQ ID NOS: 15

<210> SEQ ID NO 1
<211> LENGTH: 967
<212> TYPE: PRT
<213> ORGANISM: Arabidopsis thaliana

<400> SEQUENCE: 1

Met Ala Asn Arg Lys Leu Glu Lys Met Ala Ser Ile Asp Val His Leu
1               5                   10                  15

Arg Gln Leu Val Pro Gly Lys Val Ser Glu Asp Asp Lys Leu Val Glu
            20                  25                  30

Tyr Asp Ala Leu Leu Leu Asp Arg Phe Leu Asp Ile Leu Gln Asp Leu
        35                  40                  45

His Gly Glu Asp Leu Arg Glu Thr Val Gln Glu Leu Tyr Glu His Ser
    50                  55                  60

Ala Glu Tyr Glu Gly Lys His Glu Pro Lys Leu Glu Leu Gly
65                  70                  75                  80

Ser Val Leu Thr Ser Leu Asp Pro Gly Asp Ser Ile Val Ile Ala Lys
                85                  90                  95
```

```
Ala Phe Ser His Met Leu Asn Leu Ala Asn Leu Ala Glu Glu Val Gln
                100                 105                 110

Ile Ala Tyr Arg Arg Ile Lys Lys Leu Lys Lys Gly Asp Phe Val
        115                 120                 125

Asp Glu Ser Ser Ala Thr Thr Glu Ser Asp Leu Glu Glu Thr Phe Lys
    130                 135                 140

Lys Leu Val Gly Asp Leu Asn Lys Ser Pro Glu Glu Ile Phe Asp Ala
145                 150                 155                 160

Leu Lys Asn Gln Thr Val Asp Leu Val Leu Thr Ala His Pro Thr Gln
                165                 170                 175

Ser Val Arg Arg Ser Leu Leu Gln Lys His Gly Arg Ile Arg Asp Cys
            180                 185                 190

Leu Ala Gln Leu Tyr Ala Lys Asp Ile Thr Pro Asp Asp Lys Gln Glu
        195                 200                 205

Leu Asp Glu Ala Leu Gln Arg Glu Ile Gln Ala Ala Phe Arg Thr Asp
    210                 215                 220

Glu Ile Lys Arg Thr Pro Pro Thr Pro Gln Asp Glu Met Arg Ala Gly
225                 230                 235                 240

Met Ser Tyr Phe His Glu Thr Ile Trp Lys Gly Val Pro Lys Phe Leu
                245                 250                 255

Arg Arg Val Asp Thr Ala Leu Lys Asn Ile Gly Ile Glu Glu Arg Val
            260                 265                 270

Pro Tyr Asn Ala Pro Leu Ile Gln Phe Ser Ser Trp Met Gly Gly Asp
        275                 280                 285

Arg Asp Gly Asn Pro Arg Val Thr Pro Glu Val Thr Arg Asp Val Cys
    290                 295                 300

Leu Leu Ala Arg Met Met Ala Ala Thr Met Tyr Phe Asn Gln Ile Glu
305                 310                 315                 320

Asp Leu Met Phe Glu Met Ser Met Trp Arg Cys Asn Asp Glu Leu Arg
                325                 330                 335

Ala Arg Ala Asp Glu Val His Ala Asn Ser Arg Lys Asp Ala Ala Lys
            340                 345                 350

His Tyr Ile Glu Phe Trp Lys Ser Ile Pro Thr Thr Glu Pro Tyr Arg
        355                 360                 365

Val Ile Leu Gly Asp Val Arg Asp Lys Leu Tyr His Thr Arg Glu Arg
    370                 375                 380

Ala His Gln Leu Leu Ser Asn Gly His Ser Asp Val Pro Val Glu Ala
385                 390                 395                 400

Thr Phe Ile Asn Leu Glu Gln Phe Leu Glu Pro Leu Glu Leu Cys Tyr
                405                 410                 415

Arg Ser Leu Cys Ser Cys Gly Asp Arg Pro Ile Ala Asp Gly Ser Leu
            420                 425                 430

Leu Asp Phe Leu Arg Gln Val Ser Thr Phe Gly Leu Ser Leu Val Arg
        435                 440                 445

Leu Asp Ile Arg Gln Glu Ser Asp Arg His Thr Asp Val Leu Asp Ala
    450                 455                 460

Ile Thr Thr His Leu Asp Ile Gly Ser Tyr Arg Glu Trp Ser Glu Glu
465                 470                 475                 480

Arg Arg Gln Glu Trp Leu Leu Ser Glu Leu Ser Gly Lys Arg Pro Leu
                485                 490                 495

Phe Gly Ser Asp Leu Pro Lys Thr Glu Glu Ile Ala Asp Val Leu Asp
            500                 505                 510

Thr Phe His Val Ile Ala Glu Leu Pro Ala Asp Ser Phe Gly Ala Tyr
```

-continued

```
            515                 520                 525
Ile Ile Ser Met Ala Thr Ala Pro Ser Asp Val Leu Ala Val Glu Leu
        530                 535                 540
Leu Gln Arg Glu Cys Arg Val Lys Gln Pro Leu Arg Val Val Pro Leu
545                 550                 555                 560
Phe Glu Lys Leu Ala Asp Leu Glu Ala Ala Pro Ala Ala Val Ala Arg
                565                 570                 575
Leu Phe Ser Val Asp Trp Tyr Lys Asn Arg Ile Asn Gly Lys Gln Glu
            580                 585                 590
Val Met Ile Gly Tyr Ser Asp Ser Gly Lys Asp Ala Gly Arg Leu Ser
        595                 600                 605
Ala Ala Trp Gln Leu Tyr Lys Ala Gln Glu Glu Leu Val Lys Val Ala
    610                 615                 620
Lys Glu Tyr Gly Val Lys Leu Thr Met Phe His Gly Arg Gly Gly Thr
625                 630                 635                 640
Val Gly Arg Gly Gly Pro Thr His Leu Ala Ile Leu Ser Gln Pro
                645                 650                 655
Pro Asp Thr Ile Asn Gly Ser Leu Arg Val Thr Val Gln Gly Glu Val
            660                 665                 670
Ile Glu Gln Ser Phe Gly Glu Glu His Leu Cys Phe Arg Thr Leu Gln
        675                 680                 685
Arg Phe Thr Ala Ala Thr Leu Glu His Gly Met Arg Pro Pro Ile Ser
    690                 695                 700
Pro Lys Pro Glu Trp Arg Ala Leu Leu Asp Glu Met Ala Val Val Ala
705                 710                 715                 720
Thr Glu Glu Tyr Arg Ser Val Val Phe Gln Glu Pro Arg Phe Val Glu
                725                 730                 735
Tyr Phe Arg Leu Ala Thr Pro Glu Leu Glu Tyr Gly Arg Met Asn Ile
            740                 745                 750
Gly Ser Arg Pro Ser Lys Arg Lys Pro Ser Gly Gly Ile Glu Ser Leu
        755                 760                 765
Arg Ala Ile Pro Trp Ile Phe Ala Trp Thr Gln Thr Arg Phe His Leu
    770                 775                 780
Pro Val Trp Leu Gly Phe Gly Ser Ala Ile Arg His Val Ile Glu Lys
785                 790                 795                 800
Asp Val Arg Asn Leu His Met Leu Gln Asp Met Tyr Gln His Trp Pro
                805                 810                 815
Phe Phe Arg Val Thr Ile Asp Leu Ile Glu Met Val Phe Ala Lys Gly
            820                 825                 830
Asp Pro Gly Ile Ala Ala Leu Tyr Asp Lys Leu Leu Val Ser Glu Glu
        835                 840                 845
Leu Trp Pro Phe Gly Glu Lys Leu Arg Ala Asn Phe Glu Glu Thr Lys
    850                 855                 860
Lys Leu Ile Leu Gln Thr Ala Gly His Lys Asp Leu Leu Glu Gly Asp
865                 870                 875                 880
Pro Tyr Leu Lys Gln Arg Leu Arg Leu Arg Asp Ser Tyr Ile Thr Thr
                885                 890                 895
Leu Asn Val Cys Gln Ala Tyr Thr Leu Lys Arg Ile Arg Asp Pro Ser
            900                 905                 910
Tyr His Val Thr Leu Arg Pro His Ile Ser Lys Glu Ile Ala Glu Ser
        915                 920                 925
Ser Lys Pro Ala Lys Glu Leu Ile Glu Leu Asn Pro Thr Ser Glu Tyr
    930                 935                 940
```

Ala Pro Gly Leu Glu Asp Thr Leu Ile Leu Thr Met Lys Gly Ile Ala
945                 950                 955                 960

Ala Gly Leu Gln Asn Thr Gly
                965

<210> SEQ ID NO 2
<211> LENGTH: 960
<212> TYPE: PRT
<213> ORGANISM: Zea mays

<400> SEQUENCE: 2

Met Pro Glu Arg His Gln Ser Ile Asp Ala Gln Leu Arg Leu Leu Ala
1               5                   10                  15

Pro Gly Lys Val Ser Glu Asp Lys Leu Val Glu Tyr Asp Ala Leu
            20                  25                  30

Leu Val Asp Arg Phe Leu Asp Ile Leu Gln Asp Leu His Gly Pro His
        35                  40                  45

Leu Arg Glu Phe Val Gln Glu Cys Tyr Glu Leu Ser Ala Glu Tyr Glu
    50                  55                  60

Asn Asp Arg Asp Glu Ala Arg Leu Gly Glu Leu Gly Ser Lys Leu Thr
65                  70                  75                  80

Ser Leu Pro Pro Gly Asp Ser Ile Val Val Ala Ser Phe Ser His
                85                  90                  95

Met Leu Asn Leu Ala Asn Leu Ala Glu Val Gln Ile Ala His Arg
            100                 105                 110

Arg Arg Ile Lys Leu Lys Arg Gly Asp Phe Ala Asp Glu Ala Ser Ala
        115                 120                 125

Pro Thr Glu Ser Asp Ile Glu Glu Thr Leu Lys Arg Leu Val Ser Gln
    130                 135                 140

Leu Gly Lys Ser Arg Glu Glu Val Phe Asp Ala Leu Lys Asn Gln Thr
145                 150                 155                 160

Val Asp Leu Val Phe Thr Ala His Pro Thr Gln Ser Val Arg Arg Ser
                165                 170                 175

Leu Leu Gln Lys His Gly Arg Ile Arg Asn Cys Leu Arg Gln Leu Tyr
            180                 185                 190

Ala Lys Asp Ile Thr Ala Asp Asp Lys Gln Glu Leu Asp Glu Ala Leu
        195                 200                 205

Gln Arg Glu Ile Gln Ala Ala Phe Arg Thr Asp Glu Ile Arg Arg Thr
    210                 215                 220

Pro Pro Thr Pro Gln Asp Glu Met Arg Ala Gly Met Ser Tyr Phe His
225                 230                 235                 240

Glu Thr Ile Trp Lys Gly Val Pro Lys Phe Leu Arg Arg Ile Asp Thr
                245                 250                 255

Ala Leu Lys Asn Ile Gly Ile Asn Glu Arg Leu Pro Tyr Asn Ala Pro
            260                 265                 270

Leu Ile Gln Phe Ser Ser Trp Met Gly Gly Asp Arg Asp Gly Asn Pro
        275                 280                 285

Arg Val Thr Pro Glu Val Thr Arg Asp Val Cys Leu Leu Ala Arg Met
    290                 295                 300

Met Ala Ala Asn Leu Tyr Phe Ser Gln Ile Glu Asp Leu Met Phe Glu
305                 310                 315                 320

Leu Ser Met Trp Arg Cys Ser Asp Glu Leu Arg Ile Arg Ala Asp Glu
                325                 330                 335

Leu His Arg Ser Ser Arg Lys Ala Ala Lys His Tyr Ile Glu Phe Trp

```
                    340                 345                 350
Lys Gln Val Pro Pro Asn Glu Pro Tyr Arg Val Ile Leu Gly Asp Val
                355                 360                 365
Arg Asp Lys Leu Tyr Tyr Thr Arg Glu Arg Ser Arg His Leu Leu Thr
            370                 375                 380
Ser Gly Ile Ser Glu Ile Leu Glu Glu Ala Thr Phe Thr Asn Val Glu
385                 390                 395                 400
Gln Phe Leu Glu Pro Leu Glu Leu Cys Tyr Arg Ser Leu Cys Ala Cys
                405                 410                 415
Gly Asp Lys Pro Ile Ala Asp Gly Ser Leu Leu Asp Phe Leu Arg Gln
                420                 425                 430
Val Ser Thr Phe Gly Leu Ala Leu Val Lys Leu Asp Ile Arg Gln Glu
            435                 440                 445
Ser Asp Arg His Thr Asp Val Leu Asp Ser Ile Thr Thr His Leu Gly
            450                 455                 460
Ile Gly Ser Tyr Ala Glu Trp Ser Glu Lys Arg Gln Asp Trp Leu
465                 470                 475                 480
Leu Ser Glu Leu Arg Gly Lys Arg Pro Leu Phe Gly Ser Asp Leu Pro
                485                 490                 495
Gln Thr Glu Glu Thr Ala Asp Val Leu Gly Thr Phe His Val Leu Ala
                500                 505                 510
Glu Leu Pro Ala Asp Cys Phe Gly Ala Tyr Ile Ile Ser Met Ala Thr
            515                 520                 525
Ala Pro Ser Asp Val Leu Ala Val Glu Leu Leu Gln Arg Glu Cys His
            530                 535                 540
Val Lys His Pro Leu Arg Val Val Pro Leu Phe Glu Lys Leu Ala Asp
545                 550                 555                 560
Leu Glu Ala Ala Pro Ala Ala Val Ala Arg Leu Phe Ser Ile Asp Trp
                565                 570                 575
Tyr Met Asp Arg Ile Asn Gly Lys Gln Glu Val Met Ile Gly Tyr Ser
            580                 585                 590
Asp Ser Gly Lys Asp Ala Gly Arg Leu Ser Ala Ala Trp Gln Met Tyr
            595                 600                 605
Lys Ala Gln Glu Glu Leu Ile Lys Val Ala Lys His Tyr Gly Val Lys
            610                 615                 620
Leu Thr Met Phe His Gly Arg Gly Gly Thr Val Gly Arg Gly Gly Gly
625                 630                 635                 640
Pro Thr His Leu Ala Ile Leu Ser Gln Pro Pro Asp Thr Ile His Gly
                645                 650                 655
Ser Leu Arg Val Thr Val Gln Gly Glu Val Ile Glu His Ser Phe Gly
            660                 665                 670
Glu Glu Leu Leu Cys Phe Arg Thr Leu Gln Arg Tyr Thr Ala Ala Thr
                675                 680                 685
Leu Glu His Gly Met His Pro Pro Ile Ser Pro Lys Pro Glu Trp Arg
            690                 695                 700
Ala Leu Met Asp Glu Met Ala Val Val Ala Thr Lys Glu Tyr Arg Ser
705                 710                 715                 720
Ile Val Phe Gln Glu Pro Arg Phe Val Glu Tyr Phe Arg Ser Ala Thr
                725                 730                 735
Pro Glu Thr Glu Tyr Gly Arg Met Asn Ile Gly Ser Arg Pro Ser Lys
            740                 745                 750
Arg Lys Pro Ser Gly Gly Ile Glu Ser Leu Arg Ala Ile Pro Trp Ile
            755                 760                 765
```

```
Phe Ala Trp Thr Gln Thr Arg Phe His Leu Pro Val Trp Leu Gly Phe
        770                 775                 780

Gly Ala Ala Ile Lys His Ile Met Gln Lys Asp Ile Arg Asn Ile His
785                 790                 795                 800

Ile Leu Arg Glu Met Tyr Asn Glu Trp Pro Phe Phe Arg Val Thr Leu
                805                 810                 815

Asp Leu Leu Glu Met Val Phe Ala Lys Gly Asp Pro Gly Ile Ala Ala
                820                 825                 830

Val Tyr Asp Lys Leu Leu Val Ala Asp Asp Leu Gln Ser Phe Gly Glu
                835                 840                 845

Gln Leu Arg Lys Asn Tyr Glu Glu Thr Lys Leu Leu Leu Gln Val
        850                 855                 860

Ala Gly His Lys Asp Val Leu Glu Gly Asp Pro Tyr Leu Lys Gln Arg
865                 870                 875                 880

Leu Arg Leu Arg Glu Ser Tyr Ile Thr Thr Leu Asn Val Cys Gln Ala
                885                 890                 895

Tyr Thr Leu Lys Arg Ile Arg Asp Pro Ser Phe Gln Val Ser Pro Gln
                900                 905                 910

Pro Pro Leu Ser Lys Glu Phe Thr Asp Glu Ser Gln Pro Ala Glu Leu
                915                 920                 925

Val Gln Leu Asn Gln Gln Ser Glu Tyr Ala Pro Gly Leu Glu Asp Thr
                930                 935                 940

Leu Ile Leu Thr Met Lys Gly Ile Ala Ala Gly Met Gln Asn Thr Gly
945                 950                 955                 960

<210> SEQ ID NO 3
<211> LENGTH: 966
<212> TYPE: PRT
<213> ORGANISM: Glycine max

<400> SEQUENCE: 3

Met Gly Thr Arg Asn Phe Glu Lys Met Ala Ser Ile Asp Ala Gln Leu
1               5                   10                  15

Arg Leu Leu Ala Pro Ser Lys Val Ser Asp Asp Lys Leu Val Glu
        20                  25                  30

Tyr Asp Ala Leu Leu Leu Asp Arg Phe Leu Asp Ile Leu Gln Asp Leu
                35                  40                  45

His Gly Asp Asp Ile Arg Glu Thr Val Gln Asp Cys Tyr Glu Leu Ser
        50                  55                  60

Ala Glu Tyr Glu Gly Gln Asn Asn Pro Gln Lys Leu Glu Glu Leu Gly
65                  70                  75                  80

Asn Met Leu Thr Gly Leu Asp Ala Gly Asp Ser Ile Val Ile Ser Lys
                85                  90                  95

Ser Phe Ala His Met Leu Asn Leu Ala Asn Leu Ala Glu Glu Val Gln
                100                 105                 110

Ile Ala Tyr Arg Arg Ile Lys Leu Leu Lys Lys Gly Asp Phe Ala
        115                 120                 125

Asp Glu Asn Ser Ala Ile Thr Glu Ser Asp Ile Glu Glu Thr Phe Lys
        130                 135                 140

Arg Leu Val Asn Gln Leu Lys Lys Thr Pro Gln Glu Ile Phe Asp Ala
145                 150                 155                 160

Leu Lys Ser Gln Thr Val Asp Leu Val Leu Thr Ala His Pro Thr Gln
                165                 170                 175

Ser Val Arg Arg Ser Leu Leu Gln Lys His Gly Arg Ile Arg Asn Cys
```

```
                180                 185                 190
Leu Thr Gln Leu Tyr Ala Lys Asp Ile Thr Pro Asp Lys Gln Glu
            195                 200                 205
Leu Asp Glu Ala Leu Gln Arg Glu Ile Gln Ala Ala Phe Arg Thr Asp
210                 215                 220
Glu Ile Arg Arg Thr Pro Thr Pro Gln Asp Glu Met Arg Ala Gly
225                 230                 235                 240
Met Ser Tyr Phe His Glu Thr Ile Trp Lys Gly Ile Pro Lys Phe Leu
                245                 250                 255
Arg Arg Val Asp Thr Ala Leu Lys Asn Ile Gly Ile Asn Glu Arg Val
            260                 265                 270
Pro Tyr Asn Ala Pro Val Ile Gln Phe Ser Ser Trp Met Gly Gly Asp
        275                 280                 285
Arg Asp Gly Asn Pro Arg Val Thr Pro Glu Val Thr Arg Asp Val Cys
        290                 295                 300
Leu Leu Ala Arg Met Met Ala Ala Asn Leu Tyr Phe Ser Gln Ile Glu
305                 310                 315                 320
Asp Leu Met Phe Glu Leu Ser Met Trp Arg Cys Asn Asp Glu Leu Arg
                325                 330                 335
Val Arg Ser Asp Glu Leu Leu Ser Ser Lys Arg Asp Ala Lys His
            340                 345                 350
Tyr Ile Glu Phe Trp Lys Gln Ile Pro Pro Asn Glu Pro Tyr Arg Val
        355                 360                 365
Ile Leu Gly Asp Val Arg Asp Lys Leu Tyr Asn Thr Arg Glu Arg Ala
    370                 375                 380
Arg Gln Leu Leu Ala Asn Gly Ser Ser Glu Ile Pro Glu Glu Thr Thr
385                 390                 395                 400
Phe Thr Asn Val Glu Gln Phe Leu Glu Pro Leu Glu Leu Cys Tyr Arg
                405                 410                 415
Ser Leu Cys Ala Cys Gly Asp Gln Pro Ile Ala Asp Gly Ser Leu Leu
            420                 425                 430
Asp Phe Leu Arg Gln Val Ser Thr Phe Gly Leu Ser Leu Val Arg Leu
        435                 440                 445
Asp Ile Arg Gln Glu Ser Asp Arg His Thr Asp Val Met Asp Ala Ile
    450                 455                 460
Thr Asn His Leu Glu Ile Gly Ser Tyr Arg Glu Trp Ser Glu Glu Arg
465                 470                 475                 480
Arg Gln Glu Trp Leu Leu Ser Glu Leu Ser Gly Lys Arg Pro Leu Phe
                485                 490                 495
Gly Pro Asp Leu Pro Lys Thr Glu Glu Ile Ala Asp Val Leu Glu Thr
            500                 505                 510
Phe His Val Ile Ala Glu Leu Pro Ser Asp Ser Phe Gly Ala Tyr Ile
        515                 520                 525
Ile Ser Met Ala Thr Ala Pro Ser Asp Val Leu Ser Val Glu Leu Leu
    530                 535                 540
Gln Arg Glu Cys His Val Lys Gln Pro Leu Arg Val Val Pro Leu Phe
545                 550                 555                 560
Glu Lys Leu Ala Asp Leu Glu Ala Ala Pro Ala Val Ala Arg Leu
                565                 570                 575
Phe Ser Ile Asp Trp Tyr Arg Asp Arg Ile Asn Gly Lys Gln Glu Val
            580                 585                 590
Met Ile Gly Tyr Ser Asp Ser Gly Lys Asp Ala Gly Arg Phe Ser Ala
        595                 600                 605
```

Ala Trp Ala Leu Tyr Lys Ala Gln Glu Glu Leu Ile Lys Val Ala Lys
610                 615                 620

Glu Phe Gly Val Lys Leu Thr Met Phe His Gly Arg Gly Gly Thr Val
625                 630                 635                 640

Gly Arg Gly Gly Gly Pro Thr His Leu Ala Ile Leu Ser Gln Pro Pro
            645                 650                 655

Asp Thr Ile His Gly Ser Leu Arg Val Thr Val Gln Gly Glu Val Ile
            660                 665                 670

Glu Gln Ser Phe Gly Glu Glu His Leu Cys Phe Arg Thr Leu Gln Arg
            675                 680                 685

Phe Thr Ala Ala Thr Leu Glu His Gly Met His Pro Pro Val Ala Pro
690                 695                 700

Lys Pro Glu Trp Arg Ala Leu Met Asp Glu Met Ala Val Ile Ala Thr
705                 710                 715                 720

Glu Glu Tyr Arg Ser Ile Val Phe Gln Glu Pro Arg Phe Val Glu Tyr
                725                 730                 735

Phe Arg Cys Ala Thr Pro Glu Leu Glu Tyr Gly Arg Met Asn Ile Gly
            740                 745                 750

Ser Arg Pro Ser Lys Arg Lys Pro Ser Gly Gly Ile Glu Ser Leu Arg
            755                 760                 765

Ala Ile Pro Trp Ile Phe Ala Trp Thr Gln Thr Arg Phe His Leu Pro
770                 775                 780

Val Trp Leu Gly Phe Gly Ala Ala Phe Ser His Val Ile Lys Lys Asp
785                 790                 795                 800

Pro Lys Asn Leu Gln Met Leu Gln Asp Met Tyr Asn Gln Trp Pro Phe
                805                 810                 815

Phe Arg Val Ser Leu Asp Leu Val Glu Met Val Phe Ala Lys Gly Asp
            820                 825                 830

Pro Gly Ile Ala Ala Leu Tyr Asp Lys Leu Leu Val Ser Glu Glu Leu
            835                 840                 845

Trp Pro Phe Gly Glu Arg Leu Arg Ser Met Phe Glu Glu Thr Lys Ser
850                 855                 860

Leu Leu Leu Gln Val Ala Gly His Lys Asp Leu Leu Glu Gly Asp Pro
865                 870                 875                 880

Tyr Leu Lys Gln Arg Leu Arg Leu Arg Asp Ser Tyr Ile Thr Thr Leu
                885                 890                 895

Asn Val Leu Gln Ala Tyr Thr Leu Lys Arg Ile Arg Asp Pro Asp Tyr
            900                 905                 910

His Val Lys Leu Arg Pro His Leu Ser Lys Asp Tyr Met Glu Ser Asn
            915                 920                 925

Lys Pro Ala Ala Glu Leu Val Lys Leu Asn Pro Thr Ser Asp Tyr Ala
930                 935                 940

Pro Gly Leu Glu Asp Thr Leu Ile Leu Thr Met Lys Gly Ile Ala Ala
945                 950                 955                 960

Gly Met Gln Asn Thr Gly
                965

<210> SEQ ID NO 4
<211> LENGTH: 972
<212> TYPE: PRT
<213> ORGANISM: Triticum aestivum

<400> SEQUENCE: 4

Met Ala Leu Ser Ala Pro Gly Gly Gly Ser Gly Lys Ile Glu Arg Leu

-continued

```
1               5                    10                   15
Ser Ser Ile Asp Ala Gln Leu Arg Leu Leu Val Pro Ala Lys Val Ser
            20                  25              30
Glu Asp Asp Lys Leu Ile Glu Tyr Asp Ala Leu Leu Leu Asp Arg Phe
            35                  40                  45
Leu Asp Val Leu Gln Gly Leu His Gly Asp Asp Leu Arg Glu Met Val
 50                  55                  60
Gln Glu Cys Tyr Glu Val Ala Ala Glu Tyr Glu Thr Lys His Asp Leu
 65                  70                  75                  80
Glu Lys Leu Asp Glu Leu Gly Glu Met Ile Thr Ser Leu Asp Pro Gly
                85                  90                  95
Asp Ser Ile Val Ile Ala Lys Ala Phe Ser His Met Leu Asn Leu Ala
                100                 105                 110
Asn Leu Ala Glu Glu Val Gln Ile Ala Tyr Arg Arg Val Lys Leu
                115                 120                 125
Lys Lys Gly Asp Phe Ala Asp Glu Asn Ser Ala Ile Thr Glu Ser Asp
130                 135                 140
Ile Glu Glu Thr Leu Lys Arg Leu Val Phe Asp Met Lys Lys Ser Pro
145                 150                 155                 160
Ala Glu Val Phe Asp Ala Leu Lys Asn Gln Thr Val Asp Leu Val Leu
                165                 170                 175
Thr Ala His Pro Thr Gln Ser Val Arg Arg Ser Leu Leu Gln Lys His
                180                 185                 190
Ser Arg Ile Arg Asn Cys Leu Val Gln Leu Tyr Ser Lys Asp Ile Thr
                195                 200                 205
Pro Asp Asp Lys Gln Glu Leu Asp Glu Ala Leu Gln Arg Glu Ile Gln
210                 215                 220
Ala Ala Phe Arg Thr Asp Glu Ile Arg Arg Leu Ser Pro Thr Pro Gln
225                 230                 235                 240
Asp His Met Arg Ala Gly Met Ser Asp Phe His Glu Thr Ile Trp Lys
                245                 250                 255
Gly Val Pro Lys Phe Leu Arg Arg Val Asp Thr Ala Leu Lys Asn Ile
                260                 265                 270
Gly Ile Asn Glu Arg Val Pro Tyr Asn Ala Pro Leu Ile Gln Phe Ser
                275                 280                 285
Ser Trp Met Gly Gly Asp Arg Asp Gly Asn Pro Arg Val Thr Pro Glu
                290                 295                 300
Val Thr Arg Asp Val Cys Leu Leu Ala Arg Met Met Ala Ala Asn Leu
305                 310                 315                 320
Tyr Cys Ala Gln Ile Glu Asp Leu Met Phe Glu Leu Ser Met Trp Arg
                325                 330                 335
Cys Asn Asp Glu Leu Arg Ser Arg Ala Asp Glu Leu His Arg Ser Ser
                340                 345                 350
Lys Lys Asp Ala Lys His Tyr Ile Glu Phe Trp Lys Lys Val Pro Pro
                355                 360                 365
Asn Glu Pro Tyr Arg Val Ile Leu Gly Asp Val Arg Asp Asn Leu Tyr
                370                 375                 380
Asn Thr Arg Glu Arg Ser Arg Glu Leu Leu Ser Ser Gly His Ser Asp
385                 390                 395                 400
Ile Pro Glu Glu Ala Thr Leu Thr Asn Leu Glu Gln Leu Leu Glu Pro
                405                 410                 415
Leu Glu Leu Cys Tyr Arg Ser Leu Cys Ala Cys Gly Asp Arg Val Ile
                420                 425                 430
```

```
Ala Asp Gly Thr Leu Leu Asp Phe Leu Arg Gln Val Ser Thr Phe Gly
        435                 440                 445

Leu Ser Leu Val Lys Leu Asp Ile Arg Gln Glu Ser Asp Arg His Thr
    450                 455                 460

Asp Ala Leu Asp Ala Ile Thr Ser Tyr Leu Gly Ile Gly Ser Tyr Arg
465                 470                 475                 480

Glu Trp Ser Glu Glu His Arg Gln Glu Trp Leu Leu Ser Glu Leu Asn
                485                 490                 495

Gly Lys Arg Pro Leu Phe Gly Ala Asp Leu Pro Met Thr Glu Glu Val
            500                 505                 510

Ala Asp Val Met Gly Ala Phe Gln Val Ile Ala Glu Leu Pro Gly Asp
        515                 520                 525

Asn Phe Gly Ala Tyr Val Ile Ser Met Ala Thr Ser Pro Ser Asp Val
    530                 535                 540

Leu Ala Val Glu Leu Leu Gln Arg Glu Cys His Ile Lys Thr Pro Leu
545                 550                 555                 560

Arg Val Val Pro Leu Phe Glu Lys Leu Ala Asp Leu Glu Ala Ala Pro
                565                 570                 575

Ala Ala Leu Ala Arg Leu Phe Ser Ile Asp Trp Tyr Arg Glu Arg Ile
            580                 585                 590

Asn Gly Lys Gln Glu Val Met Ile Gly Tyr Ser Asp Ser Gly Lys Asp
        595                 600                 605

Ala Gly Arg Leu Ser Ala Ala Trp Gln Met Tyr Lys Ala Gln Glu Asp
    610                 615                 620

Leu Val Lys Val Ala Lys Gln Phe Gly Val Lys Leu Thr Met Phe His
625                 630                 635                 640

Gly Arg Gly Gly Thr Val Gly Arg Gly Gly Pro Thr His Leu Ala
                645                 650                 655

Ile Leu Ser Gln Pro Pro Asp Thr Ile Asn Gly Ser Leu Arg Val Thr
            660                 665                 670

Val Gln Gly Glu Val Ile Glu Gln Ser Phe Gly Glu Glu His Leu Cys
        675                 680                 685

Phe Arg Thr Leu Gln Arg Phe Thr Ala Ala Thr Leu Glu His Gly Met
    690                 695                 700

Arg Pro Pro Ile Ser Pro Lys Pro Glu Trp Arg Ala Leu Leu Asp Glu
705                 710                 715                 720

Met Ala Val Val Ala Thr Glu Glu Tyr Arg Ser Ile Val Phe Gln Glu
                725                 730                 735

Pro Arg Phe Val Glu Tyr Phe Arg Leu Ala Thr Pro Glu Thr Glu Tyr
            740                 745                 750

Gly Arg Met Asn Ile Gly Ser Arg Pro Ser Lys Arg Lys Pro Ser Gly
        755                 760                 765

Gly Ile Glu Ser Leu Arg Ala Ile Pro Trp Ile Phe Ala Trp Thr Gln
    770                 775                 780

Thr Arg Phe His Leu Pro Val Trp Leu Gly Phe Gly Gly Ala Phe Lys
785                 790                 795                 800

His Ile Leu Lys Lys Asp Ile Arg Asn Phe His Met Leu Gln Glu Met
                805                 810                 815

Tyr Asn Glu Trp Pro Phe Phe Arg Val Thr Ile Asp Leu Val Glu Met
            820                 825                 830

Val Phe Ala Lys Gly Asn Pro Gly Ile Ala Ala Leu Tyr Asp Arg Leu
        835                 840                 845
```

```
Leu Val Ser Glu Gly Leu Gln Pro Leu Gly Glu Lys Leu Arg Ala Asn
    850                 855                 860

Tyr Glu Glu Thr Gln Lys Leu Leu Gln Val Ala Gly His Lys Asp
865                 870                 875                 880

Leu Leu Glu Gly Asp Pro Tyr Leu Lys Gln Arg Leu Arg Leu Arg Asp
                885                 890                 895

Ala Tyr Ile Thr Thr Met Asn Val Cys Gln Ala Tyr Thr Leu Lys Arg
                900                 905                 910

Ile Arg Asp Pro Asp Tyr His Val Ala Leu Arg Pro His Leu Ser Lys
                915                 920                 925

Glu Val Met Asp Thr Ser Lys Pro Ala Ala Glu Leu Val Thr Leu Asn
930                 935                 940

Pro Ala Ser Glu Tyr Ala Pro Gly Leu Glu Asp Thr Leu Ile Leu Thr
945                 950                 955                 960

Met Lys Gly Ile Ala Ala Gly Leu Gln Asn Thr Gly
                965                 970

<210> SEQ ID NO 5
<211> LENGTH: 972
<212> TYPE: PRT
<213> ORGANISM: Hordeum vulgare

<400> SEQUENCE: 5

Met Ala Leu Ser Ala Pro Gly Gly Gly Ser Gly Lys Ile Glu Arg Leu
1               5                   10                  15

Ser Ser Ile Asp Ala Gln Leu Arg Leu Leu Val Pro Ala Lys Val Ser
                20                  25                  30

Glu Asp Asp Lys Leu Ile Glu Tyr Asp Ala Leu Leu Leu Asp Arg Phe
            35                  40                  45

Leu Asp Val Leu Gln Gly Leu His Gly Asp Asp Leu Arg Glu Met Val
50                  55                  60

Gln Glu Cys Tyr Glu Val Ala Ala Glu Tyr Glu Thr Lys His Asp Leu
65                  70                  75                  80

Glu Lys Leu Asp Glu Leu Gly Glu Met Ile Thr Ser Leu Asp Pro Gly
                85                  90                  95

Asp Ser Ile Val Ile Ala Lys Ala Phe Ser His Met Leu Asn Leu Ala
                100                 105                 110

Asn Leu Ala Glu Glu Val Gln Ile Ala Tyr Arg Arg Arg Val Lys Leu
            115                 120                 125

Lys Lys Gly Asp Phe Ala Asp Glu Asn Ser Ala Ile Thr Glu Ser Asp
130                 135                 140

Ile Glu Glu Thr Leu Lys Arg Leu Val Phe Asp Met Lys Lys Ser Pro
145                 150                 155                 160

Ala Glu Val Phe Asp Ala Leu Lys Asn Gln Thr Val Asp Leu Val Leu
                165                 170                 175

Thr Ala His Pro Thr Gln Ser Val Arg Arg Ser Leu Leu Gln Lys His
                180                 185                 190

Ser Arg Ile Arg Asn Cys Leu Val Gln Leu Tyr Ser Lys Asp Ile Thr
            195                 200                 205

Pro Asp Asp Lys Gln Glu Leu Asp Glu Ala Leu Gln Arg Glu Ile Gln
210                 215                 220

Ala Ala Phe Arg Thr Asp Glu Ile Arg Arg Thr Gln Pro Thr Pro Gln
225                 230                 235                 240

Asp Glu Met Arg Ala Gly Met Ser Tyr Phe His Glu Thr Ile Trp Lys
                245                 250                 255
```

```
Gly Val Pro Lys Phe Leu Arg Arg Val Asp Thr Ala Leu Lys Asn Ile
            260                 265                 270

Gly Ile Asn Glu Arg Val Pro Tyr Asn Ala Pro Leu Ile Gln Phe Ser
            275                 280                 285

Ser Trp Met Gly Gly Asp Arg Asp Gly Asn Pro Arg Val Thr Pro Glu
290                 295                 300

Val Thr Arg Asp Val Cys Leu Leu Ala Arg Met Met Ala Ala Asn Leu
305                 310                 315                 320

Tyr Cys Ala Gln Ile Glu Asp Leu Met Phe Glu Leu Ser Met Trp Arg
                325                 330                 335

Cys Asn Asp Glu Leu Arg Ala Arg Ala Asp Glu Leu His Arg Ser Ser
            340                 345                 350

Lys Lys Asp Ala Lys His Tyr Ile Glu Phe Trp Lys Lys Val Pro Pro
            355                 360                 365

Asn Glu Pro Tyr Arg Val Ile Leu Gly Asp Val Arg Asp Asn Leu Tyr
            370                 375                 380

Asn Thr Arg Glu Arg Ser Arg Glu Leu Leu Ser Ser Gly His Ser Asp
385                 390                 395                 400

Ile Pro Glu Glu Ala Thr Leu Thr Asn Leu Glu Gln Leu Leu Glu Pro
                405                 410                 415

Leu Glu Leu Cys Tyr Arg Ser Leu Cys Ala Cys Gly Asp Arg Val Ile
            420                 425                 430

Ala Asp Gly Thr Leu Leu Asp Phe Leu Arg Gln Val Ser Thr Phe Gly
            435                 440                 445

Leu Ser Leu Val Lys Leu Asp Ile Arg Gln Glu Ser Asp Arg His Thr
450                 455                 460

Asp Ala Leu Asp Ala Ile Thr Ser Tyr Leu Gly Ile Gly Ser Tyr Arg
465                 470                 475                 480

Glu Trp Ser Glu Glu Arg Arg Gln Glu Trp Leu Leu Ser Glu Leu Asn
                485                 490                 495

Gly Lys Arg Pro Leu Phe Gly Ala Asp Leu Pro Met Thr Glu Glu Val
            500                 505                 510

Ala Asp Val Met Gly Ala Phe Gln Val Ile Ala Glu Leu Pro Gly Asp
            515                 520                 525

Asn Phe Gly Ala Tyr Val Ile Ser Met Ala Thr Ser Pro Ser Asp Val
530                 535                 540

Leu Ala Val Glu Leu Leu Gln Arg Glu Cys His Ile Lys Thr Pro Leu
545                 550                 555                 560

Arg Val Val Pro Leu Phe Glu Lys Leu Ala Asp Leu Glu Ala Ala Pro
                565                 570                 575

Ala Ala Leu Ala Arg Leu Phe Ser Ile Asp Trp Tyr Arg Glu Arg Ile
            580                 585                 590

Asn Gly Lys Gln Glu Val Met Ile Gly Tyr Ser Asp Ser Gly Lys Asp
            595                 600                 605

Ala Gly Arg Leu Ser Ala Ala Trp Gln Met Tyr Lys Ala Gln Glu Asp
            610                 615                 620

Leu Val Lys Val Ala Lys Gln Phe Gly Val Lys Leu Thr Met Phe His
625                 630                 635                 640

Gly Arg Gly Gly Thr Val Gly Arg Gly Gly Pro Thr His Leu Ala
                645                 650                 655

Ile Leu Ser Gln Pro Pro Asp Thr Ile Asn Gly Ser Leu Arg Val Thr
            660                 665                 670
```

```
Val Gln Gly Glu Val Ile Glu Gln Ser Phe Gly Glu His Leu Cys
            675                 680                 685

Phe Arg Thr Leu Gln Arg Phe Thr Ala Ala Thr Leu Glu His Gly Met
690                 695                 700

Arg Pro Pro Ile Ser Pro Lys Pro Glu Trp Arg Ala Leu Leu Asp Glu
705                 710                 715                 720

Met Ala Val Val Ala Thr Glu Glu Tyr Arg Ser Ile Val Phe Gln Glu
                725                 730                 735

Pro Arg Phe Val Glu Tyr Phe Arg Leu Ala Thr Pro Glu Thr Glu Tyr
                740                 745                 750

Gly Arg Met Asn Ile Gly Ser Arg Pro Ser Lys Arg Lys Pro Ser Gly
            755                 760                 765

Gly Ile Glu Ser Leu Arg Ala Ile Pro Trp Ile Phe Ala Trp Thr Gln
770                 775                 780

Thr Arg Phe His Leu Pro Val Trp Leu Gly Phe Gly Gly Ala Phe Lys
785                 790                 795                 800

His Ile Leu Lys Lys Asp Ile Arg Asn Phe His Met Leu Gln Glu Met
                805                 810                 815

Tyr Asn Glu Trp Pro Phe Phe Arg Val Thr Ile Asp Leu Val Glu Met
                820                 825                 830

Val Phe Ala Lys Gly Asn Pro Gly Ile Ala Ala Leu Tyr Asp Arg Leu
            835                 840                 845

Leu Val Ser Glu Gly Leu Gln Pro Leu Gly Glu Lys Leu Arg Ala Asn
850                 855                 860

Tyr Glu Glu Thr Gln Lys Leu Leu Gln Val Ala Gly His Lys Asp
865                 870                 875                 880

Leu Leu Glu Gly Asp Pro Tyr Leu Lys Gln Arg Leu Arg Leu Arg Asp
                885                 890                 895

Ala Tyr Ile Thr Thr Met Asn Val Cys Gln Ala Tyr Thr Leu Lys Arg
                900                 905                 910

Ile Arg Asp Pro Asp Tyr His Val Ala Leu Arg Pro His Leu Ser Lys
            915                 920                 925

Glu Val Met Asp Thr Ser Lys Pro Ala Ala Glu Leu Val Thr Leu Asn
930                 935                 940

Pro Ala Ser Glu Tyr Ala Pro Gly Leu Glu Asp Thr Leu Ile Leu Thr
945                 950                 955                 960

Met Lys Gly Ile Ala Ala Gly Leu Gln Asn Thr Gly
                965                 970

<210> SEQ ID NO 6
<211> LENGTH: 964
<212> TYPE: PRT
<213> ORGANISM: Oryza sativa

<400> SEQUENCE: 6

Met Ala Gly Lys Val Glu Lys Met Ala Ser Ile Asp Ala Gln Leu Arg
1               5                   10                  15

Met Leu Ala Pro Ala Lys Leu Ser Glu Asp Asp Lys Leu Val Glu Tyr
            20                  25                  30

Asp Ala Leu Leu Leu Asp Arg Phe Leu Asp Ile Leu Gln Asp Leu His
        35                  40                  45

Gly Asp Asp Leu Arg Glu Leu Val Gln Glu Cys Tyr Glu Ile Ala Ala
    50                  55                  60

Glu Tyr Glu Gly Lys His Asp Ser Gln Lys Leu Asp Glu Leu Gly Asn
65                  70                  75                  80
```

-continued

```
Met Leu Thr Ser Leu Asp Pro Gly Asp Ser Ile Val Met Ala Lys Ala
                85                  90                  95

Phe Ser His Met Leu Asn Leu Ala Asn Leu Ala Glu Glu Val Gln Ile
            100                 105                 110

Ala Tyr Arg Arg Ile Lys Leu Lys Lys Gly Asp Phe Ala Asp Glu
        115                 120                 125

Asn Ser Ala Leu Thr Glu Ser Asp Ile Glu Glu Thr Phe Lys Arg Leu
    130                 135                 140

Val Val Asp Leu Lys Lys Ser Pro Ala Glu Val Phe Asp Ala Leu Lys
145                 150                 155                 160

Ser Gln Thr Val Asp Leu Val Leu Thr Ala His Pro Thr Gln Ser Val
                165                 170                 175

Arg Arg Ser Leu Leu Gln Lys His Ser Arg Ile Arg Asn Cys Leu Val
            180                 185                 190

Gln Leu Tyr Ser Lys Asp Ile Thr Pro Asp Asp Lys Gln Glu Leu Asp
        195                 200                 205

Glu Ala Leu Gln Arg Glu Ile Gln Ala Ala Phe Arg Thr Asp Glu Ile
    210                 215                 220

Arg Arg Thr Gln Pro Thr Pro Gln Asp Glu Met Arg Ala Gly Met Ser
225                 230                 235                 240

Tyr Phe His Glu Thr Ile Trp Lys Gly Val Pro Lys Phe Leu Arg Arg
                245                 250                 255

Leu Asp Thr Ala Leu Lys Asn Ile Gly Ile Asp Glu Arg Val Pro Tyr
            260                 265                 270

Asn Ala Pro Leu Ile Gln Phe Ser Ser Trp Met Gly Gly Asp Arg Asp
        275                 280                 285

Gly Asn Pro Arg Val Thr Pro Glu Val Thr Arg Asp Val Cys Leu Leu
    290                 295                 300

Ala Arg Met Met Ala Ser Asn Leu Tyr Cys Ser Gln Ile Glu Asp Leu
305                 310                 315                 320

Met Phe Glu Leu Ser Met Trp Arg Cys Asn Asp Glu Leu Arg Ala Arg
                325                 330                 335

Ala Asp Glu Leu His Leu Ser Ser Lys Lys Asp Ala Lys His Tyr Ile
            340                 345                 350

Glu Phe Trp Lys Lys Val Pro Pro Ser Glu Pro Tyr Arg Val Val Leu
        355                 360                 365

Gly Asp Val Arg Asp Lys Leu Tyr Asn Thr Arg Glu Arg Ala Arg Gln
    370                 375                 380

Leu Leu Ser Ser Gly Tyr Ser Asp Ile Pro Glu Glu Thr Thr Leu Thr
385                 390                 395                 400

Ser Val Glu Gln Phe Leu Glu Pro Leu Glu Leu Cys Tyr Arg Ser Leu
                405                 410                 415

Cys Asp Cys Gly Asp Arg Val Ile Ala Asp Gly Thr Leu Leu Asp Phe
            420                 425                 430

Leu Arg Gln Val Ser Thr Phe Gly Leu Cys Leu Val Arg Leu Asp Ile
        435                 440                 445

Arg Gln Glu Ser Asp Arg His Thr Asp Val Leu Asp Ala Ile Thr Thr
    450                 455                 460

Tyr Leu Gly Ile Gly Ser Tyr Arg Glu Trp Ser Glu Arg Arg Gln
465                 470                 475                 480

Asp Trp Leu Leu Ser Glu Leu Asn Gly Lys Arg Pro Leu Phe Gly Pro
                485                 490                 495
```

```
Asp Leu Pro Lys Thr Asp Glu Ile Ala Asp Val Leu Asp Thr Phe Arg
            500                 505                 510

Val Ile Ala Glu Leu Pro Ala Asp Asn Phe Gly Ala Tyr Ile Ile Ser
        515                 520                 525

Met Ala Thr Ala Pro Ser Asp Val Leu Ala Val Glu Leu Leu Gln Arg
    530                 535                 540

Glu Cys His Val Lys Thr Pro Leu Arg Val Val Pro Leu Phe Glu Lys
545                 550                 555                 560

Leu Ala Asp Leu Glu Ser Ala Pro Ala Ala Val Ala Arg Leu Phe Ser
                565                 570                 575

Ile Asp Trp Tyr Arg Glu Arg Ile Asn Gly Lys Gln Glu Val Met Ile
            580                 585                 590

Gly Tyr Ser Asp Ser Gly Lys Asp Ala Gly Arg Leu Ser Ala Ala Trp
        595                 600                 605

Gln Leu Tyr Lys Ser Gln Glu Glu Leu Ile Asn Val Ala Lys Glu Phe
    610                 615                 620

Gly Val Lys Leu Thr Met Phe His Gly Arg Gly Gly Thr Val Gly Arg
625                 630                 635                 640

Gly Gly Gly Pro Thr His Leu Ala Ile Leu Ser Gln Pro Pro Asp Thr
                645                 650                 655

Ile His Gly Ser Leu Arg Val Thr Val Gln Gly Glu Val Ile Glu Gln
            660                 665                 670

Ser Phe Gly Glu Glu His Leu Cys Phe Arg Thr Leu Gln Arg Phe Thr
        675                 680                 685

Ala Ala Thr Leu Glu His Gly Met His Pro Pro Ile Ala Pro Lys Pro
    690                 695                 700

Glu Trp Arg Ala Leu Leu Asp Glu Met Ala Val Val Ala Thr Lys Glu
705                 710                 715                 720

Tyr Arg Ser Ile Val Phe Gln Glu Pro Arg Phe Val Glu Tyr Phe Arg
                725                 730                 735

Leu Ala Thr Pro Glu Met Glu Tyr Gly Arg Met Asn Ile Gly Ser Arg
            740                 745                 750

Pro Ser Lys Arg Lys Pro Ser Gly Gly Ile Glu Ser Leu Arg Ala Ile
        755                 760                 765

Pro Trp Ile Phe Ala Trp Thr Gln Thr Arg Phe His Leu Pro Val Trp
770                 775                 780

Leu Gly Phe Gly Ser Ala Phe Lys His Ile Leu Glu Lys Asp Ile Arg
785                 790                 795                 800

Asn Leu His Met Leu Gln Glu Met Tyr Asn Glu Trp Pro Phe Phe Arg
                805                 810                 815

Val Thr Ile Asp Leu Val Glu Met Val Phe Ala Lys Gly Asp Pro Gly
            820                 825                 830

Ile Ala Ala Leu Tyr Asp Lys Leu Leu Val Ser Glu Glu Leu Trp Pro
        835                 840                 845

Leu Gly Glu Lys Leu Arg Ala Asn Cys Glu Glu Thr Lys Gln Leu Leu
850                 855                 860

Leu Gln Val Ala Gly His Lys Asp Leu Leu Glu Gly Asp Leu Tyr Leu
865                 870                 875                 880

Lys Gln Arg Leu Arg Leu Arg Asn Ala Tyr Ile Thr Thr Leu Asn Val
                885                 890                 895

Cys Gln Ala Tyr Thr Met Lys Arg Ile Arg Asp Pro Asp Tyr His Val
            900                 905                 910

Thr Leu Arg Pro His Met Ser Lys Glu Ile Met Asp Trp Ser Lys Pro
```

```
                915                 920                 925
Ala Ala Glu Leu Val Lys Leu Asn Pro Thr Ser Glu Tyr Ala Pro Gly
        930                 935                 940

Leu Glu Asp Thr Leu Ile Leu Thr Met Lys Gly Ile Ala Ala Gly Met
945                 950                 955                 960

Gln Asn Thr Gly

<210> SEQ ID NO 7
<211> LENGTH: 964
<212> TYPE: PRT
<213> ORGANISM: Sorghum bicolor

<400> SEQUENCE: 7

Met Ala Gly Lys Leu Glu Lys Met Ala Ser Ile Asp Ala Gln Leu Arg
1               5                  10                  15

Met Leu Ala Pro Ala Lys Leu Ser Glu Asp Asp Lys Leu Val Glu Tyr
            20                  25                  30

Asp Ala Leu Leu Leu Asp Arg Phe Leu Asp Ile Leu Gln Asp Leu His
        35                  40                  45

Gly Glu Asp Leu Arg Glu Leu Val Gln Glu Cys Tyr Glu Ile Ala Ala
    50                  55                  60

Glu Tyr Glu Arg Lys His Asp Ser Glu Lys Leu Asp Glu Leu Gly Asn
65                  70                  75                  80

Met Leu Thr Ser Leu Asp Pro Gly Asp Ser Ile Val Thr Ala Lys Ala
                85                  90                  95

Phe Ser His Met Leu Asn Leu Ala Asn Leu Ala Glu Glu Val Gln Ile
            100                 105                 110

Ala Tyr Arg Arg Arg Ile Lys Leu Lys Lys Gly Asp Phe Ala Asp Glu
        115                 120                 125

Asn Ser Ala Leu Thr Glu Ser Asp Ile Glu Glu Thr Phe Lys Arg Leu
    130                 135                 140

Val Val Asp Leu Lys Lys Ser Pro Ala Glu Val Phe Asp Ala Leu Lys
145                 150                 155                 160

Ser Gln Thr Val Asp Leu Val Leu Thr Ala His Pro Thr Gln Ser Val
                165                 170                 175

Arg Arg Ser Leu Leu Gln Lys His Ser Arg Ile Arg Asn Cys Leu Val
            180                 185                 190

Gln Leu Cys Ser Lys Asp Ile Thr Pro Asp Asp Lys Gln Glu Leu Asp
        195                 200                 205

Glu Ala Leu Gln Arg Glu Ile Gln Ala Ala Phe Arg Thr Asp Glu Ile
    210                 215                 220

Arg Arg Thr Gln Pro Thr Pro Gln Asp Glu Met Arg Ala Gly Met Ser
225                 230                 235                 240

Tyr Phe His Glu Thr Ile Trp Lys Gly Val Pro Lys Phe Leu Arg Arg
                245                 250                 255

Val Asp Thr Ala Leu Lys Asn Ile Gly Ile Asp Glu Arg Val Pro Tyr
            260                 265                 270

Asn Ala Pro Leu Ile Gln Phe Ser Ser Trp Met Gly Gly Asp Arg Asp
        275                 280                 285

Gly Asn Pro Arg Val Thr Pro Glu Val Thr Arg Asp Val Cys Leu Leu
    290                 295                 300

Ala Arg Met Met Ala Ala Asn Leu Tyr Cys Ser Gln Ile Glu Asn Leu
305                 310                 315                 320

Met Phe Glu Leu Ser Met Trp Arg Cys Asn Asp Glu Leu Arg Ala Gln
```

```
                    325                 330                 335
Ala Asp Glu Leu His Arg Ser Ser Lys Lys Asp Ala Lys His Tyr Ile
                340                 345                 350
Glu Phe Trp Lys Lys Val Pro Pro Ser Glu Pro Tyr Arg Val Ile Leu
                355                 360                 365
Gly Asp Leu Arg Asp Lys Leu Tyr Asn Thr Arg Glu Arg Ala Arg Gln
                370                 375                 380
Leu Leu Ser Ser Gly Tyr Ser Asp Ile Pro Glu Glu Ser Thr Val Thr
385                 390                 395                 400
Asn Val Glu Gln Phe Leu Glu Pro Leu Glu Leu Cys Tyr Arg Ser Leu
                405                 410                 415
Cys Ala Cys Gly Asp Arg Val Ile Ala Asp Gly Ser Leu Leu Asp Phe
                420                 425                 430
Leu Arg Gln Val Ser Thr Phe Gly Leu Cys Leu Val Arg Leu Asp Ile
                435                 440                 445
Arg Gln Glu Ser Asp Arg His Thr Asp Val Leu Asp Ala Ile Thr Thr
                450                 455                 460
Tyr Leu Gly Ile Gly Ser Tyr Arg Glu Trp Ser Glu Glu Arg Arg Gln
465                 470                 475                 480
Glu Trp Leu Leu Ser Glu Leu Asn Gly Lys Arg Pro Leu Phe Gly Pro
                485                 490                 495
Asp Leu Pro Thr Thr Asp Glu Ile Ala Asp Val Leu Asp Thr Phe Arg
                500                 505                 510
Val Ile Ala Glu Leu Pro Ala Asp Asn Phe Gly Ala Tyr Ile Ile Ser
                515                 520                 525
Met Ala Thr Ala Pro Ser Asp Val Leu Ala Val Glu Leu Leu Gln Arg
                530                 535                 540
Glu Cys His Val Lys Thr Pro Leu Arg Val Val Pro Leu Phe Glu Lys
545                 550                 555                 560
Leu Ala Asp Leu Glu Gly Ala Pro Ala Ala Leu Ala Arg Leu Phe Ser
                565                 570                 575
Val Asp Trp Tyr Arg Glu Arg Ile Asn Gly Lys Gln Glu Val Met Ile
                580                 585                 590
Gly Tyr Ser Asp Ser Gly Lys Asp Ala Gly Arg Leu Ser Ala Ala Trp
                595                 600                 605
Gln Leu Tyr Lys Ala Gln Glu Glu Leu Ile Lys Val Ala Lys Lys Phe
                610                 615                 620
Gly Val Lys Leu Thr Met Phe His Gly Arg Gly Gly Thr Val Gly Arg
625                 630                 635                 640
Gly Gly Gly Pro Thr His Leu Ala Ile Leu Ser Gln Pro Pro Asp Thr
                645                 650                 655
Ile His Gly Ser Leu Arg Val Thr Val Gln Gly Glu Val Ile Glu Gln
                660                 665                 670
Ser Phe Gly Glu Glu His Leu Cys Phe Arg Thr Leu Gln Arg Phe Thr
                675                 680                 685
Ala Ala Thr Leu Glu His Gly Met His Pro Pro Ile Ser Pro Lys Pro
                690                 695                 700
Glu Trp Arg Ala Leu Leu Asp Glu Met Ala Val Val Ala Thr Lys Glu
705                 710                 715                 720
Tyr Arg Ser Ile Val Phe Gln Glu Pro Arg Phe Val Glu Tyr Phe Arg
                725                 730                 735
Leu Ala Thr Pro Glu Met Glu Tyr Gly Arg Met Asn Ile Gly Ser Arg
                740                 745                 750
```

```
Pro Ser Lys Arg Lys Pro Ser Gly Gly Ile Glu Ser Leu Arg Ala Ile
        755                 760                 765

Pro Trp Ile Phe Ala Trp Thr Gln Thr Arg Phe His Leu Pro Val Trp
770                 775                 780

Leu Gly Phe Gly Ala Ala Phe Lys His Ile Leu Glu Lys Asp Ile Arg
785                 790                 795                 800

Asn Leu His Met Leu Gln Glu Met Tyr Asn Glu Trp Pro Phe Phe Arg
                805                 810                 815

Val Thr Ile Asp Leu Val Glu Met Val Phe Ala Lys Gly Asp Pro Gly
                820                 825                 830

Ile Ala Ala Leu Tyr Asp Lys Leu Leu Val Ser Ser Glu Leu Trp Pro
                835                 840                 845

Leu Gly Glu Lys Leu Arg Ala Asn Tyr Glu Glu Thr Lys Arg Leu Leu
            850                 855                 860

Leu Gln Val Ala Gly His Lys Asp Leu Leu Glu Gly Asp Leu Tyr Leu
865                 870                 875                 880

Lys Gln Arg Leu Arg Leu Arg Asp Ala Tyr Ile Thr Thr Leu Asn Val
                885                 890                 895

Cys Gln Ala Tyr Thr Met Lys Arg Ile Arg Asp Pro Ser Tyr His Val
                900                 905                 910

Thr Leu Arg Pro His Leu Ser Lys Glu Ile Met Asp Trp Asn Lys Pro
            915                 920                 925

Ala Ala Glu Leu Val Lys Leu Asn Pro Thr Ser Glu Tyr Ala Pro Gly
            930                 935                 940

Leu Glu Asp Thr Leu Ile Leu Thr Met Lys Gly Ile Ala Ala Gly Met
945                 950                 955                 960

Gln Asn Thr Gly

<210> SEQ ID NO 8
<211> LENGTH: 967
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4
<223> OTHER INFORMATION: Xaa = Any Amino Acid and can be present or
      absent
<220> FEATURE:
<221> NAME/KEY: VARIANT
<222> LOCATION: 5, 6, 8, 9, 10, 14, 15, 18, 20, 22, 24, 26, 31,
      38, 44, 47, 51, 52, 53, 56, 59, 60, 63, 64, 69, 70, 71,
      72, 73, 74, 75, 77, 81, 82, 83, 85, 87, 88, 94, 95, 96,
      97, 99, 115, 122, 124, 128, 131, 134, 139, 143, 145, 148,
      149, 150, 151, 153, 154, 155, 157, 163, 187, 191, 194, 197, 198,
      203, 227, 229, 230, 236, 243, 252, 259, 269, 272, 278, 312,
      313, 314, 316, 317, 321, 326, 332, 337, 338, 339, 342, 343,
      344, 345, 347, 348, 349, 350, 360, 361, 363, 364, 370, 374,
      377, 380, 385, 386, 387, 390, 391, 393, 395, 396, 397, 398,
      400, 402, 403, 404, 405, 408, 421, 425, 426, 431, 445, 448,
      461, 462, 464, 467, 468, 470, 475, 481, 484, 491, 499, 503,
      505, 507, 511, 512, 513, 515, 517, 522, 524, 529, 535, 541,
      550, 551, 553, 569, 574, 580, 584, 585, 607, 612, 613, 616,
      619, 621, 622, 626, 627, 643, 661, 675, 681, 690, 700, 713,
      719, 722, 727, 740, 745, 792, 794, 795, 797, 798, 799, 802,
      803, 805, 806, 807, 809, 810, 813, 814, 821, 822, 825, 833,
      839, 842, 846, 847, 848, 850, 851, 852, 855, 858, 859, 860,
      864, 865, 867, 870, 876, 881, 891, 892, 897, 900, 905, 912,
      913, 914, 916, 917, 918, 920, 921, 924, 925, 926, 927, 928,
      929, 930, 933, 936, 937, 940, 941, 943, 963
<223> OTHER INFORMATION: Xaa = Any Amino Acid

<400> SEQUENCE: 8
```

-continued

```
Xaa Xaa Xaa Xaa Xaa Xaa Glu Xaa Xaa Xaa Ser Ile Asp Xaa Xaa Leu
1               5                   10                  15

Arg Xaa Leu Xaa Pro Xaa Lys Xaa Ser Xaa Asp Asp Lys Leu Xaa Glu
            20                  25                  30

Tyr Asp Ala Leu Leu Xaa Asp Arg Phe Leu Asp Xaa Leu Gln Xaa Leu
        35                  40                  45

His Gly Xaa Xaa Xaa Arg Glu Xaa Val Gln Xaa Xaa Tyr Glu Xaa Xaa
    50                  55                  60

Ala Glu Tyr Glu Xaa Xaa Xaa Xaa Xaa Xaa Xaa Leu Xaa Glu Leu Thr
65                  70                  75                  80

Xaa Xaa Xaa Thr Xaa Leu Xaa Xaa Gly Asp Ser Ile Val Xaa Xaa Xaa
                85                  90                  95

Xaa Phe Xaa His Met Leu Asn Leu Ala Asn Leu Ala Glu Glu Val Gln
            100                 105                 110

Ile Ala Xaa Arg Arg Arg Ile Lys Leu Xaa Lys Xaa Gly Asp Phe Xaa
        115                 120                 125

Asp Glu Xaa Ser Ala Xaa Thr Glu Ser Asp Xaa Glu Glu Glu Xaa Lys
    130                 135                 140

Xaa Leu Val Xaa Xaa Xaa Xaa Lys Xaa Xaa Xaa Glu Xaa Phe Asp Ala
145                 150                 155                 160

Leu Lys Xaa Gln Thr Val Asp Leu Val Leu Thr Ala His Pro Thr Gln
                165                 170                 175

Ser Val Arg Arg Ser Leu Leu Gln Lys His Xaa Arg Ile Arg Xaa Cys
            180                 185                 190

Leu Xaa Gln Leu Xaa Xaa Lys Asp Ile Thr Xaa Asp Asp Lys Gln Glu
        195                 200                 205

Leu Asp Glu Ala Leu Gln Arg Glu Ile Gln Ala Ala Phe Arg Thr Asp
    210                 215                 220

Glu Ile Xaa Arg Xaa Xaa Pro Thr Pro Gln Asp Xaa Met Arg Ala Gly
225                 230                 235                 240

Met Ser Xaa Phe His Glu Thr Ile Trp Lys Gly Xaa Pro Lys Phe Leu
                245                 250                 255

Arg Arg Xaa Asp Thr Ala Leu Lys Asn Ile Gly Ile Xaa Glu Arg Xaa
            260                 265                 270

Pro Tyr Asn Ala Pro Xaa Ile Gln Phe Ser Ser Trp Met Gly Gly Asp
        275                 280                 285

Arg Asp Gly Asn Pro Arg Val Thr Pro Glu Val Thr Arg Asp Val Cys
    290                 295                 300

Leu Leu Ala Arg Met Met Ala Xaa Xaa Xaa Tyr Xaa Xaa Gln Ile Glu
305                 310                 315                 320

Xaa Leu Met Phe Glu Xaa Ser Met Trp Arg Cys Xaa Asp Glu Leu Arg
                325                 330                 335

Xaa Xaa Xaa Asp Glu Xaa Xaa Xaa Xaa Ser Xaa Xaa Xaa Xaa Ala Lys
            340                 345                 350

His Tyr Ile Glu Phe Trp Lys Xaa Xaa Val Xaa Xaa Glu Pro Tyr Arg
        355                 360                 365

Val Xaa Leu Gly Asp Xaa Arg Asp Xaa Leu Tyr Xaa Thr Arg Glu Arg
    370                 375                 380

Xaa Xaa Xaa Leu Leu Xaa Xaa Gly Xaa Ser Xaa Xaa Xaa Xaa Glu Xaa
385                 390                 395                 400

Thr Xaa Xaa Xaa Xaa Glu Gln Xaa Leu Glu Pro Leu Glu Leu Cys Tyr
                405                 410                 415
```

```
Arg Ser Leu Cys Xaa Cys Gly Asp Xaa Xaa Ile Ala Asp Gly Xaa Leu
                420             425                 430

Leu Asp Phe Leu Arg Gln Val Ser Thr Phe Gly Leu Xaa Leu Val Xaa
            435                 440                 445

Leu Asp Ile Arg Gln Glu Ser Asp Arg His Thr Asp Xaa Xaa Asp Xaa
450                 455                 460

Ile Thr Xaa Xaa Leu Xaa Ile Gly Ser Tyr Xaa Glu Trp Ser Glu Glu
465             470                 475                 480

Xaa Arg Gln Xaa Trp Leu Leu Ser Glu Leu Xaa Gly Lys Arg Pro Leu
                485                 490                 495

Phe Gly Xaa Asp Leu Pro Xaa Thr Xaa Glu Xaa Ala Asp Val Xaa Xaa
            500                 505                 510

Xaa Phe Xaa Val Xaa Ala Glu Leu Pro Xaa Asp Xaa Phe Gly Ala Tyr
        515                 520                 525

Xaa Ile Ser Met Ala Thr Xaa Pro Ser Asp Val Leu Xaa Val Glu Leu
530                 535                 540

Leu Gln Arg Glu Cys Xaa Xaa Lys Xaa Pro Leu Arg Val Val Pro Leu
545                 550                 555                 560

Phe Glu Lys Leu Ala Asp Leu Glu Xaa Ala Pro Ala Ala Xaa Ala Arg
            565                 570                 575

Leu Phe Ser Xaa Asp Trp Tyr Xaa Xaa Arg Ile Asn Gly Lys Gln Glu
            580                 585                 590

Val Met Ile Gly Tyr Ser Asp Ser Gly Lys Asp Ala Gly Arg Xaa Ser
            595                 600                 605

Ala Ala Trp Xaa Xaa Tyr Lys Xaa Gln Glu Xaa Leu Xaa Xaa Val Ala
610                 615                 620

Lys Xaa Xaa Gly Val Lys Leu Thr Met Phe His Gly Arg Gly Gly Thr
625                 630                 635                 640

Val Gly Xaa Gly Gly Gly Pro Thr His Leu Ala Ile Leu Ser Gln Pro
            645                 650                 655

Pro Asp Thr Ile Xaa Gly Ser Leu Arg Val Thr Val Gln Gly Glu Val
                660                 665                 670

Ile Glu Xaa Ser Phe Gly Glu Glu Xaa Leu Cys Phe Arg Thr Leu Gln
        675                 680                 685

Arg Xaa Thr Ala Ala Thr Leu Glu His Gly Met Xaa Pro Ser Ser
    690                 695                 700

Pro Lys Pro Glu Trp Arg Ala Leu Xaa Asp Glu Met Ala Val Xaa Ala
705                 710                 715                 720

Thr Xaa Glu Tyr Arg Ser Xaa Val Phe Gln Glu Pro Arg Phe Val Glu
        725                 730                 735

Tyr Phe Arg Xaa Ala Thr Pro Glu Xaa Glu Tyr Gly Arg Met Asn Ile
            740                 745                 750

Gly Ser Arg Pro Ser Lys Arg Lys Pro Ser Gly Gly Ile Glu Ser Leu
        755                 760                 765

Arg Ala Ile Pro Trp Ile Phe Ala Trp Thr Gln Thr Arg Phe His Leu
770                 775                 780

Pro Val Trp Leu Gly Phe Gly Xaa Ala Xaa Xaa His Xaa Xaa Xaa Lys
785                 790                 795                 800

Asp Xaa Xaa Asn Xaa Xaa Leu Xaa Xaa Met Tyr Xaa Xaa Trp Pro
                805                 810                 815

Phe Phe Arg Val Xaa Xaa Asp Leu Xaa Glu Met Val Phe Ala Lys Gly
            820                 825                 830

Xaa Pro Gly Ile Ala Ala Xaa Tyr Asp Xaa Leu Leu Val Xaa Xaa Xaa
```

-continued

```
                835                 840                 845
Leu Xaa Xaa Xaa Gly Glu Xaa Leu Arg Xaa Xaa Xaa Glu Glu Thr Xaa
        850                 855                 860

Xaa Leu Xaa Leu Gln Xaa Ala Gly His Lys Asp Xaa Leu Glu Gly Asp
865                 870                 875                 880

Xaa Tyr Leu Lys Gln Arg Leu Arg Leu Arg Xaa Xaa Tyr Ile Thr Thr
                885                 890                 895

Xaa Asn Val Xaa Gln Ala Tyr Thr Xaa Lys Arg Ile Arg Asp Pro Xaa
            900                 905                 910

Xaa Xaa Val Xaa Xaa Xaa Pro Xaa Xaa Ser Lys Xaa Xaa Xaa Xaa Xaa
        915                 920                 925

Xaa Xaa Pro Ala Xaa Glu Leu Xaa Xaa Leu Asn Xaa Xaa Ser Xaa Tyr
        930                 935                 940

Ala Pro Gly Leu Glu Asp Thr Leu Ile Leu Thr Met Lys Gly Ile Ala
945                 950                 955                 960

Ala Gly Xaa Gln Asn Thr Gly
            965
```

```
<210> SEQ ID NO 9
<211> LENGTH: 967
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4
<223> OTHER INFORMATION: Xaa = Any Amino Acid and can be present or
      absent
<220> FEATURE:
<221> NAME/KEY: VARIANT
<222> LOCATION: 8
<223> OTHER INFORMATION: Xaa = K or R
<220> FEATURE:
<221> NAME/KEY: VARIANT
<222> LOCATION: 14
<223> OTHER INFORMATION: Xaa = A or V
<220> FEATURE:
<221> NAME/KEY: VARIANT
<222> LOCATION: 15
<223> OTHER INFORMATION: Xaa = Q or H
<220> FEATURE:
<221> NAME/KEY: VARIANT
<222> LOCATION: 20
<223> OTHER INFORMATION: Xaa = V or A
<220> FEATURE:
<221> NAME/KEY: VARIANT
<222> LOCATION: 24
<223> OTHER INFORMATION: Xaa = V or L
<220> FEATURE:
<221> NAME/KEY: VARIANT
<222> LOCATION: 26
<223> OTHER INFORMATION: Xaa = E or D
<220> FEATURE:
<221> NAME/KEY: VARIANT
<222> LOCATION: 31
<223> OTHER INFORMATION: Xaa = V or I
<220> FEATURE:
<221> NAME/KEY: VARIANT
<222> LOCATION: 38
<223> OTHER INFORMATION: Xaa = L or V
<220> FEATURE:
<221> NAME/KEY: VARIANT
<222> LOCATION: 44
<223> OTHER INFORMATION: Xaa = I or V
<220> FEATURE:
<221> NAME/KEY: VARIANT
<222> LOCATION: 47
<223> OTHER INFORMATION: Xaa = D or G
<220> FEATURE:
```

```
<221> NAME/KEY: VARIANT
<222> LOCATION: 52
<223> OTHER INFORMATION: Xaa = D or H
<220> FEATURE:
<221> NAME/KEY: VARIANT
<222> LOCATION: 53
<223> OTHER INFORMATION: Xaa = L or I
<220> FEATURE:
<221> NAME/KEY: VARIANT
<222> LOCATION: 59
<223> OTHER INFORMATION: Xaa = E or D
<220> FEATURE:
<221> NAME/KEY: VARIANT
<222> LOCATION: 60
<223> OTHER INFORMATION: Xaa = C or L
<220> FEATURE:
<221> NAME/KEY: VARIANT
<222> LOCATION: 64
<223> OTHER INFORMATION: Xaa = A or S
<220> FEATURE:
<221> NAME/KEY: VARIANT
<222> LOCATION: 75
<223> OTHER INFORMATION: Xaa = K or R
<220> FEATURE:
<221> NAME/KEY: VARIANT
<222> LOCATION: 83
<223> OTHER INFORMATION: Xaa = L or I
<220> FEATURE:
<221> NAME/KEY: VARIANT
<222> LOCATION: 85
<223> OTHER INFORMATION: Xaa = S or G
<220> FEATURE:
<221> NAME/KEY: VARIANT
<222> LOCATION: 87
<223> OTHER INFORMATION: Xaa = D or P
<220> FEATURE:
<221> NAME/KEY: VARIANT
<222> LOCATION: 88
<223> OTHER INFORMATION: Xaa = P or A
<220> FEATURE:
<221> NAME/KEY: VARIANT
<222> LOCATION: 95
<223> OTHER INFORMATION: Xaa = A or S
<220> FEATURE:
<221> NAME/KEY: VARIANT
<222> LOCATION: 96
<223> OTHER INFORMATION: Xaa = K or S
<220> FEATURE:
<221> NAME/KEY: VARIANT
<222> LOCATION: 97
<223> OTHER INFORMATION: Xaa = A or S
<220> FEATURE:
<221> NAME/KEY: VARIANT
<222> LOCATION: 99
<223> OTHER INFORMATION: Xaa = S or A
<220> FEATURE:
<221> NAME/KEY: VARIANT
<222> LOCATION: 115
<223> OTHER INFORMATION: Xaa = Y or H
<220> FEATURE:
<221> NAME/KEY: VARIANT
<222> LOCATION: 124
<223> OTHER INFORMATION: Xaa = K or R
<220> FEATURE:
<221> NAME/KEY: VARIANT
<222> LOCATION: 128
<223> OTHER INFORMATION: Xaa = A or V
<220> FEATURE:
<221> NAME/KEY: VARIANT
<222> LOCATION: 139
<223> OTHER INFORMATION: Xaa = I or L
<220> FEATURE:
<221> NAME/KEY: VARIANT
<222> LOCATION: 143
<223> OTHER INFORMATION: Xaa = F or L
<220> FEATURE:
<221> NAME/KEY: VARIANT
<222> LOCATION: 145
<223> OTHER INFORMATION: Xaa = R or K
```

-continued

```
<220> FEATURE:
<221> NAME/KEY: VARIANT
<222> LOCATION: 149
<223> OTHER INFORMATION: Xaa = D or Q
<220> FEATURE:
<221> NAME/KEY: VARIANT
<222> LOCATION: 150
<223> OTHER INFORMATION: Xaa = L or M
<220> FEATURE:
<221> NAME/KEY: VARIANT
<222> LOCATION: 153
<223> OTHER INFORMATION: Xaa = S or T
<220> FEATURE:
<221> NAME/KEY: VARIANT
<222> LOCATION: 154
<223> OTHER INFORMATION: Xaa = P or R
<220> FEATURE:
<221> NAME/KEY: VARIANT
<222> LOCATION: 157
<223> OTHER INFORMATION: Xaa = V or I
<220> FEATURE:
<221> NAME/KEY: VARIANT
<222> LOCATION: 163
<223> OTHER INFORMATION: Xaa = N or S
<220> FEATURE:
<221> NAME/KEY: VARIANT
<222> LOCATION: 170
<223> OTHER INFORMATION: Xaa = L or F
<220> FEATURE:
<221> NAME/KEY: VARIANT
<222> LOCATION: 187
<223> OTHER INFORMATION: Xaa = S or G
<220> FEATURE:
<221> NAME/KEY: VARIANT
<222> LOCATION: 197
<223> OTHER INFORMATION: Xaa = Y or C
<220> FEATURE:
<221> NAME/KEY: VARIANT
<222> LOCATION: 198
<223> OTHER INFORMATION: Xaa = S or A
<220> FEATURE:
<221> NAME/KEY: VARIANT
<222> LOCATION: 203
<223> OTHER INFORMATION: Xaa = P or A
<220> FEATURE:
<221> NAME/KEY: VARIANT
<222> LOCATION: 227
<223> OTHER INFORMATION: Xaa = R or K
<220> FEATURE:
<221> NAME/KEY: VARIANT
<222> LOCATION: 229
<223> OTHER INFORMATION: Xaa = T or L
<220> FEATURE:
<221> NAME/KEY: VARIANT
<222> LOCATION: 236
<223> OTHER INFORMATION: Xaa = E or H
<220> FEATURE:
<221> NAME/KEY: VARIANT
<222> LOCATION: 243
<223> OTHER INFORMATION: Xaa = Y or D
<220> FEATURE:
<221> NAME/KEY: VARIANT
<222> LOCATION: 252
<223> OTHER INFORMATION: Xaa = V or I
<220> FEATURE:
<221> NAME/KEY: VARIANT
<222> LOCATION: 259
<223> OTHER INFORMATION: Xaa = V or I
<220> FEATURE:
<221> NAME/KEY: VARIANT
<222> LOCATION: 269
<223> OTHER INFORMATION: Xaa = N or D
<220> FEATURE:
<221> NAME/KEY: VARIANT
<222> LOCATION: 278
<223> OTHER INFORMATION: Xaa = L or V
<220> FEATURE:
<221> NAME/KEY: VARIANT
<222> LOCATION: 312
```

```
<223> OTHER INFORMATION: Xaa = A or S
<220> FEATURE:
<221> NAME/KEY: VARIANT
<222> LOCATION: 313
<223> OTHER INFORMATION: Xaa = N or T
<220> FEATURE:
<221> NAME/KEY: VARIANT
<222> LOCATION: 314
<223> OTHER INFORMATION: Xaa = L or M
<220> FEATURE:
<221> NAME/KEY: VARIANT
<222> LOCATION: 316
<223> OTHER INFORMATION: Xaa = C or F
<220> FEATURE:
<221> NAME/KEY: VARIANT
<222> LOCATION: 321
<223> OTHER INFORMATION: Xaa = D or N
<220> FEATURE:
<221> NAME/KEY: VARIANT
<222> LOCATION: 326
<223> OTHER INFORMATION: Xaa = L or M
<220> FEATURE:
<221> NAME/KEY: VARIANT
<222> LOCATION: 332
<223> OTHER INFORMATION: Xaa = N or S
<220> FEATURE:
<221> NAME/KEY: VARIANT
<222> LOCATION: 338
<223> OTHER INFORMATION: Xaa = R or Q
<220> FEATURE:
<221> NAME/KEY: VARIANT
<222> LOCATION: 339
<223> OTHER INFORMATION: Xaa = A or S
<220> FEATURE:
<221> NAME/KEY: VARIANT
<222> LOCATION: 342
<223> OTHER INFORMATION: Xaa = L or V
<220> FEATURE:
<221> NAME/KEY: VARIANT
<222> LOCATION: 343
<223> OTHER INFORMATION: Xaa = H or L
<220> FEATURE:
<221> NAME/KEY: VARIANT
<222> LOCATION: 345
<223> OTHER INFORMATION: Xaa = S or N
<220> FEATURE:
<221> NAME/KEY: VARIANT
<222> LOCATION: 347
<223> OTHER INFORMATION: Xaa = K or R
<220> FEATURE:
<221> NAME/KEY: VARIANT
<222> LOCATION: 348
<223> OTHER INFORMATION: Xaa = K or R
<220> FEATURE:
<221> NAME/KEY: VARIANT
<222> LOCATION: 349
<223> OTHER INFORMATION: Xaa = D or A
<220> FEATURE:
<221> NAME/KEY: VARIANT
<222> LOCATION: 361
<223> OTHER INFORMATION: Xaa = V or I
<220> FEATURE:
<221> NAME/KEY: VARIANT
<222> LOCATION: 363
<223> OTHER INFORMATION: Xaa = P or T
<220> FEATURE:
<221> NAME/KEY: VARIANT
<222> LOCATION: 370
<223> OTHER INFORMATION: Xaa = I or V
<220> FEATURE:
<221> NAME/KEY: VARIANT
<222> LOCATION: 374
<223> OTHER INFORMATION: Xaa = V or L
<220> FEATURE:
<221> NAME/KEY: VARIANT
<222> LOCATION: 377
<223> OTHER INFORMATION: Xaa = K or N
<220> FEATURE:
<221> NAME/KEY: VARIANT
```

```
<222> LOCATION: 385
<223> OTHER INFORMATION: Xaa = A or S
<220> FEATURE:
<221> NAME/KEY: VARIANT
<222> LOCATION: 386
<223> OTHER INFORMATION: Xaa = R or H
<220> FEATURE:
<221> NAME/KEY: VARIANT
<222> LOCATION: 391
<223> OTHER INFORMATION: Xaa = S or N
<220> FEATURE:
<221> NAME/KEY: VARIANT
<222> LOCATION: 395
<223> OTHER INFORMATION: Xaa = D or E
<220> FEATURE:
<221> NAME/KEY: VARIANT
<222> LOCATION: 396
<223> OTHER INFORMATION: Xaa = I or V
<220> FEATURE:
<221> NAME/KEY: VARIANT
<222> LOCATION: 397
<223> OTHER INFORMATION: Xaa = P or L
<220> FEATURE:
<221> NAME/KEY: VARIANT
<222> LOCATION: 398
<223> OTHER INFORMATION: Xaa = E or V
<220> FEATURE:
<221> NAME/KEY: VARIANT
<222> LOCATION: 403
<223> OTHER INFORMATION: Xaa = T or I
<220> FEATURE:
<221> NAME/KEY: VARIANT
<222> LOCATION: 404
<223> OTHER INFORMATION: Xaa = N or S
<220> FEATURE:
<221> NAME/KEY: VARIANT
<222> LOCATION: 405
<223> OTHER INFORMATION: Xaa = V or L
<220> FEATURE:
<221> NAME/KEY: VARIANT
<222> LOCATION: 408
<223> OTHER INFORMATION: Xaa = F or L
<220> FEATURE:
<221> NAME/KEY: VARIANT
<222> LOCATION: 426
<223> OTHER INFORMATION: Xaa = P or V
<220> FEATURE:
<221> NAME/KEY: VARIANT
<222> LOCATION: 431
<223> OTHER INFORMATION: Xaa = S or T
<220> FEATURE:
<221> NAME/KEY: VARIANT
<222> LOCATION: 448
<223> OTHER INFORMATION: Xaa = R or K
<220> FEATURE:
<221> NAME/KEY: VARIANT
<222> LOCATION: 461
<223> OTHER INFORMATION: Xaa = V or A
<220> FEATURE:
<221> NAME/KEY: VARIANT
<222> LOCATION: 462
<223> OTHER INFORMATION: Xaa = L or M
<220> FEATURE:
<221> NAME/KEY: VARIANT
<222> LOCATION: 464
<223> OTHER INFORMATION: Xaa = S or A
<220> FEATURE:
<221> NAME/KEY: VARIANT
<222> LOCATION: 468
<223> OTHER INFORMATION: Xaa = Y or H
<220> FEATURE:
<221> NAME/KEY: VARIANT
<222> LOCATION: 475
<223> OTHER INFORMATION: Xaa = R or A
<220> FEATURE:
<221> NAME/KEY: VARIANT
<222> LOCATION: 484
<223> OTHER INFORMATION: Xaa = D or E
<220> FEATURE:
```

```
<221> NAME/KEY: VARIANT
<222> LOCATION: 505
<223> OTHER INFORMATION: Xaa = E or D
<220> FEATURE:
<221> NAME/KEY: VARIANT
<222> LOCATION: 511
<223> OTHER INFORMATION: Xaa = L or M
<220> FEATURE:
<221> NAME/KEY: VARIANT
<222> LOCATION: 513
<223> OTHER INFORMATION: Xaa = T or A
<220> FEATURE:
<221> NAME/KEY: VARIANT
<222> LOCATION: 517
<223> OTHER INFORMATION: Xaa = I or L
<220> FEATURE:
<221> NAME/KEY: VARIANT
<222> LOCATION: 529
<223> OTHER INFORMATION: Xaa = I or V
<220> FEATURE:
<221> NAME/KEY: VARIANT
<222> LOCATION: 535
<223> OTHER INFORMATION: Xaa = A or S
<220> FEATURE:
<221> NAME/KEY: VARIANT
<222> LOCATION: 541
<223> OTHER INFORMATION: Xaa = A or S
<220> FEATURE:
<221> NAME/KEY: VARIANT
<222> LOCATION: 550
<223> OTHER INFORMATION: Xaa = H or R
<220> FEATURE:
<221> NAME/KEY: VARIANT
<222> LOCATION: 551
<223> OTHER INFORMATION: Xaa = V or I
<220> FEATURE:
<221> NAME/KEY: VARIANT
<222> LOCATION: 569
<223> OTHER INFORMATION: Xaa = A or G
<220> FEATURE:
<221> NAME/KEY: VARIANT
<222> LOCATION: 574
<223> OTHER INFORMATION: Xaa = L or V
<220> FEATURE:
<221> NAME/KEY: VARIANT
<222> LOCATION: 580
<223> OTHER INFORMATION: Xaa = I or V
<220> FEATURE:
<221> NAME/KEY: VARIANT
<222> LOCATION: 607
<223> OTHER INFORMATION: Xaa = L or F
<220> FEATURE:
<221> NAME/KEY: VARIANT
<222> LOCATION: 612
<223> OTHER INFORMATION: Xaa = Q or A
<220> FEATURE:
<221> NAME/KEY: VARIANT
<222> LOCATION: 613
<223> OTHER INFORMATION: Xaa = L or M
<220> FEATURE:
<221> NAME/KEY: VARIANT
<222> LOCATION: 616
<223> OTHER INFORMATION: Xaa = S or A
<220> FEATURE:
<221> NAME/KEY: VARIANT
<222> LOCATION: 619
<223> OTHER INFORMATION: Xaa = E or D
<220> FEATURE:
<221> NAME/KEY: VARIANT
<222> LOCATION: 621
<223> OTHER INFORMATION: Xaa = I or V
<220> FEATURE:
<221> NAME/KEY: VARIANT
<222> LOCATION: 622
<223> OTHER INFORMATION: Xaa = K or N
<220> FEATURE:
<221> NAME/KEY: VARIANT
<222> LOCATION: 627
<223> OTHER INFORMATION: Xaa = F or Y
```

```
<220> FEATURE:
<221> NAME/KEY: VARIANT
<222> LOCATION: 661
<223> OTHER INFORMATION: Xaa = H or N
<220> FEATURE:
<221> NAME/KEY: VARIANT
<222> LOCATION: 675
<223> OTHER INFORMATION: Xaa = Q or H
<220> FEATURE:
<221> NAME/KEY: VARIANT
<222> LOCATION: 681
<223> OTHER INFORMATION: Xaa = H or L
<220> FEATURE:
<221> NAME/KEY: VARIANT
<222> LOCATION: 690
<223> OTHER INFORMATION: Xaa = F or Y
<220> FEATURE:
<221> NAME/KEY: VARIANT
<222> LOCATION: 703
<223> OTHER INFORMATION: Xaa = I or V
<220> FEATURE:
<221> NAME/KEY: VARIANT
<222> LOCATION: 704
<223> OTHER INFORMATION: Xaa = S or A
<220> FEATURE:
<221> NAME/KEY: VARIANT
<222> LOCATION: 713
<223> OTHER INFORMATION: Xaa = L or M
<220> FEATURE:
<221> NAME/KEY: VARIANT
<222> LOCATION: 719
<223> OTHER INFORMATION: Xaa = V or I
<220> FEATURE:
<221> NAME/KEY: VARIANT
<222> LOCATION: 722
<223> OTHER INFORMATION: Xaa = E or K
<220> FEATURE:
<221> NAME/KEY: VARIANT
<222> LOCATION: 727
<223> OTHER INFORMATION: Xaa = I or V
<220> FEATURE:
<221> NAME/KEY: VARIANT
<222> LOCATION: 794
<223> OTHER INFORMATION: Xaa = F or I
<220> FEATURE:
<221> NAME/KEY: VARIANT
<222> LOCATION: 797
<223> OTHER INFORMATION: Xaa = I or V
<220> FEATURE:
<221> NAME/KEY: VARIANT
<222> LOCATION: 803
<223> OTHER INFORMATION: Xaa = R or K
<220> FEATURE:
<221> NAME/KEY: VARIANT
<222> LOCATION: 806
<223> OTHER INFORMATION: Xaa = H or Q
<220> FEATURE:
<221> NAME/KEY: VARIANT
<222> LOCATION: 807
<223> OTHER INFORMATION: Xaa = I or M
<220> FEATURE:
<221> NAME/KEY: VARIANT
<222> LOCATION: 809
<223> OTHER INFORMATION: Xaa = Q or R
<220> FEATURE:
<221> NAME/KEY: VARIANT
<222> LOCATION: 810
<223> OTHER INFORMATION: Xaa = E or D
<220> FEATURE:
<221> NAME/KEY: VARIANT
<222> LOCATION: 813
<223> OTHER INFORMATION: Xaa = N or Q
<220> FEATURE:
<221> NAME/KEY: VARIANT
<222> LOCATION: 821
<223> OTHER INFORMATION: Xaa = T or S
<220> FEATURE:
<221> NAME/KEY: VARIANT
<222> LOCATION: 822
```

```
<223> OTHER INFORMATION: Xaa = I or L
<220> FEATURE:
<221> NAME/KEY: VARIANT
<222> LOCATION: 833
<223> OTHER INFORMATION: Xaa = D or N
<220> FEATURE:
<221> NAME/KEY: VARIANT
<222> LOCATION: 839
<223> OTHER INFORMATION: Xaa = L or V
<220> FEATURE:
<221> NAME/KEY: VARIANT
<222> LOCATION: 842
<223> OTHER INFORMATION: Xaa = K or R
<220> FEATURE:
<221> NAME/KEY: VARIANT
<222> LOCATION: 846
<223> OTHER INFORMATION: Xaa = S or A
<220> FEATURE:
<221> NAME/KEY: VARIANT
<222> LOCATION: 850
<223> OTHER INFORMATION: Xaa = W or Q
<220> FEATURE:
<221> NAME/KEY: VARIANT
<222> LOCATION: 851
<223> OTHER INFORMATION: Xaa = P or S
<220> FEATURE:
<221> NAME/KEY: VARIANT
<222> LOCATION: 852
<223> OTHER INFORMATION: Xaa = L or F
<220> FEATURE:
<221> NAME/KEY: VARIANT
<222> LOCATION: 859
<223> OTHER INFORMATION: Xaa = N or M
<220> FEATURE:
<221> NAME/KEY: VARIANT
<222> LOCATION: 864
<223> OTHER INFORMATION: Xaa = K or Q
<220> FEATURE:
<221> NAME/KEY: VARIANT
<222> LOCATION: 867
<223> OTHER INFORMATION: Xaa = L or I
<220> FEATURE:
<221> NAME/KEY: VARIANT
<222> LOCATION: 870
<223> OTHER INFORMATION: Xaa = V or T
<220> FEATURE:
<221> NAME/KEY: VARIANT
<222> LOCATION: 876
<223> OTHER INFORMATION: Xaa = L or D
<220> FEATURE:
<221> NAME/KEY: VARIANT
<222> LOCATION: 881
<223> OTHER INFORMATION: Xaa = P or L
<220> FEATURE:
<221> NAME/KEY: VARIANT
<222> LOCATION: 891
<223> OTHER INFORMATION: Xaa = D or E
<220> FEATURE:
<221> NAME/KEY: VARIANT
<222> LOCATION: 892
<223> OTHER INFORMATION: Xaa = A or S
<220> FEATURE:
<221> NAME/KEY: VARIANT
<222> LOCATION: 897
<223> OTHER INFORMATION: Xaa = L or M
<220> FEATURE:
<221> NAME/KEY: VARIANT
<222> LOCATION: 900
<223> OTHER INFORMATION: Xaa = C or L
<220> FEATURE:
<221> NAME/KEY: VARIANT
<222> LOCATION: 905
<223> OTHER INFORMATION: Xaa = L or M
<220> FEATURE:
<221> NAME/KEY: VARIANT
<222> LOCATION: 912
<223> OTHER INFORMATION: Xaa = D or S
<220> FEATURE:
<221> NAME/KEY: VARIANT
```

```
<222> LOCATION: 913
<223> OTHER INFORMATION: Xaa = Y or F
<220> FEATURE:
<221> NAME/KEY: VARIANT
<222> LOCATION: 914
<223> OTHER INFORMATION: Xaa = H or Q
<220> FEATURE:
<221> NAME/KEY: VARIANT
<222> LOCATION: 917
<223> OTHER INFORMATION: Xaa = L or P
<220> FEATURE:
<221> NAME/KEY: VARIANT
<222> LOCATION: 918
<223> OTHER INFORMATION: Xaa = R or Q
<220> FEATURE:
<221> NAME/KEY: VARIANT
<222> LOCATION: 920
<223> OTHER INFORMATION: Xaa = H or P
<220> FEATURE:
<221> NAME/KEY: VARIANT
<222> LOCATION: 924
<223> OTHER INFORMATION: Xaa = E or D
<220> FEATURE:
<221> NAME/KEY: VARIANT
<222> LOCATION: 927
<223> OTHER INFORMATION: Xaa = D or E
<220> FEATURE:
<221> NAME/KEY: VARIANT
<222> LOCATION: 929
<223> OTHER INFORMATION: Xaa = S or N
<220> FEATURE:
<221> NAME/KEY: VARIANT
<222> LOCATION: 930
<223> OTHER INFORMATION: Xaa = K or Q
<220> FEATURE:
<221> NAME/KEY: VARIANT
<222> LOCATION: 936
<223> OTHER INFORMATION: Xaa = V or I
<220> FEATURE:
<221> NAME/KEY: VARIANT
<222> LOCATION: 940
<223> OTHER INFORMATION: Xaa = P or Q
<220> FEATURE:
<221> NAME/KEY: VARIANT
<222> LOCATION: 943
<223> OTHER INFORMATION: Xaa = E or D
<220> FEATURE:
<221> NAME/KEY: VARIANT
<222> LOCATION: 963
<223> OTHER INFORMATION: Xaa = M or L
<220> FEATURE:
<221> NAME/KEY: VARIANT
<222> LOCATION: 5, 6, 9, 10, 18, 22, 51, 56, 63, 69, 70, 71, 72, 73,
      74, 77, 81, 82, 94, 122, 131, 134, 148, 151, 155, 191, 194,
      230, 272, 317, 337, 344, 350, 360, 364, 380, 387, 390, 393,
      400, 402, 421, 425, 445, 467, 470, 481, 491, 499, 503, 507,
      512, 515, 522, 524, 553, 584, 585, 626, 700, 740, 745, 792,
      795, 798, 799, 802, 805, 814, 825, 847, 848, 855, 858, 860,
      865, 916, 921, 925, 926, 928, 933, 937, 941
<223> OTHER INFORMATION: Xaa = Any Amino Acid

<400> SEQUENCE: 9

Xaa Xaa Xaa Xaa Xaa Xaa Glu Xaa Xaa Xaa Ser Ile Asp Xaa Xaa Leu
1               5                   10                  15

Arg Xaa Leu Xaa Pro Xaa Lys Xaa Ser Xaa Asp Asp Lys Leu Xaa Glu
            20                  25                  30

Tyr Asp Ala Leu Leu Xaa Asp Arg Phe Leu Asp Xaa Leu Gln Xaa Leu
        35                  40                  45

His Gly Xaa Xaa Xaa Arg Glu Xaa Val Gln Xaa Xaa Tyr Glu Xaa Xaa
            50                  55                  60

Ala Glu Tyr Glu Xaa Xaa Xaa Xaa Xaa Xaa Leu Xaa Glu Leu Gly
65                  70                  75                  80

Xaa Xaa Xaa Thr Xaa Leu Xaa Xaa Gly Asp Ser Ile Val Xaa Xaa Xaa
```

```
                        85                  90                  95
Xaa Phe Xaa His Met Leu Asn Leu Ala Asn Leu Ala Glu Glu Val Gln
                100                 105                 110

Ile Ala Xaa Arg Arg Ile Lys Leu Xaa Lys Xaa Gly Asp Phe Xaa
        115                 120                 125

Asp Glu Xaa Ser Ala Xaa Thr Glu Ser Asp Xaa Glu Thr Xaa Lys
        130                 135                 140

Xaa Leu Val Xaa Xaa Xaa Lys Xaa Xaa Xaa Glu Xaa Phe Asp Ala
145                 150                 155                 160

Leu Lys Xaa Gln Thr Val Asp Leu Val Xaa Thr Ala His Pro Thr Gln
                165                 170                 175

Ser Val Arg Arg Ser Leu Leu Gln Lys His Xaa Arg Ile Arg Xaa Cys
                180                 185                 190

Leu Xaa Gln Leu Xaa Xaa Lys Asp Ile Thr Xaa Asp Asp Lys Gln Glu
            195                 200                 205

Leu Asp Glu Ala Leu Gln Arg Glu Ile Gln Ala Ala Phe Arg Thr Asp
            210                 215                 220

Glu Ile Xaa Arg Xaa Xaa Pro Thr Pro Gln Asp Xaa Met Arg Ala Gly
225                 230                 235                 240

Met Ser Xaa Phe His Glu Thr Ile Trp Lys Gly Xaa Pro Lys Phe Leu
                245                 250                 255

Arg Arg Xaa Asp Thr Ala Leu Lys Asn Ile Gly Ile Xaa Glu Arg Xaa
            260                 265                 270

Pro Tyr Asn Ala Pro Xaa Ile Gln Phe Ser Ser Trp Met Gly Gly Asp
            275                 280                 285

Arg Asp Gly Asn Pro Arg Val Thr Pro Glu Val Thr Arg Asp Val Cys
            290                 295                 300

Leu Leu Ala Arg Met Met Ala Xaa Xaa Xaa Tyr Xaa Xaa Gln Ile Glu
305                 310                 315                 320

Xaa Leu Met Phe Glu Xaa Ser Met Trp Arg Cys Xaa Asp Glu Leu Arg
            325                 330                 335

Xaa Xaa Xaa Asp Glu Xaa Xaa Xaa Xaa Ser Xaa Xaa Xaa Xaa Ala Lys
                340                 345                 350

His Tyr Ile Glu Phe Trp Lys Xaa Xaa Pro Xaa Xaa Glu Pro Tyr Arg
            355                 360                 365

Val Xaa Leu Gly Asp Xaa Arg Asp Xaa Leu Tyr Xaa Thr Arg Glu Arg
        370                 375                 380

Xaa Xaa Xaa Leu Leu Xaa Xaa Gly Xaa Ser Xaa Xaa Xaa Xaa Glu Xaa
385                 390                 395                 400

Thr Xaa Xaa Xaa Xaa Glu Gln Xaa Leu Glu Pro Leu Glu Leu Cys Tyr
            405                 410                 415

Arg Ser Leu Cys Xaa Cys Gly Asp Xaa Xaa Ile Ala Asp Gly Xaa Leu
                420                 425                 430

Leu Asp Phe Leu Arg Gln Val Ser Thr Phe Gly Leu Xaa Leu Val Xaa
                435                 440                 445

Leu Asp Ile Arg Gln Glu Ser Asp Arg His Thr Asp Xaa Xaa Asp Xaa
            450                 455                 460

Ile Thr Xaa Xaa Leu Xaa Ile Gly Ser Tyr Xaa Glu Trp Ser Glu Glu
465                 470                 475                 480

Xaa Arg Gln Xaa Trp Leu Leu Ser Glu Leu Xaa Gly Lys Arg Pro Leu
                485                 490                 495

Phe Gly Xaa Asp Leu Pro Xaa Thr Xaa Glu Xaa Ala Asp Val Xaa Xaa
            500                 505                 510
```

```
Xaa Phe Xaa Val Xaa Ala Glu Leu Pro Xaa Asp Xaa Phe Gly Ala Tyr
        515                 520                 525

Xaa Ile Ser Met Ala Thr Xaa Pro Ser Asp Val Leu Xaa Val Glu Leu
    530                 535                 540

Leu Gln Arg Glu Cys Xaa Xaa Lys Xaa Pro Leu Arg Val Val Pro Leu
545                 550                 555                 560

Phe Glu Lys Leu Ala Asp Leu Glu Xaa Ala Pro Ala Ala Xaa Ala Arg
                565                 570                 575

Leu Phe Ser Xaa Asp Trp Tyr Xaa Xaa Arg Ile Asn Gly Lys Gln Glu
            580                 585                 590

Val Met Ile Gly Tyr Ser Asp Ser Gly Lys Asp Ala Gly Arg Xaa Ser
        595                 600                 605

Ala Ala Trp Xaa Xaa Tyr Lys Xaa Gln Glu Xaa Leu Xaa Xaa Val Ala
        610                 615                 620

Lys Xaa Xaa Gly Val Lys Leu Thr Met Phe His Gly Arg Gly Gly Thr
625                 630                 635                 640

Val Gly Arg Gly Gly Gly Pro Thr His Leu Ala Ile Leu Ser Gln Pro
                645                 650                 655

Pro Asp Thr Ile Xaa Gly Ser Leu Arg Val Thr Val Gln Gly Glu Val
                660                 665                 670

Ile Glu Xaa Ser Phe Gly Glu Glu Xaa Leu Cys Phe Arg Thr Leu Gln
        675                 680                 685

Arg Xaa Thr Ala Ala Thr Leu Glu His Gly Met Xaa Pro Pro Xaa Xaa
    690                 695                 700

Pro Lys Pro Glu Trp Arg Ala Leu Xaa Asp Glu Met Ala Val Xaa Ala
705                 710                 715                 720

Thr Xaa Glu Tyr Arg Ser Xaa Val Phe Gln Glu Pro Arg Phe Val Glu
        725                 730                 735

Tyr Phe Arg Xaa Ala Thr Pro Glu Xaa Glu Tyr Gly Arg Met Asn Ile
            740                 745                 750

Gly Ser Arg Pro Ser Lys Arg Lys Pro Ser Gly Gly Ile Glu Ser Leu
        755                 760                 765

Arg Ala Ile Pro Trp Ile Phe Ala Trp Thr Gln Thr Arg Phe His Leu
    770                 775                 780

Pro Val Trp Leu Gly Phe Gly Xaa Ala Xaa Xaa His Xaa Xaa Xaa Lys
785                 790                 795                 800

Asp Xaa Xaa Asn Xaa Xaa Xaa Leu Xaa Xaa Met Tyr Xaa Xaa Trp Pro
        805                 810                 815

Phe Phe Arg Val Xaa Xaa Asp Leu Xaa Glu Met Val Phe Ala Lys Gly
            820                 825                 830

Xaa Pro Gly Ile Ala Ala Xaa Tyr Asp Xaa Leu Leu Val Xaa Xaa Xaa
        835                 840                 845

Leu Xaa Xaa Xaa Gly Glu Xaa Leu Arg Xaa Xaa Xaa Glu Glu Thr Xaa
850                 855                 860

Xaa Leu Xaa Leu Gln Xaa Ala Gly His Lys Asp Xaa Leu Glu Gly Asp
865                 870                 875                 880

Xaa Tyr Leu Lys Gln Arg Leu Arg Leu Arg Xaa Xaa Tyr Ile Thr Thr
        885                 890                 895

Xaa Asn Val Xaa Gln Ala Tyr Thr Xaa Lys Arg Ile Arg Asp Pro Xaa
            900                 905                 910

Xaa Xaa Val Xaa Xaa Xaa Pro Xaa Xaa Ser Lys Xaa Xaa Xaa Xaa Xaa
        915                 920                 925
```

```
Xaa Xaa Pro Ala Xaa Glu Leu Xaa Xaa Leu Asn Xaa Xaa Ser Xaa Tyr
        930             935             940

Ala Pro Gly Leu Glu Asp Thr Leu Ile Leu Thr Met Lys Gly Ile Ala
945             950             955             960

Ala Gly Xaa Gln Asn Thr Gly
            965
```

<210> SEQ ID NO 10
<211> LENGTH: 967
<212> TYPE: PRT
<213> ORGANISM: Artificial Sequence
<220> FEATURE:
<223> OTHER INFORMATION: Synthetic Construct

<400> SEQUENCE: 10

```
Met Ala Asn Arg Lys Leu Glu Lys Met Ala Ser Ile Asp Val His Leu
1               5                   10                  15

Arg Gln Leu Val Pro Gly Lys Val Ser Glu Asp Asp Lys Leu Val Glu
                20                  25                  30

Tyr Asp Ala Leu Leu Leu Asp Arg Phe Leu Asp Ile Leu Gln Asp Leu
            35                  40                  45

His Gly Glu Asp Leu Arg Glu Thr Val Gln Glu Leu Tyr Glu His Ser
    50                  55                  60

Ala Glu Tyr Glu Gly Lys His Glu Pro Lys Lys Leu Glu Glu Leu Gly
65                  70                  75                  80

Ser Val Leu Thr Ser Leu Asp Pro Gly Asp Ser Ile Val Ile Ala Lys
                85                  90                  95

Ala Phe Ser His Met Leu Asn Leu Ala Asn Leu Ala Glu Glu Val Gln
            100                 105                 110

Ile Ala Tyr Arg Arg Arg Ile Lys Lys Leu Lys Lys Gly Asp Phe Val
        115                 120                 125

Asp Glu Ser Ser Ala Thr Thr Glu Ser Asp Leu Glu Glu Thr Phe Lys
130                 135                 140

Lys Leu Val Gly Asp Leu Asn Lys Ser Pro Glu Glu Ile Phe Asp Ala
145                 150                 155                 160

Leu Lys Asn Gln Thr Val Asp Leu Val Leu Thr Ala His Pro Thr Gln
                165                 170                 175

Ser Val Arg Arg Ser Leu Leu Gln Lys His Gly Arg Ile Arg Asp Cys
            180                 185                 190

Leu Ala Gln Leu Tyr Ala Lys Asp Ile Thr Pro Asp Asp Lys Gln Glu
        195                 200                 205

Leu Asp Glu Ala Leu Gln Arg Glu Ile Gln Ala Ala Phe Arg Thr Asp
    210                 215                 220

Glu Ile Lys Arg Thr Pro Pro Thr Pro Gln Asp Glu Met Arg Ala Gly
225                 230                 235                 240

Met Ser Tyr Phe His Glu Thr Ile Trp Lys Gly Val Pro Lys Phe Leu
                245                 250                 255

Arg Arg Val Asp Thr Ala Leu Lys Asn Ile Gly Ile Glu Glu Arg Val
            260                 265                 270

Pro Tyr Asn Ala Pro Leu Ile Gln Phe Ser Ser Trp Met Gly Gly Asp
        275                 280                 285

Arg Asp Gly Asn Pro Arg Val Thr Pro Glu Val Thr Arg Asp Val Cys
290                 295                 300

Leu Leu Ala Arg Met Met Ala Thr Met Tyr Phe Asn Gln Ile Glu
305                 310                 315                 320
```

```
Asp Leu Met Phe Glu Met Ser Met Trp Arg Cys Asn Asp Glu Leu Arg
            325                 330                 335

Ala Arg Ala Asp Glu Val His Ala Asn Ser Arg Lys Asp Ala Ala Lys
            340                 345                 350

His Tyr Ile Glu Phe Trp Lys Ser Ile Pro Thr Thr Glu Pro Tyr Arg
            355                 360                 365

Val Ile Leu Gly Asp Val Arg Asp Lys Leu Tyr His Thr Arg Glu Arg
            370                 375                 380

Ala His Gln Leu Leu Ser Asn Gly His Ser Asp Val Pro Val Glu Ala
385                 390                 395                 400

Thr Phe Ile Asn Leu Glu Gln Phe Leu Glu Pro Leu Glu Leu Cys Tyr
            405                 410                 415

Arg Ser Leu Cys Ser Cys Gly Asp Arg Pro Ile Ala Asp Gly Ser Leu
            420                 425                 430

Leu Asp Phe Leu Arg Gln Val Ser Thr Phe Gly Leu Ser Leu Val Arg
            435                 440                 445

Leu Asp Ile Arg Gln Glu Ser Asp Arg His Thr Asp Val Leu Asp Ala
            450                 455                 460

Ile Thr Thr His Leu Asp Ile Gly Ser Tyr Arg Glu Trp Ser Glu Glu
465                 470                 475                 480

Arg Arg Gln Glu Trp Leu Leu Ser Glu Leu Ser Gly Lys Arg Pro Leu
            485                 490                 495

Phe Gly Ser Asp Leu Pro Lys Thr Glu Glu Ile Ala Asp Val Leu Asp
            500                 505                 510

Thr Phe His Val Ile Ala Glu Leu Pro Ala Asp Ser Phe Gly Ala Tyr
            515                 520                 525

Ile Ile Ser Met Ala Thr Ala Pro Ser Asp Val Leu Ala Val Glu Leu
530                 535                 540

Leu Gln Arg Glu Cys Arg Val Lys Gln Pro Leu Arg Val Val Pro Leu
545                 550                 555                 560

Phe Glu Lys Leu Ala Asp Leu Glu Ala Ala Pro Ala Ala Val Ala Arg
            565                 570                 575

Leu Phe Ser Val Asp Trp Tyr Lys Asn Arg Ile Asn Gly Lys Gln Glu
            580                 585                 590

Val Met Ile Gly Tyr Ser Asp Ser Gly Lys Asp Ala Gly Arg Leu Ser
            595                 600                 605

Ala Ala Trp Gln Leu Tyr Lys Ala Gln Glu Glu Leu Val Lys Val Ala
            610                 615                 620

Lys Glu Tyr Gly Val Lys Leu Thr Met Phe His Gly Arg Gly Gly Thr
625                 630                 635                 640

Val Gly Arg Gly Gly Gly Pro Thr His Leu Val Ile Leu Ser Gln Pro
            645                 650                 655

Pro Asp Thr Ile Asn Gly Ser Leu Arg Val Thr Val Gln Gly Glu Val
            660                 665                 670

Ile Glu Gln Ser Phe Gly Glu Glu His Leu Cys Phe Arg Thr Leu Gln
            675                 680                 685

Arg Phe Thr Ala Ala Thr Leu Glu His Gly Met Arg Pro Pro Ile Ser
            690                 695                 700

Pro Lys Pro Glu Trp Arg Ala Leu Leu Asp Glu Met Ala Val Val Ala
705                 710                 715                 720

Thr Glu Glu Tyr Arg Ser Val Val Phe Gln Glu Pro Arg Phe Val Glu
            725                 730                 735

Tyr Phe Arg Leu Ala Thr Pro Glu Leu Glu Tyr Gly Arg Met Asn Ile
```

-continued

```
                740                 745                 750
Gly Ser Arg Pro Ser Lys Arg Lys Pro Ser Gly Gly Ile Glu Ser Leu
            755                 760                 765
Arg Ala Ile Pro Trp Ile Phe Ala Trp Thr Gln Thr Arg Phe His Leu
        770                 775                 780
Pro Val Trp Leu Gly Phe Gly Ser Ala Ile Arg His Val Ile Glu Lys
785                 790                 795                 800
Asp Val Arg Asn Leu His Met Leu Gln Asp Met Tyr Gln His Trp Pro
                805                 810                 815
Phe Phe Arg Val Thr Ile Asp Leu Ile Glu Met Val Phe Ala Lys Gly
            820                 825                 830
Asp Pro Gly Ile Ala Ala Leu Tyr Asp Lys Leu Leu Val Ser Glu Glu
        835                 840                 845
Leu Trp Pro Phe Gly Glu Lys Leu Arg Ala Asn Phe Glu Glu Thr Lys
850                 855                 860
Lys Leu Ile Leu Gln Thr Ala Gly His Lys Asp Leu Leu Glu Gly Asp
865                 870                 875                 880
Pro Tyr Leu Lys Gln Arg Leu Arg Leu Arg Asp Ser Tyr Ile Thr Thr
                885                 890                 895
Leu Asn Val Cys Gln Ala Tyr Thr Leu Lys Arg Ile Arg Asp Pro Ser
            900                 905                 910
Tyr His Val Thr Leu Arg Pro His Ile Ser Lys Glu Ile Ala Glu Ser
        915                 920                 925
Ser Lys Pro Ala Lys Glu Leu Ile Glu Leu Asn Pro Thr Ser Glu Tyr
    930                 935                 940
Ala Pro Gly Leu Glu Asp Thr Leu Ile Leu Thr Met Lys Gly Ile Ala
945                 950                 955                 960
Ala Gly Leu Gln Asn Thr Gly
                965

<210> SEQ ID NO 11
<211> LENGTH: 967
<212> TYPE: PRT
<213> ORGANISM: Artificial Sequence
<220> FEATURE:
<223> OTHER INFORMATION: Synthetic Construct

<400> SEQUENCE: 11

Met Ala Asn Arg Lys Leu Glu Lys Met Ala Ser Ile Asp Val His Leu
1               5                   10                  15
Arg Gln Leu Val Pro Gly Lys Val Ser Glu Asp Asp Lys Leu Val Glu
            20                  25                  30
Tyr Asp Ala Leu Leu Leu Asp Arg Phe Leu Asp Ile Leu Gln Asp Leu
        35                  40                  45
His Gly Glu Asp Leu Arg Glu Thr Val Gln Glu Leu Tyr Glu His Ser
    50                  55                  60
Ala Glu Tyr Glu Gly Lys His Glu Pro Lys Lys Leu Glu Glu Leu Gly
65                  70                  75                  80
Ser Val Leu Thr Ser Leu Asp Pro Gly Asp Ser Ile Val Ile Ala Lys
                85                  90                  95
Ala Phe Ser His Met Leu Asn Leu Ala Asn Leu Ala Glu Glu Val Gln
            100                 105                 110
Ile Ala Tyr Arg Arg Arg Ile Lys Lys Leu Lys Lys Gly Asp Phe Val
        115                 120                 125
Asp Glu Ser Ser Ala Thr Thr Glu Ser Asp Leu Glu Glu Thr Phe Lys
```

```
            130             135             140
Lys Leu Val Gly Asp Leu Asn Lys Ser Pro Glu Glu Ile Phe Asp Ala
145             150             155             160

Leu Lys Asn Gln Thr Val Asp Leu Val Leu Thr Ala His Pro Thr Gln
                165             170             175

Ser Val Arg Arg Ser Leu Leu Gln Lys His Gly Arg Ile Arg Asp Cys
            180             185             190

Leu Ala Gln Leu Tyr Ala Lys Asp Ile Thr Pro Asp Asp Lys Gln Glu
            195             200             205

Leu Asp Glu Ala Leu Gln Arg Glu Ile Gln Ala Ala Phe Arg Thr Asp
210             215             220

Glu Ile Lys Arg Thr Pro Pro Thr Pro Gln Asp Glu Met Arg Ala Gly
225             230             235             240

Met Ser Tyr Phe His Glu Thr Ile Trp Lys Gly Val Pro Lys Phe Leu
                245             250             255

Arg Arg Val Asp Thr Ala Leu Lys Asn Ile Gly Ile Glu Glu Arg Val
            260             265             270

Pro Tyr Asn Ala Pro Leu Ile Gln Phe Ser Ser Trp Met Gly Gly Asp
            275             280             285

Arg Asp Gly Asn Pro Arg Val Thr Pro Glu Val Thr Arg Asp Val Cys
290             295             300

Leu Leu Ala Arg Met Met Ala Ala Thr Met Tyr Phe Asn Gln Ile Glu
305             310             315             320

Asp Leu Met Phe Glu Met Ser Met Trp Arg Cys Asn Asp Glu Leu Arg
                325             330             335

Ala Arg Ala Asp Glu Val His Ala Asn Ser Arg Lys Asp Ala Ala Lys
            340             345             350

His Tyr Ile Glu Phe Trp Lys Ser Ile Pro Thr Thr Glu Pro Tyr Arg
            355             360             365

Val Ile Leu Gly Asp Val Arg Asp Lys Leu Tyr His Thr Arg Glu Arg
            370             375             380

Ala His Gln Leu Leu Ser Asn Gly His Ser Asp Val Pro Val Glu Ala
385             390             395             400

Thr Phe Ile Asn Leu Glu Gln Phe Leu Glu Pro Leu Glu Leu Cys Tyr
                405             410             415

Arg Ser Leu Cys Ser Cys Gly Asp Arg Pro Ile Ala Asp Gly Ser Leu
            420             425             430

Leu Asp Phe Leu Arg Gln Val Ser Thr Phe Gly Leu Ser Leu Val Arg
            435             440             445

Leu Asp Ile Arg Gln Glu Ser Asp Arg His Thr Asp Val Leu Asp Ala
450             455             460

Ile Thr Thr His Leu Asp Ile Gly Ser Tyr Arg Glu Trp Ser Glu Glu
465             470             475             480

Arg Arg Gln Glu Trp Leu Leu Ser Glu Leu Ser Gly Lys Arg Pro Leu
                485             490             495

Phe Gly Ser Asp Leu Pro Lys Thr Glu Glu Ile Ala Asp Val Leu Asp
            500             505             510

Thr Phe His Val Ile Ala Glu Leu Pro Ala Asp Ser Phe Gly Ala Tyr
            515             520             525

Ile Ile Ser Met Ala Thr Ala Pro Ser Asp Val Leu Ala Val Glu Leu
530             535             540

Leu Gln Arg Glu Cys Arg Val Lys Gln Pro Leu Arg Val Val Pro Leu
545             550             555             560
```

```
Phe Glu Lys Leu Ala Asp Leu Glu Ala Ala Pro Ala Ala Val Ala Arg
                565                 570                 575

Leu Phe Ser Val Asp Trp Tyr Lys Asn Arg Ile Asn Gly Lys Gln Glu
            580                 585                 590

Val Met Ile Gly Tyr Ser Asp Ser Gly Lys Asp Ala Gly Arg Leu Ser
        595                 600                 605

Ala Ala Trp Gln Leu Tyr Lys Ala Gln Glu Glu Leu Val Lys Val Ala
    610                 615                 620

Lys Glu Tyr Gly Val Lys Leu Thr Met Phe His Gly Arg Gly Gly Thr
625                 630                 635                 640

Val Gly Arg Gly Gly Gly Pro Thr His Leu Ala Ile Leu Ser Gln Pro
                645                 650                 655

Pro Asp Thr Ile Asn Gly Ser Leu Arg Val Thr Val Gln Gly Glu Val
            660                 665                 670

Ile Glu Gln Ser Phe Ser Glu Glu His Leu Cys Phe Arg Thr Leu Gln
        675                 680                 685

Arg Phe Thr Ala Ala Thr Leu Glu His Gly Met Arg Pro Pro Ile Ser
    690                 695                 700

Pro Lys Pro Glu Trp Arg Ala Leu Leu Asp Glu Met Ala Val Val Ala
705                 710                 715                 720

Thr Glu Glu Tyr Arg Ser Val Val Phe Gln Glu Pro Arg Phe Val Glu
                725                 730                 735

Tyr Phe Arg Leu Ala Thr Pro Glu Leu Glu Tyr Gly Arg Met Asn Ile
            740                 745                 750

Gly Ser Arg Pro Ser Lys Arg Lys Pro Ser Gly Gly Ile Glu Ser Leu
        755                 760                 765

Arg Ala Ile Pro Trp Ile Phe Ala Trp Thr Gln Thr Arg Phe His Leu
    770                 775                 780

Pro Val Trp Leu Gly Phe Gly Ser Ala Ile Arg His Val Ile Glu Lys
785                 790                 795                 800

Asp Val Arg Asn Leu His Met Leu Gln Asp Met Tyr Gln His Trp Pro
                805                 810                 815

Phe Phe Arg Val Thr Ile Asp Leu Ile Glu Met Val Phe Ala Lys Gly
            820                 825                 830

Asp Pro Gly Ile Ala Ala Leu Tyr Asp Lys Leu Leu Val Ser Glu Glu
        835                 840                 845

Leu Trp Pro Phe Gly Glu Lys Leu Arg Ala Asn Phe Glu Glu Thr Lys
    850                 855                 860

Lys Leu Ile Leu Gln Thr Ala Gly His Lys Asp Leu Leu Glu Gly Asp
865                 870                 875                 880

Pro Tyr Leu Lys Gln Arg Leu Arg Leu Arg Asp Ser Tyr Ile Thr Thr
                885                 890                 895

Leu Asn Val Cys Gln Ala Tyr Thr Leu Lys Arg Ile Arg Asp Pro Ser
            900                 905                 910

Tyr His Val Thr Leu Arg Pro His Ile Ser Lys Glu Ile Ala Glu Ser
        915                 920                 925

Ser Lys Pro Ala Lys Glu Leu Ile Glu Leu Asn Pro Thr Ser Glu Tyr
    930                 935                 940

Ala Pro Gly Leu Glu Asp Thr Leu Ile Leu Thr Met Lys Gly Ile Ala
945                 950                 955                 960

Ala Gly Leu Gln Asn Thr Gly
                965
```

```
<210> SEQ ID NO 12
<211> LENGTH: 967
<212> TYPE: PRT
<213> ORGANISM: Artificial Sequence
<220> FEATURE:
<223> OTHER INFORMATION: Synthetic Construct

<400> SEQUENCE: 12

Met Ala Asn Arg Lys Leu Glu Lys Met Ala Ser Ile Asp Val His Leu
1               5                   10                  15

Arg Gln Leu Val Pro Gly Lys Val Ser Glu Asp Lys Leu Val Glu
            20                  25                  30

Tyr Asp Ala Leu Leu Asp Arg Phe Leu Asp Ile Leu Gln Asp Leu
        35                  40                  45

His Gly Glu Asp Leu Arg Glu Thr Val Gln Glu Leu Tyr Glu His Ser
    50                  55                  60

Ala Glu Tyr Glu Gly Lys His Glu Pro Lys Lys Leu Glu Glu Leu Gly
65                  70                  75                  80

Ser Val Leu Thr Ser Leu Asp Pro Gly Asp Ser Ile Val Ile Ala Lys
                85                  90                  95

Ala Phe Ser His Met Leu Asn Leu Ala Asn Leu Ala Glu Glu Val Gln
            100                 105                 110

Ile Ala Tyr Arg Arg Ile Lys Lys Leu Lys Lys Gly Asp Phe Val
        115                 120                 125

Asp Glu Ser Ser Ala Thr Thr Glu Ser Asp Leu Glu Glu Thr Phe Lys
130                 135                 140

Lys Leu Val Gly Asp Leu Asn Lys Ser Pro Glu Glu Ile Phe Asp Ala
145                 150                 155                 160

Leu Lys Asn Gln Thr Val Asp Leu Val Leu Thr Ala His Pro Thr Gln
            165                 170                 175

Ser Val Arg Arg Ser Leu Leu Gln Lys His Gly Arg Ile Arg Asp Cys
        180                 185                 190

Leu Ala Gln Leu Tyr Ala Lys Asp Ile Thr Pro Asp Asp Lys Gln Glu
        195                 200                 205

Leu Asp Glu Ala Leu Gln Arg Glu Ile Gln Ala Ala Phe Arg Thr Asp
    210                 215                 220

Glu Ile Lys Arg Thr Pro Pro Thr Pro Gln Asp Glu Met Arg Ala Gly
225                 230                 235                 240

Met Ser Tyr Phe His Glu Thr Ile Trp Lys Gly Val Pro Lys Phe Leu
                245                 250                 255

Arg Arg Val Asp Thr Ala Leu Lys Asn Ile Gly Ile Glu Glu Arg Val
            260                 265                 270

Pro Tyr Asn Ala Pro Leu Ile Gln Phe Ser Ser Trp Met Gly Gly Asp
        275                 280                 285

Arg Asp Gly Asn Pro Arg Val Thr Pro Glu Val Thr Arg Asp Val Cys
    290                 295                 300

Leu Leu Ala Arg Met Met Ala Ala Thr Met Tyr Phe Asn Gln Ile Glu
305                 310                 315                 320

Asp Leu Met Phe Glu Met Ser Met Trp Arg Cys Asn Asp Glu Leu Arg
                325                 330                 335

Ala Arg Ala Asp Glu Val His Ala Asn Ser Arg Lys Asp Ala Ala Lys
            340                 345                 350

His Tyr Ile Glu Phe Trp Lys Ser Ile Pro Thr Thr Glu Pro Tyr Arg
        355                 360                 365
```

```
Val Ile Leu Gly Asp Val Arg Asp Lys Leu Tyr His Thr Arg Glu Arg
370                 375                 380

Ala His Gln Leu Leu Ser Asn Gly His Ser Asp Val Pro Val Glu Ala
385                 390                 395                 400

Thr Phe Ile Asn Leu Glu Gln Phe Leu Glu Pro Leu Glu Leu Cys Tyr
                405                 410                 415

Arg Ser Leu Cys Ser Cys Gly Asp Arg Pro Ile Ala Asp Gly Ser Leu
            420                 425                 430

Leu Asp Phe Leu Arg Gln Val Ser Thr Phe Gly Leu Ser Leu Val Arg
        435                 440                 445

Leu Asp Ile Arg Gln Glu Ser Asp Arg His Thr Asp Val Leu Asp Ala
450                 455                 460

Ile Thr Thr His Leu Asp Ile Gly Ser Tyr Arg Glu Trp Ser Glu Glu
465                 470                 475                 480

Arg Arg Gln Glu Trp Leu Leu Ser Glu Leu Ser Gly Lys Arg Pro Leu
                485                 490                 495

Phe Gly Ser Asp Leu Pro Lys Thr Glu Glu Ile Ala Asp Val Leu Asp
            500                 505                 510

Thr Phe His Val Ile Ala Glu Leu Pro Ala Asp Ser Phe Gly Ala Tyr
        515                 520                 525

Ile Ile Ser Met Ala Thr Ala Pro Ser Asp Val Leu Ala Val Glu Leu
530                 535                 540

Leu Gln Arg Glu Cys Arg Val Lys Gln Pro Leu Arg Val Val Pro Leu
545                 550                 555                 560

Phe Glu Lys Leu Ala Asp Leu Glu Ala Ala Pro Ala Val Ala Arg
                565                 570                 575

Leu Phe Ser Val Asp Trp Tyr Lys Asn Arg Ile Asn Gly Lys Gln Glu
            580                 585                 590

Val Met Ile Gly Tyr Ser Asp Ser Gly Lys Asp Ala Gly Arg Leu Ser
        595                 600                 605

Ala Ala Trp Gln Leu Tyr Lys Ala Gln Glu Leu Val Lys Val Ala
610                 615                 620

Lys Glu Tyr Gly Val Lys Leu Thr Met Phe His Gly Arg Gly Gly Thr
625                 630                 635                 640

Val Gly Arg Gly Gly Pro Thr His Leu Ala Ile Leu Ser Gln Pro
                645                 650                 655

Pro Asp Thr Ile Asn Gly Ser Leu Arg Val Thr Val Gln Gly Glu Val
            660                 665                 670

Ile Glu Gln Ser Phe Gly Glu Glu His Leu Cys Phe Arg Thr Leu Gln
        675                 680                 685

Arg Phe Thr Ala Ala Thr Leu Glu His Gly Met Arg Pro Pro Ile Ser
690                 695                 700

Pro Lys Pro Glu Trp Arg Ala Leu Leu Asp Glu Met Ala Val Val Ala
705                 710                 715                 720

Thr Glu Glu Tyr Arg Ser Val Val Phe Gln Pro Arg Phe Val Glu
                725                 730                 735

Tyr Phe Arg Leu Ala Thr Pro Glu Leu Glu Tyr Gly Arg Met Asn Ile
            740                 745                 750

Gly Ser Arg Pro Ser Lys Arg Lys Pro Ser Gly Gly Ile Glu Ser Leu
        755                 760                 765

Arg Ala Ile Pro Trp Ile Phe Ala Trp Ile Gln Thr Arg Phe His Leu
770                 775                 780

Pro Val Trp Leu Gly Phe Gly Ser Ala Ile Arg His Val Ile Glu Lys
```

```
                785                 790                 795                 800
Asp Val Arg Asn Leu His Met Leu Gln Asp Met Tyr Gln His Trp Pro
                    805                 810                 815

Phe Phe Arg Val Thr Ile Asp Leu Ile Glu Met Val Phe Ala Lys Gly
                820                 825                 830

Asp Pro Gly Ile Ala Ala Leu Tyr Asp Lys Leu Leu Val Ser Glu Glu
                835                 840                 845

Leu Trp Pro Phe Gly Glu Lys Leu Arg Ala Asn Phe Glu Glu Thr Lys
            850                 855                 860

Lys Leu Ile Leu Gln Thr Ala Gly His Lys Asp Leu Leu Glu Gly Asp
865                 870                 875                 880

Pro Tyr Leu Lys Gln Arg Leu Arg Leu Arg Asp Ser Tyr Ile Thr Thr
                    885                 890                 895

Leu Asn Val Cys Gln Ala Tyr Thr Leu Lys Arg Ile Arg Asp Pro Ser
                900                 905                 910

Tyr His Val Thr Leu Arg Pro His Ile Ser Lys Glu Ile Ala Glu Ser
                915                 920                 925

Ser Lys Pro Ala Lys Glu Leu Ile Glu Leu Asn Pro Thr Ser Glu Tyr
            930                 935                 940

Ala Pro Gly Leu Glu Asp Thr Leu Ile Leu Thr Met Lys Gly Ile Ala
945                 950                 955                 960

Ala Gly Leu Gln Asn Thr Gly
                965

<210> SEQ ID NO 13
<211> LENGTH: 967
<212> TYPE: PRT
<213> ORGANISM: Artificial Sequence
<220> FEATURE:
<223> OTHER INFORMATION: Synthetic Construct

<400> SEQUENCE: 13

Met Ala Asn Arg Lys Leu Glu Lys Met Ala Ser Ile Asp Val His Leu
1               5                   10                  15

Arg Gln Leu Val Pro Gly Lys Val Ser Glu Asp Asp Lys Leu Val Glu
                20                  25                  30

Tyr Asp Ala Leu Leu Leu Asp Arg Phe Leu Asp Ile Leu Gln Asp Leu
                35                  40                  45

His Gly Glu Asp Leu Arg Glu Thr Val Gln Glu Leu Tyr Glu His Ser
            50                  55                  60

Ala Glu Tyr Glu Gly Lys His Glu Pro Lys Lys Leu Glu Glu Leu Gly
65                  70                  75                  80

Ser Val Leu Thr Ser Leu Asp Pro Gly Asp Ser Ile Val Ile Ala Lys
                85                  90                  95

Ala Phe Ser His Met Leu Asn Leu Ala Asn Leu Ala Glu Glu Val Gln
                100                 105                 110

Ile Ala Tyr Arg Arg Ile Lys Lys Leu Lys Lys Gly Asp Phe Val
                115                 120                 125

Asp Glu Ser Ser Ala Thr Thr Glu Ser Asp Leu Glu Glu Thr Phe Lys
            130                 135                 140

Lys Leu Val Gly Asp Leu Asn Lys Ser Pro Glu Glu Ile Phe Asp Ala
145                 150                 155                 160

Leu Lys Asn Gln Thr Val Asp Leu Val Leu Thr Ala His Pro Thr Gln
                165                 170                 175

Ser Val Arg Arg Ser Leu Leu Gln Lys His Gly Arg Ile Arg Asp Cys
```

```
                180                 185                 190
Leu Ala Gln Leu Tyr Ala Lys Asp Ile Thr Pro Asp Asp Lys Gln Glu
                195                 200                 205
Leu Asp Glu Ala Leu Gln Arg Glu Ile Gln Ala Ala Phe Arg Thr Asp
                210                 215                 220
Glu Ile Lys Arg Thr Pro Thr Pro Gln Asp Glu Met Arg Ala Gly
225                 230                 235                 240
Met Ser Tyr Phe His Glu Thr Ile Trp Lys Gly Val Pro Lys Phe Leu
                245                 250                 255
Arg Arg Val Asp Thr Ala Leu Lys Asn Ile Gly Ile Glu Glu Arg Val
                260                 265                 270
Pro Tyr Asn Ala Pro Leu Ile Gln Phe Ser Ser Trp Met Gly Gly Asp
                275                 280                 285
Arg Asp Gly Asn Pro Arg Val Thr Pro Glu Val Thr Arg Asp Val Cys
                290                 295                 300
Leu Leu Ala Arg Met Met Ala Ala Thr Met Tyr Phe Asn Gln Ile Glu
305                 310                 315                 320
Asp Leu Met Phe Glu Met Ser Met Trp Arg Cys Asn Asp Glu Leu Arg
                325                 330                 335
Ala Arg Ala Asp Glu Val His Ala Asn Ser Arg Lys Asp Ala Ala Lys
                340                 345                 350
His Tyr Ile Glu Phe Trp Lys Ser Ile Pro Thr Thr Glu Pro Tyr Arg
                355                 360                 365
Val Ile Leu Gly Asp Val Arg Asp Lys Leu Tyr His Thr Arg Glu Arg
                370                 375                 380
Ala His Gln Leu Leu Ser Asn Gly His Ser Asp Val Pro Val Glu Ala
385                 390                 395                 400
Thr Phe Ile Asn Leu Glu Gln Phe Leu Glu Pro Leu Glu Leu Cys Tyr
                405                 410                 415
Arg Ser Leu Cys Ser Cys Gly Asp Arg Pro Ile Ala Asp Gly Ser Leu
                420                 425                 430
Leu Asp Phe Leu Arg Gln Val Ser Thr Phe Gly Leu Ser Leu Val Arg
                435                 440                 445
Leu Asp Ile Arg Gln Glu Ser Asp Arg His Thr Asp Val Leu Asp Ala
                450                 455                 460
Ile Thr Thr His Leu Asp Ile Gly Ser Tyr Arg Glu Trp Ser Glu Glu
465                 470                 475                 480
Arg Arg Gln Glu Trp Leu Leu Ser Glu Leu Ser Gly Lys Arg Pro Leu
                485                 490                 495
Phe Gly Ser Asp Leu Pro Lys Thr Glu Glu Ile Ala Asp Val Leu Asp
                500                 505                 510
Thr Phe His Val Ile Ala Glu Leu Pro Ala Asp Ser Phe Gly Ala Tyr
                515                 520                 525
Ile Ile Ser Met Ala Thr Ala Pro Ser Asp Val Leu Ala Val Glu Leu
                530                 535                 540
Leu Gln Arg Glu Cys Arg Val Lys Gln Pro Leu Arg Val Val Pro Leu
545                 550                 555                 560
Phe Glu Lys Leu Ala Asp Leu Glu Ala Ala Pro Ala Ala Val Ala Arg
                565                 570                 575
Leu Phe Ser Val Asp Trp Tyr Lys Asn Arg Ile Asn Gly Lys Gln Glu
                580                 585                 590
Val Met Ile Gly Tyr Ser Asp Ser Gly Lys Asp Ala Gly Arg Leu Ser
                595                 600                 605
```

Ala Ala Trp Gln Leu Tyr Lys Ala Gln Glu Leu Val Lys Val Ala
            610                 615                 620

Lys Glu Tyr Gly Val Lys Leu Thr Met Phe His Gly Arg Gly Gly Thr
625                 630                 635                 640

Val Gly Arg Gly Gly Pro Thr His Leu Val Ile Leu Ser Gln Pro
                645                 650                 655

Pro Asp Thr Ile Asn Gly Ser Leu Arg Val Thr Val Gln Gly Glu Val
            660                 665                 670

Ile Glu Gln Ser Phe Ser Glu His Leu Cys Phe Arg Thr Leu Gln
        675                 680                 685

Arg Phe Thr Ala Ala Thr Leu Glu His Gly Met Arg Pro Pro Ile Ser
690                 695                 700

Pro Lys Pro Glu Trp Arg Ala Leu Leu Asp Glu Met Ala Val Ala
705                 710                 715                 720

Thr Glu Glu Tyr Arg Ser Val Val Phe Gln Glu Pro Arg Phe Val Glu
                725                 730                 735

Tyr Phe Arg Leu Ala Thr Pro Glu Leu Glu Tyr Gly Arg Met Asn Ile
            740                 745                 750

Gly Ser Arg Pro Ser Lys Arg Lys Pro Ser Gly Ile Glu Ser Leu
        755                 760                 765

Arg Ala Ile Pro Trp Ile Phe Ala Trp Thr Gln Thr Arg Phe His Leu
770                 775                 780

Pro Val Trp Leu Gly Phe Gly Ser Ala Ile Arg His Val Ile Glu Lys
785                 790                 795                 800

Asp Val Arg Asn Leu His Met Leu Gln Asp Met Tyr Gln His Trp Pro
                805                 810                 815

Phe Phe Arg Val Thr Ile Asp Leu Ile Glu Met Val Phe Ala Lys Gly
            820                 825                 830

Asp Pro Gly Ile Ala Ala Leu Tyr Asp Lys Leu Leu Val Ser Glu Glu
        835                 840                 845

Leu Trp Pro Phe Gly Glu Lys Leu Arg Ala Asn Phe Glu Glu Thr Lys
850                 855                 860

Lys Leu Ile Leu Gln Thr Ala Gly His Lys Asp Leu Leu Glu Gly Asp
865                 870                 875                 880

Pro Tyr Leu Lys Gln Gly Leu Arg Leu Arg Asp Ser Tyr Ile Thr Thr
                885                 890                 895

Leu Asn Val Cys Gln Ala Tyr Thr Leu Lys Arg Ile Arg Asp Pro Ser
            900                 905                 910

Tyr His Val Thr Leu Arg Pro His Ile Ser Lys Glu Ile Ala Glu Ser
        915                 920                 925

Ser Lys Pro Ala Lys Glu Leu Ile Glu Leu Asn Pro Thr Ser Glu Tyr
930                 935                 940

Ala Pro Gly Leu Glu Asp Thr Leu Ile Leu Thr Met Lys Gly Ile Ala
945                 950                 955                 960

Ala Gly Leu Gln Asn Thr Gly
                965

<210> SEQ ID NO 14
<211> LENGTH: 967
<212> TYPE: PRT
<213> ORGANISM: Artificial Sequence
<220> FEATURE:
<223> OTHER INFORMATION: Synthetic Construct

<400> SEQUENCE: 14

```
Met Ala Asn Arg Lys Leu Glu Lys Met Ala Ser Ile Asp Val His Leu
1               5                   10                  15

Arg Gln Leu Val Pro Gly Lys Val Ser Glu Asp Lys Leu Val Glu
            20                  25                  30

Tyr Asp Ala Leu Leu Leu Asp Arg Phe Leu Asp Ile Leu Gln Asp Leu
            35                  40                  45

His Gly Glu Asp Leu Arg Glu Thr Val Gln Glu Leu Tyr Glu His Ser
    50                  55                  60

Ala Glu Tyr Glu Gly Lys His Glu Pro Lys Lys Leu Glu Glu Leu Gly
65                  70                  75                  80

Ser Val Leu Thr Ser Leu Asp Pro Gly Asp Ser Ile Val Ile Ala Lys
                85                  90                  95

Ala Phe Ser His Met Leu Asn Leu Ala Asn Leu Ala Glu Glu Val Gln
                100                 105                 110

Ile Ala Tyr Arg Arg Ile Lys Lys Leu Lys Lys Gly Asp Phe Val
            115                 120                 125

Asp Glu Ser Ser Ala Thr Thr Glu Ser Asp Leu Glu Glu Thr Phe Lys
    130                 135                 140

Lys Leu Val Gly Asp Leu Asn Lys Ser Pro Glu Glu Ile Phe Asp Ala
145                 150                 155                 160

Leu Lys Asn Gln Thr Val Asp Leu Val Leu Thr Ala His Pro Thr Gln
                165                 170                 175

Ser Val Arg Arg Ser Leu Leu Gln Lys His Gly Arg Ile Arg Asp Cys
            180                 185                 190

Leu Ala Gln Leu Tyr Ala Lys Asp Ile Thr Pro Asp Asp Lys Gln Glu
            195                 200                 205

Leu Asp Glu Ala Leu Gln Arg Glu Ile Gln Ala Ala Phe Arg Thr Asp
    210                 215                 220

Glu Ile Lys Arg Thr Pro Pro Thr Pro Gln Asp Glu Met Arg Ala Gly
225                 230                 235                 240

Met Ser Tyr Phe His Glu Thr Ile Trp Lys Gly Val Pro Lys Phe Leu
                245                 250                 255

Arg Arg Val Asp Thr Ala Leu Lys Asn Ile Gly Ile Glu Glu Arg Val
            260                 265                 270

Pro Tyr Asn Ala Pro Leu Ile Gln Phe Ser Ser Trp Met Gly Gly Asp
    275                 280                 285

Arg Asp Gly Asn Pro Arg Val Thr Pro Glu Val Thr Arg Asp Val Cys
    290                 295                 300

Leu Leu Ala Arg Met Met Ala Ala Thr Met Tyr Phe Asn Gln Ile Glu
305                 310                 315                 320

Asp Leu Met Phe Glu Met Ser Met Trp Arg Cys Asn Asp Glu Leu Arg
                325                 330                 335

Ala Arg Ala Asp Glu Val His Ala Asn Ser Arg Lys Asp Ala Ala Lys
            340                 345                 350

His Tyr Ile Glu Phe Trp Lys Ser Ile Pro Thr Thr Glu Pro Tyr Arg
            355                 360                 365

Val Ile Leu Gly Asp Val Arg Asp Lys Leu Tyr His Thr Arg Glu Arg
    370                 375                 380

Ala His Gln Leu Leu Ser Asn Gly His Ser Asp Val Pro Val Glu Ala
385                 390                 395                 400

Thr Phe Ile Asn Leu Glu Gln Phe Leu Glu Pro Leu Glu Leu Cys Tyr
                405                 410                 415
```

-continued

Arg Ser Leu Cys Ser Cys Gly Asp Arg Pro Ile Ala Asp Gly Ser Leu
            420                 425                 430

Leu Asp Phe Leu Arg Gln Val Ser Thr Phe Gly Leu Ser Leu Val Arg
            435                 440                 445

Leu Asp Ile Arg Gln Glu Ser Asp Arg His Thr Asp Val Leu Asp Ala
            450                 455                 460

Ile Thr Thr His Leu Asp Ile Gly Ser Tyr Arg Glu Trp Ser Glu Glu
465                 470                 475                 480

Arg Arg Gln Glu Trp Leu Leu Ser Glu Leu Ser Gly Lys Arg Pro Leu
            485                 490                 495

Phe Gly Ser Asp Leu Pro Lys Thr Glu Glu Ile Ala Asp Val Leu Asp
            500                 505                 510

Thr Phe His Val Ile Ala Glu Leu Pro Ala Asp Ser Phe Gly Ala Tyr
            515                 520                 525

Ile Ile Ser Met Ala Thr Ala Pro Ser Asp Val Leu Ala Val Glu Leu
530                 535                 540

Leu Gln Arg Glu Cys Arg Val Lys Gln Pro Leu Arg Val Val Pro Leu
545                 550                 555                 560

Phe Glu Lys Leu Ala Asp Leu Glu Ala Ala Pro Ala Ala Val Ala Arg
            565                 570                 575

Leu Phe Ser Val Asp Trp Tyr Lys Asn Arg Ile Asn Gly Lys Gln Glu
            580                 585                 590

Val Met Ile Gly Tyr Ser Asp Ser Gly Lys Asp Ala Gly Arg Leu Ser
            595                 600                 605

Ala Ala Trp Gln Leu Tyr Lys Ala Gln Glu Glu Leu Val Lys Val Ala
610                 615                 620

Lys Glu Tyr Gly Val Lys Leu Thr Met Phe His Gly Arg Gly Gly Thr
625                 630                 635                 640

Val Gly Arg Gly Gly Gly Pro Thr His Leu Val Ile Leu Ser Gln Pro
            645                 650                 655

Pro Asp Thr Ile Asn Gly Ser Leu Arg Val Thr Val Gln Gly Glu Val
            660                 665                 670

Ile Glu Gln Ser Phe Ser Glu Glu His Leu Cys Phe Arg Thr Leu Gln
            675                 680                 685

Arg Phe Thr Ala Ala Thr Leu Glu His Gly Met Arg Pro Pro Ile Ser
            690                 695                 700

Pro Lys Pro Glu Trp Arg Ala Leu Leu Asp Glu Met Ala Val Val Ala
705                 710                 715                 720

Thr Glu Glu Tyr Arg Ser Val Val Phe Gln Glu Pro Arg Phe Val Glu
            725                 730                 735

Tyr Phe Arg Leu Ala Thr Pro Glu Leu Glu Tyr Gly Arg Met Asn Ile
            740                 745                 750

Gly Ser Arg Pro Ser Lys Arg Lys Pro Ser Gly Gly Ile Glu Ser Leu
            755                 760                 765

Arg Ala Ile Pro Trp Ile Phe Ala Trp Ile Gln Thr Arg Phe His Leu
            770                 775                 780

Pro Val Trp Leu Gly Phe Gly Ser Ala Ile Arg His Val Ile Glu Lys
785                 790                 795                 800

Asp Val Arg Asn Leu His Met Leu Gln Asp Met Tyr Gln His Trp Pro
            805                 810                 815

Phe Phe Arg Val Thr Ile Asp Leu Ile Glu Met Val Phe Ala Lys Gly
            820                 825                 830

Asp Pro Gly Ile Ala Ala Leu Tyr Asp Lys Leu Leu Val Ser Glu Glu

```
                     835                 840                 845
Leu Trp Pro Phe Gly Glu Lys Leu Arg Ala Asn Phe Glu Thr Lys
850                 855                 860

Lys Leu Ile Leu Gln Thr Ala Gly His Lys Asp Leu Leu Gly Asp
865                 870                 875                 880

Pro Tyr Leu Lys Gln Gly Leu Arg Leu Arg Asp Ser Tyr Ile Thr Thr
                    885                 890                 895

Leu Asn Val Cys Gln Ala Tyr Thr Leu Lys Arg Ile Arg Asp Pro Ser
                900                 905                 910

Tyr His Val Thr Leu Arg Pro His Ile Ser Lys Glu Ile Ala Glu Ser
                915                 920                 925

Ser Lys Pro Ala Lys Glu Leu Ile Glu Leu Asn Pro Thr Ser Glu Tyr
930                 935                 940

Ala Pro Gly Leu Glu Asp Thr Leu Ile Leu Thr Met Lys Gly Ile Ala
945                 950                 955                 960

Ala Gly Leu Gln Asn Thr Gly
                965
```

<210> SEQ ID NO 15
<211> LENGTH: 970
<212> TYPE: PRT
<213> ORGANISM: Zea mays

<400> SEQUENCE: 15

```
Met Ala Ser Thr Lys Ala Pro Gly Pro Gly Glu Lys His His Ser Ile
1               5                   10                  15

Asp Ala Gln Leu Arg Gln Leu Val Pro Gly Lys Val Ser Glu Asp Asp
                20                  25                  30

Lys Leu Ile Glu Tyr Asp Ala Leu Leu Val Asp Arg Phe Leu Asn Ile
            35                  40                  45

Leu Gln Asp Leu His Gly Pro Ser Leu Arg Glu Phe Val Gln Glu Cys
        50                  55                  60

Tyr Glu Val Ser Ala Asp Tyr Glu Gly Lys Gly Asp Thr Thr Lys Leu
65                  70                  75                  80

Gly Glu Leu Gly Ala Lys Leu Thr Gly Leu Ala Pro Ala Asp Ala Ile
                85                  90                  95

Leu Val Ala Ser Ser Ile Leu His Met Leu Asn Leu Ala Asn Leu Ala
            100                 105                 110

Glu Glu Val Gln Ile Ala His Arg Arg Asn Ser Lys Leu Lys Lys
        115                 120                 125

Gly Gly Phe Ala Asp Glu Gly Ser Ala Thr Thr Glu Ser Asp Ile Glu
130                 135                 140

Glu Thr Leu Lys Arg Leu Val Ser Glu Val Gly Lys Ser Pro Glu Glu
145                 150                 155                 160

Val Phe Glu Ala Leu Lys Asn Gln Thr Val Asp Leu Val Phe Thr Ala
                165                 170                 175

His Pro Thr Gln Ser Ala Arg Arg Ser Leu Leu Gln Lys Asn Ala Arg
            180                 185                 190

Ile Arg Asn Cys Leu Thr Gln Leu Asn Ala Lys Asp Ile Thr Asp Asp
        195                 200                 205

Asp Lys Gln Glu Leu Asp Glu Ala Leu Gln Arg Glu Ile Gln Ala Ala
    210                 215                 220

Phe Arg Thr Asp Glu Ile Arg Arg Ala Gln Pro Thr Pro Gln Asp Glu
225                 230                 235                 240
```

-continued

```
Met Arg Tyr Gly Met Ser Tyr Ile His Glu Thr Val Trp Lys Gly Val
                245                 250                 255

Pro Lys Phe Leu Arg Arg Val Asp Thr Ala Leu Lys Asn Ile Gly Ile
            260                 265                 270

Asn Glu Arg Leu Pro Tyr Asn Val Ser Leu Ile Arg Phe Ser Ser Trp
        275                 280                 285

Met Gly Gly Asp Arg Asp Gly Asn Pro Arg Val Thr Pro Glu Val Thr
    290                 295                 300

Arg Asp Val Cys Leu Leu Ala Arg Met Met Ala Asn Leu Tyr Ile
305                 310                 315                 320

Asp Gln Ile Glu Glu Leu Met Phe Glu Leu Ser Met Trp Arg Cys Asn
                325                 330                 335

Asp Glu Leu Arg Val Arg Ala Glu Glu Leu His Ser Ser Ser Gly Ser
            340                 345                 350

Lys Val Thr Lys Tyr Tyr Ile Glu Phe Trp Lys Gln Ile Pro Pro Asn
        355                 360                 365

Glu Pro Tyr Arg Val Ile Leu Gly His Val Arg Asp Lys Leu Tyr Asn
    370                 375                 380

Thr Arg Glu Arg Ala Arg His Leu Leu Ala Ser Gly Val Ser Glu Ile
385                 390                 395                 400

Ser Ala Glu Ser Ser Phe Thr Ser Ile Glu Glu Phe Leu Glu Pro Leu
                405                 410                 415

Glu Leu Cys Tyr Lys Ser Leu Cys Asp Cys Gly Asp Lys Ala Ile Ala
            420                 425                 430

Asp Gly Ser Leu Leu Asp Leu Leu Arg Gln Val Phe Thr Phe Gly Leu
        435                 440                 445

Ser Leu Val Lys Leu Asp Ile Arg Gln Glu Ser Glu Arg His Thr Asp
        450                 455                 460

Val Ile Asp Ala Ile Thr Thr His Leu Gly Ile Gly Ser Tyr Arg Glu
465                 470                 475                 480

Trp Pro Glu Asp Lys Arg Gln Glu Trp Leu Leu Ser Glu Leu Arg Gly
                485                 490                 495

Lys Arg Pro Leu Leu Pro Pro Asp Leu Pro Gln Thr Asp Glu Ile Ala
            500                 505                 510

Asp Val Ile Gly Ala Phe His Val Leu Ala Glu Leu Pro Pro Asp Ser
        515                 520                 525

Phe Gly Pro Tyr Ile Ile Ser Met Ala Thr Ala Pro Ser Asp Val Leu
    530                 535                 540

Ala Val Glu Leu Leu Gln Arg Glu Cys Gly Val Arg Gln Pro Leu Pro
545                 550                 555                 560

Val Val Pro Leu Phe Glu Arg Leu Ala Asp Leu Gln Ser Ala Pro Ala
                565                 570                 575

Ser Val Glu Arg Leu Phe Ser Val Asp Trp Tyr Met Asp Arg Ile Lys
            580                 585                 590

Gly Lys Gln Gln Val Met Val Gly Tyr Ser Asp Ser Gly Lys Asp Ala
        595                 600                 605

Gly Arg Leu Ser Ala Ala Trp Gln Leu Tyr Arg Ala Gln Glu Glu Met
    610                 615                 620

Ala Gln Val Ala Lys Arg Tyr Gly Val Lys Leu Thr Leu Phe His Gly
625                 630                 635                 640

Arg Gly Gly Thr Val Gly Arg Gly Gly Gly Pro Thr His Leu Ala Ile
                645                 650                 655

Leu Ser Gln Pro Pro Asp Thr Ile Asn Gly Ser Ile Arg Val Thr Val
```

```
                    660             665                 670
Gln Gly Glu Val Ile Glu Phe Cys Phe Gly Glu Glu His Leu Cys Phe
            675             680             685

Gln Thr Leu Gln Arg Phe Thr Ala Ala Thr Leu Glu His Gly Met His
            690             695             700

Pro Pro Val Ser Pro Lys Pro Glu Trp Arg Lys Leu Met Asp Glu Met
705             710             715             720

Ala Val Val Ala Thr Glu Glu Tyr Arg Ser Val Val Lys Glu Ala
            725             730             735

Arg Phe Val Glu Tyr Phe Arg Ser Ala Thr Pro Glu Thr Glu Tyr Gly
            740             745             750

Arg Met Asn Ile Gly Ser Arg Pro Ala Lys Arg Arg Pro Gly Gly Gly
            755             760             765

Ile Thr Thr Leu Arg Ala Ile Pro Trp Ile Phe Ser Trp Thr Gln Thr
            770             775             780

Arg Phe His Leu Pro Val Trp Leu Gly Val Gly Ala Ala Phe Lys Phe
785             790             795             800

Ala Ile Asp Lys Asp Val Arg Asn Phe Gln Val Leu Lys Glu Met Tyr
            805             810             815

Asn Glu Trp Pro Phe Phe Arg Val Thr Leu Asp Leu Leu Glu Met Val
            820             825             830

Phe Ala Lys Gly Asp Pro Gly Ile Ala Gly Leu Tyr Asp Glu Leu Leu
            835             840             845

Val Ala Glu Glu Leu Lys Pro Phe Gly Lys Gln Leu Arg Asp Lys Tyr
850             855             860

Val Glu Thr Gln Gln Leu Leu Leu Gln Ile Ala Gly His Lys Asp Ile
865             870             875             880

Leu Glu Gly Asp Pro Phe Leu Lys Gln Gly Leu Val Leu Arg Asn Pro
            885             890             895

Tyr Ile Thr Thr Leu Asn Val Phe Gln Ala Tyr Thr Leu Lys Arg Ile
            900             905             910

Arg Asp Pro Asn Phe Lys Val Thr Pro Gln Pro Leu Ser Lys Glu
            915             920             925

Phe Ala Asp Glu Asn Lys Pro Ala Gly Leu Val Lys Leu Asn Pro Ala
            930             935             940

Ser Glu Tyr Pro Pro Gly Leu Glu Asp Thr Leu Ile Leu Thr Met Lys
945             950             955             960

Gly Ile Ala Ala Gly Met Gln Asn Thr Gly
                965             970
```